United States Patent
Sydora et al.

(10) Patent No.: US 9,505,675 B2
(45) Date of Patent: Nov. 29, 2016

(54) DEACTIVATION OF A PROCESS BY-PRODUCT

(71) Applicant: Chevron Phillips Chemical Company LP, The Woodlands, TX (US)

(72) Inventors: Orson L Sydora, Houston, TX (US); Bruce E Kreischer, Kingwood, TX (US); Donald A Stern, Kingwood, TX (US); Varadee Vittur, Houston, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 14/616,903

(22) Filed: Feb. 9, 2015

(65) Prior Publication Data

US 2016/0229766 A1   Aug. 11, 2016

(51) Int. Cl.

| C08F 4/06 | (2006.01) |
|---|---|
| C08F 4/24 | (2006.01) |
| C08F 210/00 | (2006.01) |
| C07C 15/02 | (2006.01) |
| C07C 2/24 | (2006.01) |
| C07C 2/02 | (2006.01) |

(Continued)

(52) U.S. Cl.
CPC . *C07C 2/32* (2013.01); *C07C 2/34* (2013.01); *C07C 2531/22* (2013.01)

(58) Field of Classification Search
CPC ............. C07C 2/30; C07C 2/32; C07C 2/36; C07C 2/34; C07C 2531/34; C07C 2531/24; C07C 2531/22; C08F 10/10; C08F 4/69

USPC ........ 526/348, 104, 100; 585/402, 513, 564, 585/512, 527

See application file for complete search history.

(56) References Cited

U.S. PATENT DOCUMENTS

| 5,198,563 A | 3/1993 | Reagen et al. |
| 5,288,823 A | 2/1994 | Reagan et al. |
| 5,331,104 A | 7/1994 | Reagen et al. |

(Continued)

FOREIGN PATENT DOCUMENTS

| EP | 0608447 A1 | 8/1994 |
| EP | 0706983 A1 | 4/1996 |

(Continued)

OTHER PUBLICATIONS

Filing receipt and specification for International application entitled "Phosphinyl Formamidine Compounds, Metal Complexes, Catalyst Systems, and their use to Oligomerize or Polymerize Olefins," filed Dec. 18, 2013 as International application No. PCT/US2013/075936.

(Continued)

*Primary Examiner* — William Cheung
(74) *Attorney, Agent, or Firm* — Conley Rose, P.C.; Rodney B. Carroll; Lynda Jolly

(57) ABSTRACT

Processes of forming oligomers are described herein. The processes generally include contacting an olefin and a catalyst system to form an oligomerization product at oligomerization conditions, wherein a reaction system effluent includes components selected from the oligomerization product, a chromium containing compound, or combinations thereof; and contacting the chromium containing compound with a beta-diketone at conditions capable of changing an oxidation state of chromium.

29 Claims, 13 Drawing Sheets

(51) Int. Cl.
*C07C 2/32* (2006.01)
*C07C 2/34* (2006.01)

(56) References Cited

U.S. PATENT DOCUMENTS

| | | |
|---|---|---|
| 5,340,785 A | 8/1994 | Reagen et al. |
| 5,360,879 A | 11/1994 | Reagen et al. |
| 5,376,612 A | 12/1994 | Reagen et al. |
| 5,382,738 A | 1/1995 | Reagen et al. |
| 5,399,539 A | 3/1995 | Reagen et al. |
| 5,438,027 A | 8/1995 | Reagen et al. |
| 5,470,926 A | 11/1995 | Reagen et al. |
| 5,523,507 A | 6/1996 | Reagen et al. |
| 5,543,375 A | 8/1996 | Lashier et al. |
| 5,563,312 A | 10/1996 | Knudsen et al. |
| 5,689,028 A | 11/1997 | Lashier et al. |
| 5,750,816 A | 5/1998 | Araki et al. |
| 5,763,723 A | 6/1998 | Reagen et al. |
| 5,814,575 A | 9/1998 | Reagen et al. |
| 5,856,257 A | 1/1999 | Freeman et al. |
| 5,856,612 A | 1/1999 | Araki et al. |
| 5,859,303 A | 1/1999 | Lashier |
| 5,910,619 A | 6/1999 | Urata et al. |
| 6,133,495 A * | 10/2000 | Urata .................. C07C 2/30 548/402 |
| 6,380,451 B1 | 4/2002 | Kreischer et al. |
| 6,455,648 B1 | 9/2002 | Freeman et al. |
| 7,157,612 B2 | 1/2007 | Ewert et al. |
| 7,285,607 B2 | 10/2007 | Blann et al. |
| 7,297,832 B2 | 11/2007 | Blann et al. |
| 7,323,524 B2 | 1/2008 | Blann et al. |
| 7,378,537 B2 | 5/2008 | Small et al. |
| 7,384,886 B2 | 6/2008 | Knudsen et al. |
| 7,476,775 B2 | 1/2009 | Kreischer |
| 7,511,183 B2 | 3/2009 | Blann et al. |
| 7,525,009 B2 | 4/2009 | Blann et al. |
| 7,718,838 B2 | 5/2010 | Woodard et al. |
| 7,820,581 B2 | 10/2010 | Knudsen et al. |
| 7,829,749 B2 | 11/2010 | Gao et al. |
| 7,906,681 B2 | 3/2011 | Gao et al. |
| 7,910,670 B2 | 3/2011 | Knudsen et al. |
| 7,964,763 B2 | 6/2011 | Dixon et al. |
| 7,994,363 B2 | 8/2011 | Gao et al. |
| 8,049,052 B2 | 11/2011 | Kreischer et al. |
| 8,076,523 B2 | 12/2011 | Bollmann et al. |
| 8,134,038 B2 | 3/2012 | McGuinness et al. |
| 8,252,955 B2 | 8/2012 | Gao et al. |
| 8,252,956 B2 | 8/2012 | Gao et al. |
| 8,268,941 B2 | 9/2012 | Kleingeld et al. |
| 8,329,608 B2 | 12/2012 | Knudsen et al. |
| 8,334,420 B2 | 12/2012 | Small et al. |
| 8,344,198 B2 | 1/2013 | Ewert et al. |
| 8,367,786 B2 | 2/2013 | Dixon et al. |
| 8,461,406 B2 | 6/2013 | Overett et al. |
| 8,471,085 B2 | 6/2013 | Sydora |
| 8,680,003 B2 | 3/2014 | Sydora et al. |
| 2009/0306442 A1 | 12/2009 | Pretorius et al. |
| 2010/0036185 A1 | 2/2010 | Yokoyama et al. |
| 2010/0113257 A1 | 5/2010 | Kreischer et al. |
| 2010/0113851 A1 | 5/2010 | Kreischer et al. |
| 2010/0113852 A1 | 5/2010 | Sydora |
| 2010/0331503 A1 | 12/2010 | Emoto et al. |
| 2011/0257350 A1 | 10/2011 | Jaber et al. |
| 2011/0282016 A1 | 11/2011 | Carter et al. |
| 2012/0041241 A1 | 2/2012 | Ewart et al. |
| 2012/0088933 A1 | 4/2012 | Carter et al. |
| 2012/0101321 A1 | 4/2012 | Brown et al. |
| 2012/0142989 A1 | 6/2012 | Jaber et al. |
| 2012/0199467 A1 | 8/2012 | Gildenhuys et al. |
| 2012/0271087 A1 | 10/2012 | Brown et al. |
| 2012/0316303 A1 | 12/2012 | Hanton et al. |
| 2013/0150605 A1 | 6/2013 | Sydora et al. |
| 2013/0150642 A1 | 6/2013 | Sydora et al. |
| 2013/0331629 A1 | 12/2013 | Sydora et al. |

FOREIGN PATENT DOCUMENTS

| | | |
|---|---|---|
| EP | 2684857 A1 | 1/2014 |
| WO | 2011082192 A1 | 7/2011 |
| WO | 2013013300 A1 | 1/2013 |

OTHER PUBLICATIONS

Foreign communication from a related counterpart application—International Search Report and Written Opinion, PCT/US2013/075936, Sep. 3, 2014, 8 pages.

McNaught, Alan D., et al., "Compendium of Chemical Terminology," International Union of Pure and Applied Chemistry, Second edition, 1997, 1 page, Wiley-Blackwell.

Mehrotra, R. C., et al., "Oxygen-bonded β-Diketonato Complexes," Metal β-Diketonates and Allied Derivatives, 1978, pp. 17-18 plus 4 pages cover and publishing information, vol. 12, Academic Press.

Sievers, Robert E., et al., "Tris(1,1,1,2,2,3,3-Heptafluoro-7,7-Dimethyl-4,6-Octanedionato)iron(III) and Related Complexes," Inorganic Syntheses, 1970, pp. 72-77 plus 4 pages cover and publishing information, vol. XII, McGraw-Hill Book Company, Inc.

Foreign communication from a related counterpart application—International Search Report and Written Opinion, PCT/US2016/016589, Apr. 21, 2016, 10 pages.

\* cited by examiner

DEACTIVATION OF A PROCESS BY-PRODUCT

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND

Field of the Invention

The present invention generally relates to oligomerization production processes.

Related Art

This section introduces information from the art that may be related to or provide context for some aspects of the techniques described herein and/or claimed below. This information is background facilitating a better understanding of that which is disclosed herein. This is a discussion of "related" art. That such art is related in no way implies that it is also "prior" art. The related art may or may not be prior art. The discussion is to be read in this light, and not as admissions of prior art.

Reaction systems are used in a variety of industrial chemical processes, for example oligomerization and/or polymerization of olefins (commonly known as alkenes) to produce oligomers and/or polymers, respectively. For example, the synthesis of 1-hexene from ethylene using a chromium catalyst system constitutes a commercially significant process for the selective preparation of an alpha olefin (1-hexene). A widely reported chromium catalyst system for the selective production of 1-hexene comprises a chromium compound, a pyrrole compound, and a metal alkyl. Many applications exist for oligomerized olefins, including employment as intermediates in the manufacture of detergents, as more environmentally friendly replacements where refined oils might otherwise be used, as monomers or comonomers in the production of polyolefins (e.g., polyethylene), and as intermediates for many other types of products. Demand for olefin oligomers continues to rise, and olefin oligomer producers seek adequate capacity to meet demand, for example via improved reaction systems and methods of making and using same.

The present invention is directed to resolving, or at least reducing, one or all of the problems mentioned above.

SUMMARY

Various embodiments of the present invention comprise processes of forming oligomers. The processes generally comprise contacting an olefin and a catalyst system to form an oligomerization product at oligomerization conditions, wherein a reaction system effluent comprising components selected from the oligomerization product, a chromium containing compound or combinations thereof; and contacting the chromium containing compound with a beta-diketone at conditions capable of changing an oxidation state of chromium.

One or more embodiments comprise the process of the preceding embodiment, wherein the chromium containing compound contacts the beta-diketone in the presence of the oligomerization product.

One or more embodiments comprise the process of any preceding embodiment further comprising separating at least a portion of the components within the reaction system effluent.

One or more embodiments comprise the process of the preceding embodiment, wherein the separation comprises at least one separation vessel selected from columns, tanks, flash vessels, distillation columns, or combinations thereof, and wherein the beta-diketone contacts the chromium containing compound at one or more locations within the separation.

One or more embodiments comprise the process of any preceding embodiment, wherein the beta-diketone contacts the chromium containing compound prior to separation of the components.

One or more embodiments comprise the process of any preceding embodiment further comprising separating light boiling components from heavier boiling components present in the reaction system effluent within a first vessel to form a first vessel overhead stream and a first vessel bottoms stream, wherein the first vessel bottoms stream comprises at least a portion of the chromium containing compound; and contacting the beta-diketone with the first vessel bottoms stream.

One or more embodiments comprise the process of the preceding embodiment, wherein the first vessel comprises a flash vessel.

One or more embodiments comprise the process of any preceding embodiment further comprising separating light boiling components from heavier boiling components present in the reaction system effluent within a first vessel to form a first vessel overhead stream and a first vessel bottoms stream, wherein the first vessel bottoms stream comprises the chromium containing compound; passing the first vessel bottoms stream to a second vessel adapted to separate the components therein and form a second vessel overhead stream and a second vessel bottoms stream, wherein the second vessel bottoms stream comprises at least a portion of the chromium containing compound; and contacting the beta-diketone with the second vessel bottoms stream.

One or more embodiments comprise the process of any preceding embodiment further comprising separating light boiling components from heavier boiling components present in the reaction system effluent within a first vessel to form a first vessel overhead stream and a first vessel bottoms stream, wherein the first vessel bottoms stream comprises at least a portion of the chromium containing compound; passing the first vessel bottoms stream to a second vessel adapted to separate the components therein and form a second vessel overhead stream and a second vessel bottoms stream, wherein the second vessel bottoms stream comprises at least a portion of the chromium containing compound; passing the second vessel bottoms stream to a third vessel adapted to separate the components therein and form a third vessel overhead stream and a third vessel bottoms stream, wherein the third vessel bottoms stream comprises at least a portion of the chromium containing compound; and contacting the beta-diketone with the third vessel bottoms stream.

One or more embodiments comprise the process of any preceding embodiment further comprising storing at least a portion of the reaction system effluent within a storage vessel and wherein the at least a portion of the reaction system effluent comprises at least a portion of the chromium containing compound; and contacting the beta-diketone with the at least the portion of the reaction system effluent within the storage vessel.

One or more embodiments comprise the process of any preceding embodiment further comprising separating light boiling components from heavier boiling components present in the reaction system effluent within a first vessel to form a first vessel overhead stream and a first vessel bottoms stream, wherein the first vessel bottoms stream comprises the chromium containing compound; passing the first vessel bottoms stream to a second vessel adapted to separate the components therein and form a second vessel overhead stream and a second vessel bottoms stream, wherein the second vessel bottoms stream comprises at least a portion of the chromium containing compound; passing the second vessel bottoms stream to a third vessel adapted to separate the components therein and form a third vessel overhead stream and a third vessel bottoms stream, wherein the third vessel bottoms stream comprises at least a portion of the chromium containing compound; storing at least a portion of the third vessel bottoms stream within a storage vessel; and contacting the beta-diketone with the third vessel bottoms stream within the storage vessel.

One or more embodiments comprise the process of any preceding embodiment further comprising separating light boiling components from heavier boiling components present in the reaction system effluent within a first vessel to form a first vessel overhead stream and a first vessel bottoms stream, wherein the first vessel bottoms stream comprises at least a portion of the chromium containing compound; passing the first vessel bottoms stream to a second vessel adapted to separate the components therein and form a second vessel overhead stream and a second vessel bottoms stream, wherein the second vessel bottoms stream comprises at least a portion of the chromium containing compound; passing the second vessel bottoms stream to a third vessel adapted to separate the components therein and form a third vessel overhead stream and a third vessel bottoms stream, wherein the third vessel bottoms stream comprises at least a portion of the chromium containing compound; storing at least a portion of the third vessel bottoms stream within a storage vessel; and contacting the beta-diketone with a) the reaction system effluent, b) the first vessel bottoms stream, c) the second vessel bottoms stream, d) the third vessel bottoms stream, e) the reaction system effluent, the first vessel bottoms stream, the second vessel bottoms stream, or the third vessel bottoms stream within the storage vessel or f) combinations thereof.

One or more embodiments comprise the process of any preceding embodiment, wherein the beta-diketone is selected from $C_5$ to $C_{30}$ beta-diketones.

One or more embodiments comprise the process of any preceding embodiment, wherein the beta-diketone is selected from $C_5$ to $C_{20}$ beta-diketones.

One or more embodiments comprise the process of any preceding embodiment, wherein the beta-diketone is selected from $C_5$ to $C_{10}$ beta-diketones.

One or more embodiments comprise the process of any preceding embodiment, wherein the beta-diketone is selected from acetylacetone, dibenzoylmethane, dipivaloylmethane, hexafluoroacetylacetone, or combinations thereof.

One or more embodiments comprise the process of any preceding embodiment, wherein the beta-diketone has a water content of less than 400 ppm, 300, ppm, 200, ppm, 100, ppm, 75 ppm, 50 ppm, 25 ppm, or 10 ppm by weight.

One or more embodiments comprise the process of any preceding embodiment, wherein the catalyst system comprises a chromium compound, a heteroatomic ligand and a metal alkyl compound.

One or more embodiments comprise the process of the preceding embodiment, wherein the heteroatomic ligand is selected from pyrrole compounds, diphosphinoaminyl compounds, $N^2$-phosphinylamidine compounds, $N^2$-phosphinylformamidine compounds, phosphinyl guanidine compounds or combinations thereof.

One or more embodiments comprise the process of any preceding embodiment, wherein the catalyst system is selected from a catalyst system comprising: a) a chromium compound, a pyrrole compound, a metal alkyl compound, and optionally, a halide containing compound; b) a chromium compound, a diphosphinoaminyl compound, and a metal alkyl compound; c) a chromium compound complexed to a diphosphinoaminyl compound, and a metal alkyl compound; d) a chromium compound, an $N^2$-phosphinylamidine compound, and a metal alkyl compound; e) a chromium compound complexed to an $N^2$-phosphmylamidine compound, and a metal alkyl compound; f) a chromium compound, an $N^2$-phosphinylformamidine compound, and a metal alkyl compound; g) a chromium compound complexed to an $N^2$-phosphinylformamidine compound, and a metal alkyl compound; h) a chromium compound, an $N^2$-phosphinyl guanidine compound, and a metal alkyl compound; i) a chromium compound complexed to an $N^2$-phosphinyl guanidine compound, and a metal alkyl compound; or j) combinations thereof.

One or more embodiments comprise the process of any preceding embodiment, wherein the metal alkyl compound is selected from alkylaluminum compounds, aluminoxanes, or combinations thereof.

One or more embodiments comprise the process of any preceding embodiment further comprising contacting the catalyst system present in the reaction system effluent with i) a catalyst system deactivating and quench agent or ii) a catalyst system deactivating agent.

One or more embodiments comprise the process of the preceding embodiment, wherein the catalyst system deactivating and quench agent or catalyst system deactivating agent is selected from the group consisting of mono-alcohols, diols, polyols, and mixtures thereof.

One or more embodiments comprise the process of any preceding embodiment, wherein the beta-diketone contacts the chromium containing compound in the presence of the catalyst system deactivating and quench agent or catalyst system deactivating agent.

One or more embodiments comprise the process of any preceding embodiment, wherein the catalyst system deactivating and quench agent or catalyst system deactivating agent is selected from a $C_4$ to $C_{12}$ mono-alcohol One or more embodiments comprise the process of any preceding embodiment, wherein the catalyst system deactivating and quench agent or catalyst system deactivating agent comprises 2-ethyl-1-hexanol.

One or more embodiments comprise the process of any preceding embodiment, wherein the olefin comprises ethylene.

One or more embodiments comprise the process of any preceding embodiment, wherein the oligomerization product comprises 1-hexene, 1-octene, or combinations thereof.

One or more embodiments comprise the process of any preceding embodiment, wherein the beta-diketone contacts the chromium containing compound in an amount sufficient to render the chromium containing compound non-pyrophoric.

The above embodiments present a simplified summary of the presently disclosed subject matter in order to provide a basic understanding of some aspects thereof. The summary is not an exhaustive overview, nor is it intended to identify key or critical elements to delineate the scope of the subject matter claimed below. Its sole purpose is to present some concepts in a simplified form as a prelude to the more detailed description set forth below.

BRIEF DESCRIPTION OF THE DRAWINGS

The patent application subject matter may be understood by reference to the following description taken in conjunction with the accompanying drawings, in which like reference numerals identify like elements, and in which.

Figure 1:
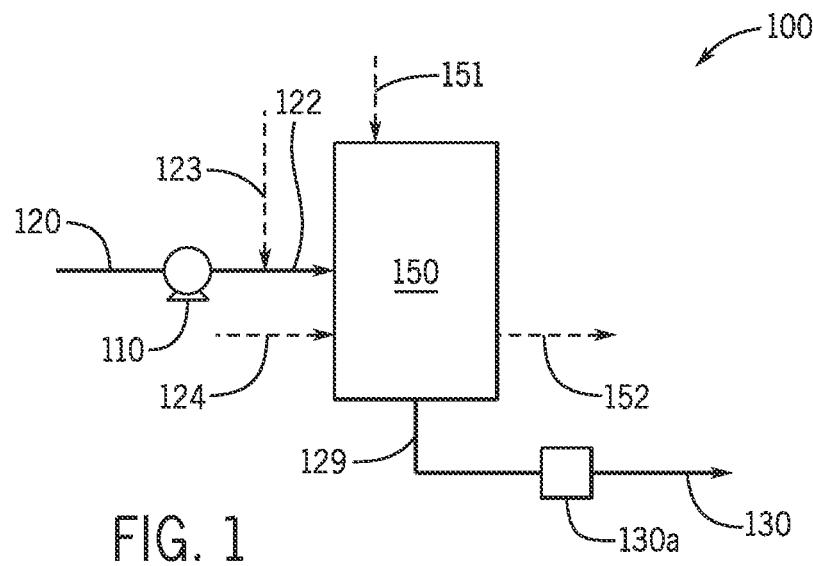
FIG. 1 illustrates an embodiment of all or a portion of a reaction process.

While the patent application subject matter is susceptible to various modifications and alternative forms, the drawings illustrate specific embodiments herein described in detail by way of example. It should be understood, however, that the description herein of specific embodiments is not intended to limit the claimed subject matter to the particular forms disclosed, but on the contrary, the intention is to cover all modifications, equivalents, and alternatives falling within the spirit and scope of the invention as defined by the appended claims.

DETAILED DESCRIPTION

Illustrative embodiments of the subject matter claimed below will now be disclosed. In the interest of clarity, not all features of an actual implementation are described in this specification. It can be appreciated that in the development of any such actual embodiment, numerous implementation-specific decisions must be made to achieve the developers' specific goals, such as compliance with system-related and business-related constraints, which can vary from one implementation to another. Moreover, it can be appreciated that such a development effort, even if complex and time-consuming, would be a routine undertaking for those of ordinary skill in the art having the benefit of this disclosure.

In the description herein, various ranges and/or numerical limitations can be expressly stated below. It should be recognized that unless stated otherwise, it is intended that endpoints are to be interchangeable. Further, any ranges include iterative ranges of like magnitude falling within the expressly stated ranges or limitations.

Furthermore, various modifications can be made within the scope of the invention as herein intended, and embodiments of the invention can include combinations of features other than those expressly claimed. In particular, flow arrangements other than those expressly described herein are within the scope of the invention.

Unless otherwise specified, the terms "contact" and "combine," and their derivatives, can refer to any addition sequence, order, or concentration for contacting or combining two or more components of the disclosed embodiments. Combining or contacting of oligomerization components can occur in one or more reaction zones under suitable contact conditions such as temperature, pressure, contact time, flow rates, etc.

Regarding claim transitional terms or phrases, the transitional term "comprising", which is synonymous with "including," "containing," "having" or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Absent an indication to the contrary, when describing a compound or composition "consisting essentially of" is not to be construed as "comprising," but is intended to describe the recited component that includes materials which do not significantly alter composition or method to which the term is applied. For example, a feedstock consisting of a material A can include impurities typically present in a commercially produced or commercially available sample of material A. When a claim includes different features and/or feature classes (for example, a method step, feedstock features, and/or product features, among other possibilities), the transitional terms comprising, consisting essentially of, and consisting of apply only to the feature class that is utilized and it is possible to have different transitional terms or phrases utilized with different features within a claim. For example a method can comprises several recited steps (and other non-recited steps) but utilize a catalyst system preparation consisting of specific steps but utilize a catalyst system comprising recited components and other non-recited components.

Within this specification, use of "comprising" or an equivalent expression contemplates the use of the phrase "consisting essentially of," "consists essentially of," or equivalent expressions as alternative embodiments to the open-ended expression. Additionally, use of "comprising" or an equivalent expression or use of "consisting essentially of" in the specification contemplates the use of the phrase "consisting of," "consists of," or equivalent expressions as an alternative to the open-ended expression or middle ground expression, respectively. For example, "comprising" should be understood to include "consisting essentially of," and "consisting of" as alternative embodiments for the aspect, features, and/or elements presented in the specification unless specifically indicated otherwise.

While compositions and methods are described in terms of "comprising" various components or steps, the compositions and methods can also "consist essentially of" or "consist of" the various components or steps.

The terms "a," "an," and "the" are intended, unless specifically indicated otherwise, to include plural alternatives, e.g., at least one. For instance, the disclosure of "a trialkylaluminum compound" is meant to encompass one trialkylaluminum compound, or mixtures or combinations of more than one trialkylaluminum compound unless otherwise specified.

Within this specification, the word "reactor" refers to a single piece of equipment, such as, for example, a vessel, in which a reaction takes place, but excludes any associated equipment such as piping, pumps, and the like which is external to the vessel. Examples of reactors include stirred tank reactors (e.g., a continuous stirred tank reactor), plug flow reactors, or any other type of reactor. Within this specification "reactor system" refers to any portion of equipment in which a reaction occurs, including but not limited to, a reactor, associated piping, associated pumps, and any other associated equipment. It should be noted that in some cases a "reactor" can also be a "reactor system." For example, in some instances a polyethylene loop reactor can be considered a reactor system.

Within this specification, term "reaction system" refers to the portion of a process, the associated equipment and associated process lines where all the necessary reaction components and reaction conditions are present such that the reaction can occur at a desired rate. That is to say that the reaction system begins where the necessary reaction components and reaction conditions are present to maintain the reaction within 25 percent of the average reaction rate and the reaction system ends where the conditions do not maintain a reaction rate within 25 percent of the average reaction rate (based upon a volume average of the reaction rate of the reaction system). For example, in terms of an ethylene oligomerization process, the reaction system begins at the point where sufficient ethylene and active catalyst system is present under the sufficient reaction conditions to maintain oligomer product production at the desired rate and the reaction system ends at a point where either the catalyst system is deactivated, sufficient ethylene is not present to sustain oligomer product production, or other reaction conditions are not sufficient to maintain the oligomer product production or the desired oligomer product production rate. Within this specification the "reaction system" can comprise one or more reactor systems, one or more reactors, and associated equipment where all the necessary reaction components and reaction conditions are present such that the reaction can occur at a desired rate.

The term "reaction process" refers to the equipment of the reaction process including the equipment of the reaction system and the equipment and associated process line(s) which can bring the necessary component(s) into and out of the reaction system.

Within this specification, reference to heavy oligomerization, trimerization, tetramerization, or trimerization and tetramerization product or product components refers to the portion of the oligomer product that is heavier (on a gram molecular weight basis) than the desired oligomerization, trimerization, tetramerization, or trimerization and tetramerization product or products components. For example a heavy trimerization product or product component can include those products or product components containing more than three monomer units. Within this specification, reference to heavy liquid or heavy solid oligomerization, trimerization, tetramerization, or trimerization and tetramerization product or product components refers to the physical state (i.e., liquid or solid) of the heavy oligomerization, trimerization, tetramerization, and/or trimerization an tetramerization product or product components product components at standard ambient temperature and pressure. For this specification, standard ambient temperature and pressure is defined as a temperature of 298.15 K (25° C., 77° F.) and an absolute pressure of 100 kPa.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to hexene includes 1-hexene, 2-hexene, 3-hexene, and any other hydrocarbon having 6 carbon atoms (linear, branched or cyclic) and a single carbon carbon double bond. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

Within this disclosure the normal rules of organic nomenclature prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4 position and hydrogens located at the 2, 3, 5, and 6 positions. References to compounds or groups having substitution at positions in addition to the indicated position can be referenced using comprising or some other alternative language. For example a reference to a phenyl group comprising a substituent at the 4 position refers to a group having a group at the 4 position and hydrogen or any non-hydrogen group at the 2, 3, 5, and 6 positions.

Processes of forming oligomers are described herein. Such processes generally comprise contacting an olefin and a catalyst system to form an oligomerization product at oligomerization conditions. As used herein, the term "oligomerization" and its derivatives, refers to processes which produce a mixture of products containing at least 70 weight percent products containing from 2 to 30 monomer units. Similarly, as used herein, an "oligomer" is a product that contains from 2 to 30 monomer units while an "oligomerization product" includes all products made by the "oligomerization" process including the "oligomers" and products which are not "oligomers" (e.g., products which contain more than 30 monomer units). It should be noted that the monomer units in the "oligomer" or "oligomerization product" do not have to be the same. For example, an "oligomer" or "oligomerization product" of an "oligomerization" process using ethylene and propylene as monomers can contain both ethylene and/or propylene units.

As used herein the term "trimerization," and it derivatives, refers to a process which produces a mixture of products containing at least 70 weight percent products containing three and only three monomer units. As used herein a "trimer" is a product which contains three and only three monomer units while a "trimerization product" includes all products made by the trimerization process including trimer and product which are not trimer (e.g. dimers or tetramers). Generally, an olefin trimerization reduces number of olefinic bonds, i.e., carbon-carbon double bonds, by two when considering the number of olefin bonds in the monomer units and the number of olefin bonds in the trimer. It should be noted that the monomer units in the "trimer" or "trimerization product" do not have be the same. For example, a "trimer" of a "trimerization" process using ethylene and butene as monomers can contain ethylene and/or butene monomer units. That is to say the "trimer" can include $C_6$, $C_8$, $C_{10}$, and $C_{12}$ products. In another example, a "trimer" of a "trimerization" process using ethylene as the monomer can contain ethylene monomer units. It should also be noted that a single molecule can contain two monomer units. For example, dienes such as 1,3-butadiene and 1,4-pentadiene have two monomer units within one molecule. In an example, a "trimerization" process using ethylene as the monomer produces a mixture of products containing at least 70 weight percent hexene.

The term "tetramerization," and its derivatives, refers to a process which produces a mixture of products containing at least 70 weight percent products containing four and only four monomer units. As used herein a "tetramer" is a product which contains four and only four monomer units while a "tetramerization product" includes all products made by the tetramerization process including tetramer and product which are not tetramer (e.g. dimers or trimer). Generally, an olefin tetramerization reduces number of olefinic bonds, i.e., carbon-carbon double bonds, by three when considering the number of olefin bonds in the monomer units and the number of olefin bonds in the tetramer. It should be noted that the monomer units in the "tetramer" or "tetramerization product" do not have be the same. For example, a "tetramer" of a "tetramerization" process using ethylene and butene as monomers can contain ethylene and/or butene monomer units. In an example, a "tetramer" of a "tetramerization" process using ethylene as the monomer can contain ethylene monomer units. It should also be noted that a single molecule can contain two monomer units. For example, dienes such as 1,3-butadiene and 1,4-pentadiene have two monomer units within one molecule. In an example, a "tetramerization" process using ethylene as the monomer produces a mixture of products containing at least 70 weight percent octene.

The term "trimerization and tetramerization," and it derivatives, refers to a process which produces a mixture of products containing at least 70 weight percent products containing three and/or four and only three and/or four monomer units. As used herein a "trimerization and tetramerization product" includes all products made by the "trimerization and tetramerization" process including trimer, tetramer, and products which are not trimer or tetramer (e.g. dimers). In an example, a "trimerization and tetramerization" process using ethylene as the monomer produces a mixture of products containing at least 70 weight percent hexene and/or octene.

The olefin and the catalyst system are generally contacted with one another within a reaction system. The reaction system can be referred to as an oligomerization, trimerization, tetramerization, or trimerization and tetramerization reaction system depending upon the catalyst system utilized and the products obtained. The reactor can be referred to as an oligomerization, trimerization, tetramerization, or trimerization or tetramerization reactor depending upon the catalyst system utilized and the products obtained. The reaction system effluent can be referred to as an oligomerization, trimerization, tetramerization, or trimerization or tetramerization reaction system effluent depending upon the catalyst system utilized and the products obtained. The reaction mixture can be referred to as an oligomerization, trimerization, tetramerization, or trimerization or tetramerization mixture depending upon the catalyst system utilized and the products obtained.

In an embodiment the reactor system, reactor system, or reaction system can be operated in a batch or continuous manner. In some embodiments, the reactor, reactor system, or reaction system can be operated in a batch manner. In some embodiments, the reactor system, reactor system, or reaction system can be operated in a semi-continuous manner, or alternatively, a continuous manner.

Generally, the reaction system can comprise one or more reactors, one or more discharge locations, and one or more feed lines for one or more feeds. For example, the reaction system can comprise from one to six reactors, from one to four reactors, from one to three reactors, or from one to two reactors. In specific embodiments, the reaction system can comprise a single reactor, two reactors, three reactors or four reactors, for example. When the reaction system has more than one reactor, the reactors can be in series or parallel and can be connected using one or more process lines, depending upon the actual design. In an embodiment, the reaction system can further comprise a motive device (e.g., a pump), one or more process lines from the motive device to the reactor(s) (in terms of process flow) and one or more process lines from the reactor(s) to the motive device (in relation to process flow).

In an embodiment, the oligomerization, trimerization, tetramerization, or tetramerization and trimerization can be operated in a continuous manner (i.e., can be a continuous process) carried out in one or more reactors. In some embodiments, each oligomerization, trimerization, tetramerization, or tetramerization and trimerization reactor of the continuous reaction system independently can be a stirred tank reactor (e.g. a continuous stirred tank reactor, among others), a plug flow reactor, or any other type of reactor; alternatively, a stirred tank reactor, a plug flow reactor, or any combination thereof; alternatively, a stirred tank reactor; or alternatively, a plug flow reactor. In other embodiments, the continuous reaction system can comprise different types of reactors in combination, and in various arrangements.

In an embodiment, the reaction system can have only one discharge from the reaction system. In some embodiments, the reaction system can have more than one discharge, or only one discharge per reactor in the reaction system, or more discharges than reactors in the reaction system, for example. Generally, the reaction system discharge can be located anywhere along the reaction system. In an embodiment, the reaction system discharge(s) can be located on a reaction system process line, or a reactor inlet, or a reactor outlet. When the reaction system discharge(s) is located on a process line, the discharge(s) can be located on a process line from a reactor, on a process line from a reactor to the motive device (in relation to process flow), on a process recycle line from the motive device to a reactor (in terms of process flow), or any combination thereof, or on a process line from a reactor, or on any process line from a reactor to the motive device, or on a process recycle line from the motive device to a reactor(s), for example. In some embodiments, the reaction system discharge can be located at point within the reaction system where the reaction mixture is well mixed (e.g., within a short distance after a motive device and/or a reactor outlet). When the reaction system has more than one reactor connected in series, a reaction system discharge can be located on a process line exiting the final reactor in the series, or a reaction system discharge(s) can be located on a process line(s) connecting two reactors operating in recycle. When the reaction system is operated in recycle and the reaction system has more than one reactor connected in parallel, a reaction system discharge(s) can be located on a process line(s) prior to a point where the reaction mixture from the one or more parallel reactors is combined, or on a process line after a point where the reaction mixture from at least two parallel reactors is combined, or on a process line after a point where the reaction mixture from all the parallel reactors is combined. When the reaction system is operated in recycle and the reaction system can have more than one reactor connected in parallel, a reaction system discharge(s) can be located on a process line(s) after the motive device (in relation to process flow) but prior to a point where the reaction mixture is split to go to the one or more parallel reactors, or on one or more of the process lines after the motive device and after a point where the reaction mixture is split to go to the one or more parallel reactors, or on each process line after the motive device and after a point where the reaction mixture is split to go to the one or more parallel reactors.

In an embodiment, the reaction system can have a single feed line per distinctive feed to the reaction system. In some embodiments, the reaction system can have more than one feed line per distinctive feed to the reaction system, or a single feed line per distinctive feed to the reaction system per reactor, or more feed lines per distinctive feed to the reaction system per reactor, for example. Generally, the feed line(s) can be placed anywhere along the reaction system. In an embodiment, the reaction system feed line(s) can be located on a reaction system process line, or a reactor inlet, or a reactor outlet (e.g., when the reaction system has two reactors operating in series or the reaction system is operated in recycle). When the reaction system feed line(s) is located on a process line, the feed line(s) can be located on a process line from the motive device to a reactor (in terms of process flow), on a process line from the reactor to the motive device (in relation to process flow), or any combination thereof, or on a process line from the motive device to a reactor, or on a process line from a reactor to the motive device. When the reaction system has more than reactor connected in series, a reaction system feed line(s) can be located on a process line(s) connecting two reactors. When the reaction system is operated in recycle and the reaction system has more than one reactor connected in parallel, a reaction system feed(s) can be located on a process line(s) prior to a point where the reaction mixture from the one or more parallel reactors is combined, or on a process line after a point where the reaction mixture from at least two parallel reactors are combined, or on a process line after a point where the reaction mixture from all the parallel reactors are combined. When the reaction system has more than one reactor connected in parallel, a reaction system feed(s) can be located on a process line(s) after the motive device (in relation to process flow) but prior to a point where the reaction mixture is split to go to the one or more parallel reactors, or on one or more of the process lines after the motive device and after a point where the reaction mixture is split to go to the one or more parallel reactors, or on each process line after the motive device and after a point where the reaction mixture is split to go to the one or more parallel reactors.

FIG. 1 illustrates an embodiment of reaction process 100 in accordance with the present disclosure including all or a portion of a reaction system and its associated feed inlets, effluent outlets, and other equipment. Specifically, FIG. 1 shows a view of a reaction process 100 having a single reactor 150. As can be seen, reaction process 100 has feed inlet 120 (which represents one or more feed lines of the reaction process 100) to feed one or more reaction components though feed valve or motive device 110 and through process line 122 into reactor 150. As a reaction mixture (described in more detail herein) flows within portions of reaction process 100 (including reactor 150, motive device 130a, and process line 129, among other reaction process 100 components), reaction product (described in more detail herein) is produced. Reactor effluent can exit reactor 150 via reactor discharge 129 through process valve or pump 130a into process line 130. Lines 151 and 152 represent heat exchange medium inflow and heat exchange medium outflow lines for optional heat exchange medium to flow through reactor 150 on lines separate from process lines containing the reaction mixture. Lines 123 and 124 show optional additional feed lines to feed reaction components to process lines or reactor 150, among other places.

Figure 2:
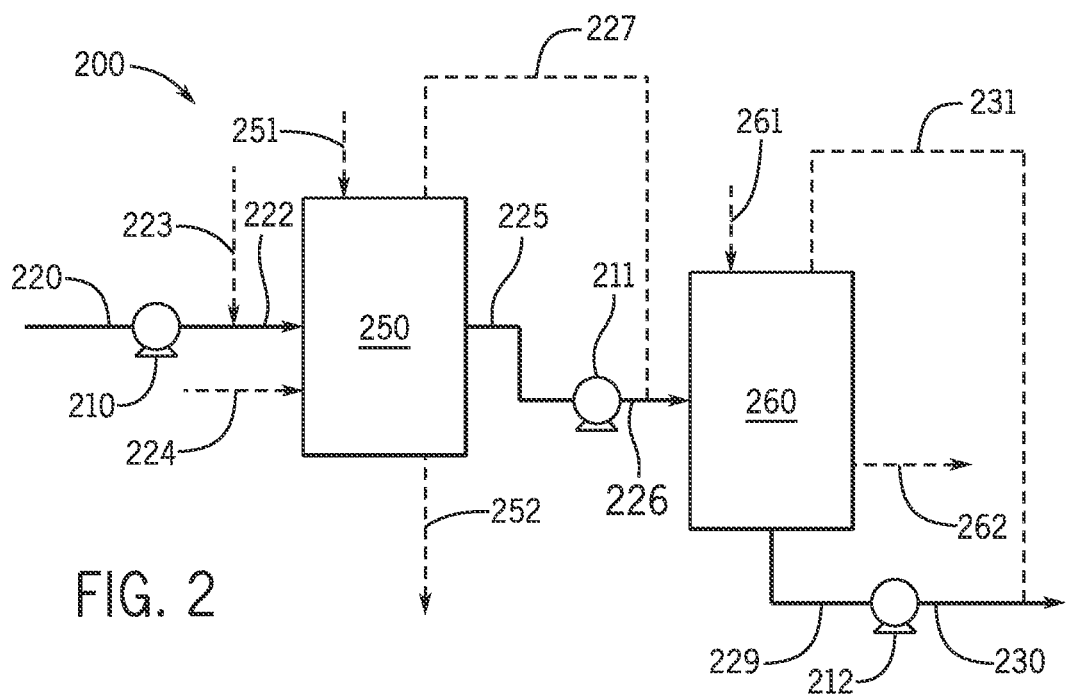
FIG. 2 illustrates an alternative embodiment of all or a portion of a reaction process having two optional recycle loops.

FIG. 2 illustrates another embodiment of reaction process 200 in accordance with the present disclosure including all or a portion of a reaction system and its associated feed inlets, effluent outlets, and other equipment. Specifically, FIG. 2 shows a view of reaction process 200 having two reactors 250 and 260 connected in series. As can be seen, reaction process 200 has feed inlet 220 (which represents one or more feed lines of reaction process 200) to feed one or more reaction components through valve or motive device 210 and through process line 222 to reactor 250. As a reaction mixture (described in more detail herein) flows within reaction process 200 (including reactors 250 and 260, motive devices/valves 211 and 212, and process lines 225 226 and 229, among other reaction process 200 components), reaction product (described in more detail herein) is produced. Reactor effluent can exit reactor 260 via reactor discharge 229 through process valve or pump 212 into process line 230. Lines 251 and 252 of reactor 250, and lines 261 and 262 of reactor 260 represent heat exchange medium inflow lines and heat exchange medium outflow lines for optional heat exchange medium to flow through reactors 250 and 260, respectively, on lines separate from process lines containing the reaction mixture. Lines 223 and 224 show optional additional feed lines to feed reaction components to process line 222 or reactor 250, respectively. Additional optional feed lines (not shown) can feed reaction components to process lines 225 and/or 226, and/or reactors 250 and/or 260, among other places. Optional process lines 227 and 231 represent process lines which can be utilized to recycle a portion of the reaction mixture through reactors 250 and 260 (respectively). The reaction mixture within optional process lines 227 and 231 can optionally be subjected to heat exchange using various heat exchange equipment (not shown) which can keep the reaction mixture separate from the heat exchange fluid medium.

Figure 3:
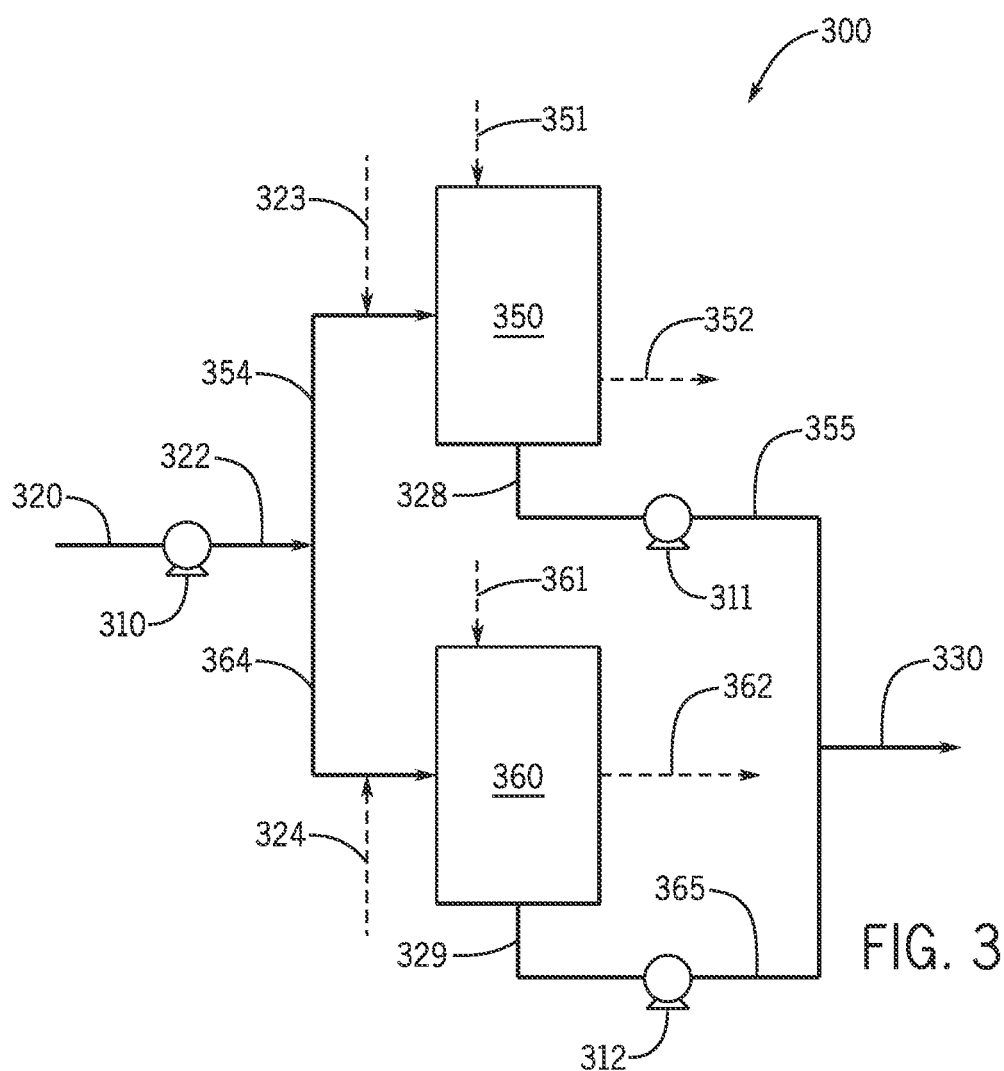
FIG. 3 illustrates an alternative embodiment of all or a portion of a reaction process.

FIG. 3 shows a further embodiment of reaction process 300 in accordance with the present disclosure including all or a portion of a reaction system and its associated feed inlets, effluent outlets, and other equipment. Specifically, FIG. 3 shows a view of reaction process 300 having two reactors 350 and 360 connected in parallel. As can be seen, reaction process 300 has feed inlet 320 (which represents one or more feed lines of reaction process 300) to feed one or more reaction components through valve or motive device 310 and process line 322 to reactors 350 and 360 through process lines 354 and 364 (respectively). As a reaction mixture (described in more detail herein) flows within reaction process 300 (including reactors 350 and 360, motive devices/valves 311 and 312, and process lines 328, 329, 355, and 365, among other reaction process 300 components), reaction product (described in more detail herein) is produced. Reactor effluent can exit reactors 350 and 360 via reactor discharges 328 and 329 (respectively) though valves or motive devices 311 and 312 (respectively) into process lines 355 and 365 (respectively) and can be combined into process line 330. Lines 351 and 352 of reactor 350, and lines 361 and 362 of reactor 360 represent heat exchange medium inflow lines and heat exchange medium outflow lines for optional heat exchange medium to flow through reactors 350 and 360, respectively, on lines separate from process lines containing the reaction mixture. Process lines 323 and 324 show optional additional feed lines to feed reaction components to the process lines 354 and 364 (respectively). Additional optional feed lines (not shown) can feed reaction components to process line 322, reactor 350, and/or reactor 360, among other places.

Figure 4:
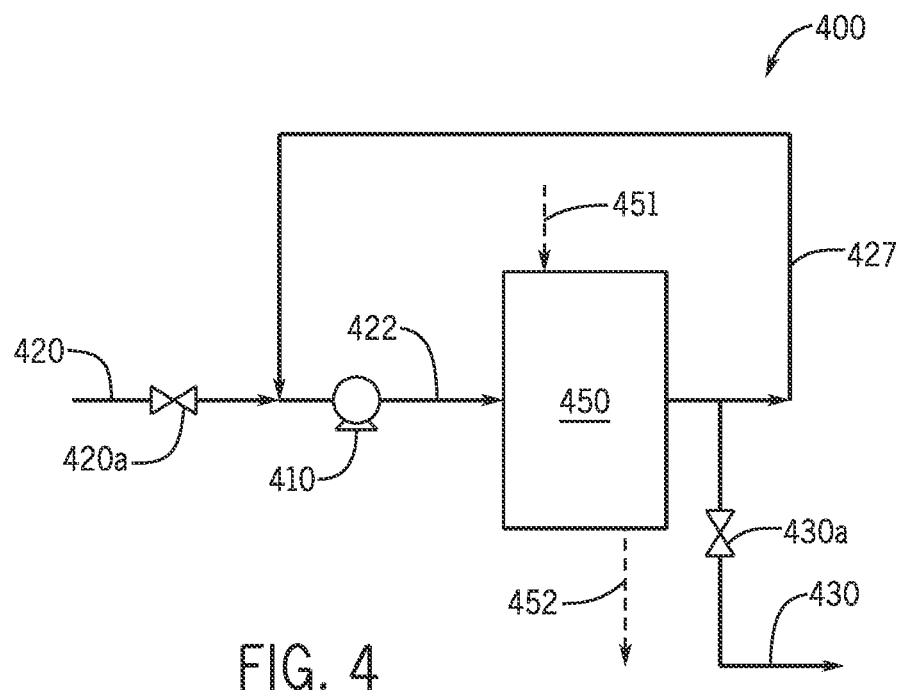
FIG. 4 illustrates an alternative embodiment of all or a portion of a reaction process having a recycle loop.

FIG. 4 illustrates an embodiment of reaction process 400 in accordance with the present disclosure including all or a portion of a reaction system and its associated feed inlets, effluent outlets, and other equipment. Specifically FIG. 4 shows a view of a reaction process 400 having a single oligomerization reactor 450. As can be seen, reaction process 400 has feed inlet 420 (which represents one or more feed lines of reaction process 400) to feed one or more reaction components through valve or motive device 420a (operating on mass or volume control) to a reaction mixture. As the reaction mixture (described in more detail herein) flows through the loop including reactor 450, motive device 410, and process lines 422 and 427 (among other reaction process components) within reaction process 400, reaction product (described in more detail below) can be produced. Effluent can exit the loop through valve or motive device 430a (operating on mass control, volume control, or pressure control) into process line 430. Lines 451 and 452 of reactor 450 represent heat exchange medium inflow and heat exchange medium outflow lines for optional heat exchange medium to flow through reactor 450 on lines separate from process lines containing the reaction mixture (when included). Additional optional feed lines (not shown) can feed reaction components to process line 422, process line 427, and/or reactor 450, among other places.

Figure 5:
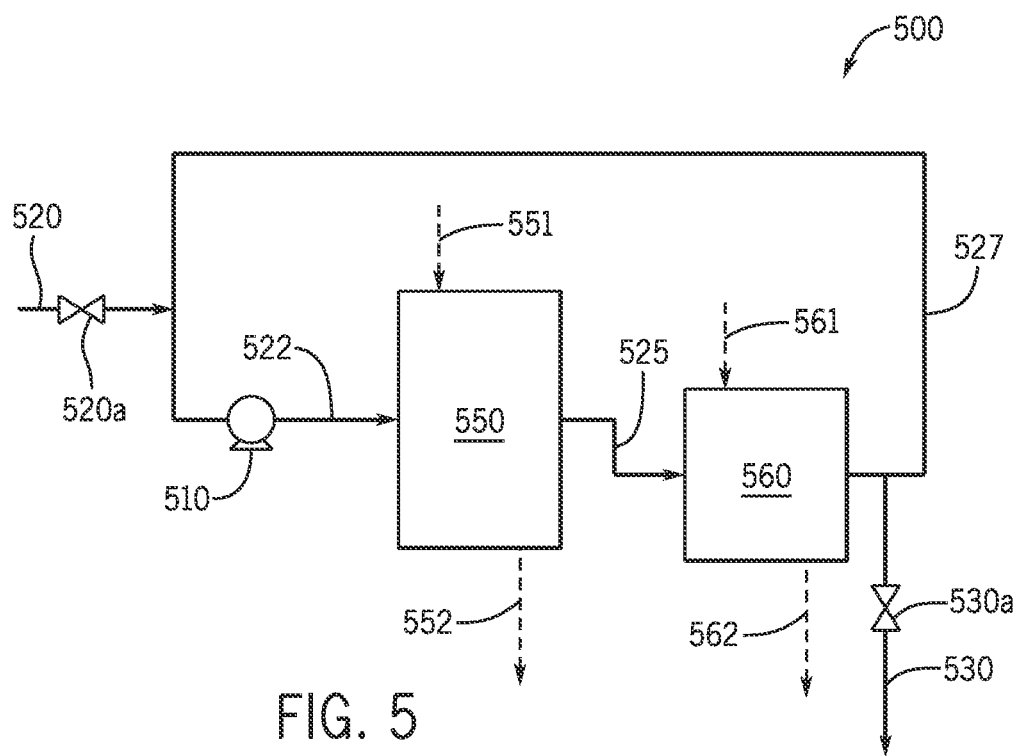
FIG. 5 illustrates an alternative embodiment of all or a portion of a reaction process having a recycle loop.

FIG. 5 illustrates an embodiment of reaction process 500 in accordance with the present disclosure including all or a portion of a reaction system and its associated feed inlets, effluent outlets, and other equipment. Specifically, FIG. 5 shows a view of reaction process 500 having two reactors 550 and 560 connected in series. As can be seen, reaction process 500 has feed inlet 520 (which represents one or more feed lines of reaction process 500) to feed one or more reaction components through valve or pump 520a (operating on mass or volume control) to a reaction mixture. As the reaction mixture (described in more detail herein) flows through a loop including reactors 550 and 560, motive device 510, and process lines 522, 525 and 527 (among other reaction process components) within reaction process 500, reaction product (described in more detail herein) can be produced. Effluent can exit the loop through valve or motive device 530a (operating on mass control, volume control, or pressure control) into process line 530. Lines 551 and 552 of reactor 550, and lines 561 and 562 of reactor 560 represent heat exchange medium inflow lines and heat exchange medium outflow lines for optional heat exchange medium to flow through reactors 550 and 560, respectively, on lines separate from process lines containing the reaction mixture. Additional optional feed lines (not shown) can feed reaction components to process line 522, process line 525, process line 527, reactor 550, and/or reactor 560, among other places.

Figure 6:
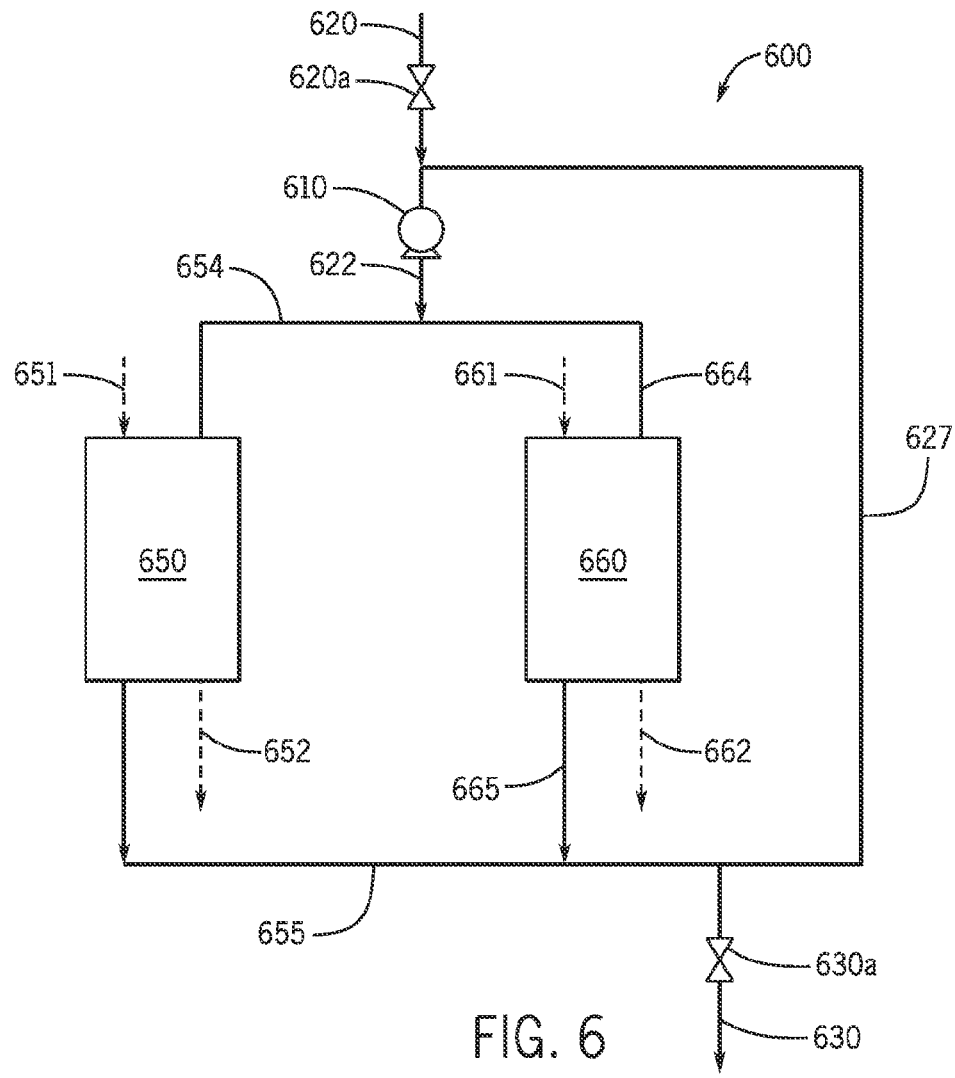
FIG. 6 illustrates an alternative embodiment of all or a portion of an oligomerization a reaction process having a recycle loop.

FIG. 6 shows an embodiment of reaction process 600 in accordance with the present disclosure including all or a portion of a reaction system and its associated feed inlets, effluent outlets, and other equipment. Specifically, FIG. 6 shows a view of reaction process 600 having two reactors 650 and 660 connected in parallel. As can be seen, reaction process 600 has feed inlet 620 (which represents one or more feed lines of reaction process 600) to feed one or more reaction components through a valve or motive device 620a (operating on mass or volume control) to a reaction mixture. As the reaction mixture (described in more detail herein) flows through a loop including reactors 650 and 660, motive device 610, and process lines 622, 654, 664, 655, 665, and 627 (among other reaction process components) within reaction process 400, reaction product (described in more detail herein) can be produced. Effluent can exit the loop through valve or motive device 630a (operating on mass control, volume control, or pressure control) into process line 630. Lines 651 and 652 of reactor 650, and lines 661 and 662 of reactor 660 represent heat exchange medium inflow lines and heat exchange medium outflow lines for optional heat exchange medium to flow through reactors 650 and 660, respectively, on lines separate from process lines containing the reaction mixture. Additional optional feed lines (not shown) can feed reaction components to process line 622, process line 654, process line 664, process line 627, reactor 650, and/or reactor 660, among other places.

Generally, reaction processes utilizing a reactor in accordance with the present disclosure (e.g., reaction processes 100, 200, 300, 400, 500, and 600, described herein, among other reaction process designs), circulates a reaction mixture within or through reactors and process lines using a motive device to produce a reaction product. Feeds to the reaction process can be introduced (either continuously or semi-continuously) through one or more feed inlets while effluent can be removed using one or more discharges. In embodiments utilizing a heat exchange medium for controlling the temperature of the reaction mixture (e.g., for removing heat produced by the reaction, or to add heat to the reaction), at least a portion of a reaction process (e.g., all or a portion of the reactors) can have a heat exchange configuration. In such embodiments, a heat exchange medium can be provided via one or more heat exchange medium inlets and removed via one or more heat exchange outlets which keep the reaction mixture separate from the heat exchange fluid medium.

The reaction mixture flowing through the reactor(s) can be agitated or stirred by any means which can create turbulent flow through all or a portion of the reaction system. For example the reaction mixture flowing through the reaction system can be agitated or stirred by: 1) the introduction of the inert gas (e.g., nitrogen purge) in a manner that can cause agitation, 2) introducing one or more reaction mixture feeds to the reaction system in a manner that can cause agitation, 3) removing effluent from the reaction system in a manner that can cause agitation, 4) by mechanical or magnetic stirring according to methods known in the art with the aid of this disclosure, 5) by using a motive device to circulate the reaction mixture through the reaction system, or 6) combinations thereof. In some embodiments, the reaction mixture can be circulated through the reactor or reaction system using a motive device. In other embodiments, the reaction mixture can be circulated through the reactor or reaction system and agitated or stirred using a motive device.

A feed device (e.g., motive device or valve 110 of FIG. 1, motive device or valve 210 of FIG. 2, motive device or valve 310 of FIG. 3, motive device or valve 420a of FIG. 4, motive device0 or valve 520a of FIG. 5, or motive device or valve 620a of FIG. 6), can continuously (alternatively, intermittently) provide reaction components of the reaction mixture to the reaction system (including one or more of the reactors, e.g., reactor 150 of FIG. 1, reactors 250 and 260 of FIG. 2, reactors 350 and 360 of FIG. 3 reactor 450 of FIG. 4, reactors 550 and 560 of FIG. 5, or reactors 650 and 660 of FIG. 6, among other reaction system components). A motive device (e.g., motive device 410 of FIG. 4, motive device 510 of FIG. 5, or motive device 610 of FIG. 6), can continuously (alternatively, intermittently) circulate the reaction mixture through the loop (including one or more of the reactors, e.g., reactor 450 of FIG. 4, reactors 550 and 560 of FIG. 5, or reactors 650 and 660 of FIG. 6, among other reaction system components). While reaction processes 100, 200, 300, 400, 500, and 600 as shown in FIGS. 1 to 6 show one or two reactors, it is contemplated any number of reactors (e.g., 1, 2, 3, 4, 5, 6, 7, 8, 9, 10, or greater) can be used for one or more of the embodiments disclosed herein.

The reaction mixture comprising the reaction product can be withdrawn from the reactor or loop for further processing (e.g., catalyst system deactivation and isolation of the reaction product, among other processing steps (e.g., reactor 150 of FIG. 1, reactor 260 of FIG. 2, or reactors 350 and 360 of FIG. 3) or loop (e.g., loop including reactor 450 of FIG. 4, loop including reactors 550 and 560 of FIG. 5, or loop including reactors 650 and 660 of FIG. 6) through a reactor outlet valve or motive device (e.g., reactor outlet valve or motive device 130a of FIG. 1, reactor outlet valve or motive device 212 of FIG. 2, or reactor outlet valves or motive devices 311 an 312 of FIG. 3) or a loop outlet valve or pump (e.g., loop valve or motive device 430a of FIG. 4, loop valve or motive device 530a of FIG. 5, or loop valve or motive device 630a of FIG. 6). The reactor outlet valve or pump, or loop outlet valve or motive device can semi-continuously, or alternatively continuously, remove a portion of the reaction mixture from the reactor or loop (e.g., a valve can be moved or actuated between a closed position and an open position so that a portion of the reaction mixture flows through the valve and into reactor or loop discharge line).

At least a portion of the components of the reaction mixture can react (e.g., via one or more reaction processes) to form a reaction product. The compositional identity of the reaction mixture can vary as the reaction mixture travels through the reaction system (comprising a reactor or loop). As reactants are consumed, reaction components can be fed to the reaction system (comprising a reactor or loop), a portion of the reaction mixture can be removed from the reactor or loop, and/or reaction products can be formed. In embodiments, the reaction mixture can comprise a liquid phase, a vapor phase, or combinations thereof. In some embodiments, the reaction mixture can be homogenous or heterogeneous. In other embodiments, the reaction mixture can have one liquid phase or more than one liquid phase.

The reactors disclosed herein (e.g., reactor 150 of FIG. 1, reactors 250 and 260 of FIG. 2, reactors 350 and 360 of FIG. 3, reactor 450 of FIG. 4, reactors 550 and 560 of FIG. 5, reactors 650 and 660 of FIG. 6) can be utilized in a continuous or semi-continuous process comprising continuously or semi-continuously introducing one or more feeds to the reaction system (e.g., via feed inlet 120 of FIG. 1, feed inlet 220 of FIG. 2, feed inlet 320 of FIG. 3, feed inlet 420 of FIG. 4, feed inlet 520 of FIG. 5, feed inlet 620 of FIG. 6), flowing the reaction mixture through the reactor(s) (and other reaction system elements), and continuous or semi-continuously removing the reaction mixture from the reactor (e.g., via reactor discharge line 129 of FIG. 1, reactor discharge line 229 of FIG. 2, reactor discharge lines 328 and 329 of FIG. 3, loop discharge valve or motive device 430a 427 of FIG. 4, loop discharge valve or motive device 530a of FIG. 5, loop discharge valve or motive device 630a of FIG. 6) as described herein). Alternatively, a batch loop process can also be employed comprising circulating the reaction mixture through the reactor(s) (e.g., reactor 450 of FIG. 4, reactors 550 and 560 of FIG. 5, reactors 650 and 660 of FIG. 6) until the reaction is complete (which is not necessarily the point at which one or more reagents is completely consumed), and then removing the contents (e.g., reaction mixture) from the reactor(s).

Generally, the reaction systems described herein (comprising the reactors and/or the loops described herein) can be utilized to perform any reaction comprising contacting one or more reactants to form a reaction product. In an embodiment, the reaction systems described herein can be utilized in an olefin oligomerization process comprising contacting an olefin and a catalyst (or a catalyst system) to form an oligomerization product. In some embodiments, the reaction systems described herein and the reactors described herein can be utilized in an olefin trimerization process comprising contacting an olefin and a catalyst (or a catalyst system) to form a trimerization product. In other embodiments, the reaction systems described herein and the reactors described herein can be utilized in an olefin tetramerization process comprising contacting an olefin and a catalyst (or a catalyst system) to form a tetramerization product. In yet other embodiments, the reaction systems described herein and the reactors described herein can be utilized in an olefin trimerization and tetramerization process comprising contacting an olefin and a catalyst (or a catalyst system) to form a trimerization and tetramerization product.

In a further embodiment, the oligomerization, trimerization, tetramerization, or trimerization and tetramerization can be performed in the presence of a solvent. In an embodiment, the oligomerization, trimerization, tetramerization, or trimerization and tetramerization can comprise contacting hydrogen with the olefin and the catalyst (or catalyst system). In an embodiment the process can further comprise recovering the oligomer, trimer, tetramer, or trimer and tetramer. Generally, the olefin, the catalyst (the catalyst system or components of the catalyst system), reaction system solvent (if utilized), hydrogen (if utilized), and any other materials can be a fed to the reaction system and can be supplied to the reaction system via the one or more feed lines described herein.

In the context of using the reaction system described herein for an olefin oligomerization process, an olefin trimerization process, an olefin tetramerization process, or an olefin trimerization and tetramerization process, the olefin (for the feed to the reaction system, or present in the reaction mixture) can comprise one or more olefins (e.g., olefin(s), alpha olefin(s), linear alpha olefin(s), or normal alpha olefin(s)). The term "linear alpha olefin" as used herein refers to a linear olefin having a double bond between the first and second carbon atom. The term "linear alpha olefin" by itself does not indicate the presence or absence of heteroatoms and/or the presence or absence of other carbon-carbon double bonds, unless explicitly indicated. The terms "linear hydrocarbon alpha olefin" or "linear alpha olefin hydrocarbon" refer to linear alpha olefin compounds containing only hydrogen and carbon. The term "normal alpha olefin" whenever used in this specification and claims refers to a linear hydrocarbon mono-olefin having a double bond between the first and second carbon atom. It is noted that "normal alpha olefin" is not synonymous with "linear alpha olefin" as the term "linear alpha olefin" can comprise linear olefinic compounds having a double bond between the first and second carbon atoms and having heteroatoms and/or additional double bonds.

In some embodiments, the olefin can comprise a $C_2$ to $C_{30}$ olefin, a $C_2$ to $C_{16}$ olefin, or a $C_2$ to $C_{10}$ olefin. In some embodiments, the olefin (regardless of carbon number) can comprise alpha olefin(s), linear alpha olefin(s), or normal alpha olefin(s). In an embodiment, the olefin can comprise ethylene. When the olefin comprises, consists essentially of, or consists of, ethylene, the process can be an ethylene oligomerization process, an ethylene trimerization process, an ethylene tetramerization process, or an ethylene trimerization and tetramerization process. When the process is an ethylene oligomerization process, the oligomerization product can comprise olefins, including normal alpha olefins. When the process is an ethylene trimerization process, the trimerization product can comprise hexenes, such as 1-hexene. When the process is an ethylene tetramerization process, the tetramerization product can comprise octenes, such as 1-octene. When the process is an ethylene trimerization and tetramerization process, the trimerization and tetramerization product can comprise hexenes and octenes, such as 1-hexene and 1-octene. In some ethylene oligomerization embodiments, the oligomerization mixture ethylene trimerization mixture, ethylene tetramerization mixture, or ethylene trimerization and tetramerization mixture can comprise at least 0.1 wt. %, 0.5 wt. %, 1 wt. %, 2.5 wt. %, 5 wt. %, 7.5 wt. %, or 10 wt. % ethylene based upon the oligomerization mixture. In other ethylene oligomerization embodiments, the oligomerization mixture, ethylene trimerization mixture, ethylene tetramerization mixture, or ethylene trimerization and tetramerization mixture can comprise a maximum of 50 wt. %, 40 wt. %, 30 wt. %, 25 wt. %, 20 wt. %, 17.5 wt. %, or 15 wt. % ethylene based upon the oligomerization mixture. In an ethylene oligomerization embodiment, the ethylene in the oligomerization mixture, ethylene trimerization mixture, ethylene tetramerization mixture, or ethylene trimerization and tetramerization mixture can range from any minimum weight percent described herein to any maximum weight percent described herein. Exemplary weight percentages for the ethylene that can be present the oligomerization mixture, ethylene trimerization mixture, ethylene tetramerization mixture, or ethylene trimerization and tetramerization mixture can comprise from 0.1 wt. % to 50 wt. %, 5 wt. % to 40 wt. %, 5 wt. % to 30 wt. %, 10 wt. % to 30 wt. %, 10 wt. % to 25 wt. %, 10 wt. % to 20 wt. %, 10 wt. % to 15 wt. %. Other ranges for the amount of ethylene that can be present in the oligomerization mixture, ethylene trimerization mixture, ethylene tetramerization mixture, or ethylene trimerization and tetramerization mixture are readily apparent from this disclosure.

In one or more embodiments, the use of the reaction system can be specifically described in relation to an ethylene oligomerization process, an ethylene trimerization process, ethylene tetramerization process, or an ethylene trimerization and tetramerization process comprising contacting a) ethylene and b) a catalyst system comprising i) a transition metal compound, ii) a heteroatomic ligand and iii) a metal alkyl compound to form an ethylene oligomerization product, an ethylene trimerization product, an ethylene tetramerization product, or an ethylene trimerization and tetramerization product (respectively). In other embodiments, the use of the reaction system can be specifically described in relation to an ethylene oligomerization process, an ethylene trimerization process, ethylene tetramerization process, or an ethylene trimerization and tetramerization process, comprising contacting a) ethylene and b) a catalyst system comprising i) a transition metal compound complexed to a heteroatomic ligand and ii) a metal alkyl compound to form an ethylene oligomerization product, an ethylene trimerization product, an ethylene tetramerization product, or an ethylene trimerization and tetramerization product (respectively). In some embodiments, an optional halogen containing compound can be a component of the catalyst system or alternatively, a halogen containing compound can be a further component contacted in the reaction system to form an ethylene oligomerization product, an ethylene trimerization product, an ethylene tetramerization product, or an ethylene trimerization and tetramerization product. In other embodiments, a solvent can be a further component contacted in the reaction system to form an ethylene oligomerization product, an ethylene trimerization product, an ethylene tetramerization product, or an ethylene trimerization and tetramerization product. In other embodiments, hydrogen can be a further component contacted in the reaction system to form an ethylene oligomerization product, an ethylene trimerization product, an ethylene tetramerization product, or an ethylene trimerization and tetramerization product. While the use of the reaction system can be described for use in the ethylene oligomerization process, ethylene trimerization process, ethylene tetramerization process, or ethylene trimerization and tetramerization process, one having ordinary skill in the art can realize that the reaction system can be utilized in other processes which can utilize a similar reaction system.

In one or more embodiments, the use of the reaction system can be specifically described in relation to an ethylene oligomerization process, an ethylene trimerization process, ethylene tetramerization process, or an ethylene trimerization and tetramerization process comprising contacting a) ethylene and b) a catalyst system comprising i) a chromium compound, ii) heteroatomic ligand and iii) a metal alkyl compound to form an ethylene oligomerization product, an ethylene trimerization product, an ethylene tetramerization product, or an ethylene trimerization and tetramerization product (respectively). In other embodiments, the use of the reaction system can be specifically described in relation to an ethylene oligomerization process, an ethylene trimerization process, ethylene tetramerization process, or an ethylene trimerization and tetramerization process, comprising contacting a) ethylene and b) a catalyst system comprising i) a chromium compound complexed to a heteroatomic ligand and ii) a metal alkyl compound to form an ethylene oligomerization product, an ethylene trimerization product, an ethylene tetramerization product, or an ethylene trimerization and tetramerization product (respectively). In some embodiments, an optional halogen containing compound can be a component of the catalyst system or alternatively, a halogen containing compound can be a further component contacted to form an ethylene oligomerization product, an ethylene trimerization product, an ethylene tetramerization product, or an ethylene trimerization and tetramerization product. In other embodiments, a solvent can be a further component contacted in the reaction system to form an ethylene oligomerization product, an ethylene trimerization product, an ethylene tetramerization product, or an ethylene trimerization and tetramerization product. In other embodiments, hydrogen can be a further component contacted in the reaction system to form an ethylene oligomerization product, an ethylene trimerization product, an ethylene tetramerization product, or an ethylene trimerization and tetramerization product. While the use of the reaction system can be described for use in the ethylene oligomerization process, ethylene trimerization process, ethylene tetramerization process, or ethylene trimerization and tetramerization process, one having ordinary skill in the art can realize that reaction system can be utilized in other processes which can utilize a similar reaction system.

In the context of using the reaction system described herein for an olefin oligomerization process, an olefin trimerization process, an olefin tetramerization process, or an olefin trimerization and tetramerization process, the process can utilize a solvent (interchangeable with reaction system solvent). As used herein, "solvent" and "reaction system solvent" includes materials which can act as a solvent or a diluent in the process described herein. As such, solvent, diluent, reaction system solvent and reaction system diluent are used interchangeably herein. In an embodiment, the solvent can be a hydrocarbon, a halogenated hydrocarbon, or a combination thereof, for example. Hydrocarbons and halogenated hydrocarbon which can be used as solvent can include, for example, aliphatic hydrocarbons, aromatic hydrocarbons, petroleum distillates, halogenated aliphatic hydrocarbons, halogenated aromatic hydrocarbons, or combinations thereof. Aliphatic hydrocarbons which can be useful as a solvent include $C_3$ to $C_{20}$ aliphatic hydrocarbons, or $C_4$ to $C_{15}$ aliphatic hydrocarbons, or $C_5$ to $C_{10}$ aliphatic hydrocarbons, for example. The aliphatic hydrocarbons which can be used as a solvent can be cyclic or acyclic and/or can be linear or branched, unless otherwise specified. Non-limiting examples of suitable acyclic aliphatic hydrocarbon solvents that can be utilized singly or in any combination include propane, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), or combinations thereof. Non-limiting examples of suitable cyclic aliphatic hydrocarbon which can be used as a solvent include cyclohexane, and methyl cyclohexane, for example. Aromatic hydrocarbons which can be useful as a solvent include aromatic hydrocarbons, or $C_6$ to $C_{10}$ aromatic hydrocarbons. Non-limiting examples of suitable aromatic hydrocarbons that can be utilized singly or in any combination as a solvent include benzene, toluene, xylene (including ortho-xylene, meta-xylene, para-xylene, or mixtures thereof), ethylbenzene, or combinations thereof. Halogenated aliphatic hydrocarbons which can be useful as a solvent include $C_1$ to $C_{15}$ halogenated aliphatic hydrocarbons, or $C_1$ to $C_{10}$ halogenated aliphatic hydrocarbons, or $C_1$ to $C_5$ halogenated aliphatic hydrocarbons, for example. The halogenated aliphatic hydrocarbons which can be used as a solvent can be cyclic or acyclic and/or can be linear or branched, unless otherwise specified. Non-limiting examples of suitable halogenated aliphatic hydrocarbons which can be utilized include methylene chloride, chloroform, carbon tetrachloride, dichloroethane, trichloroethane, and combinations thereof. Halogenated aromatic hydrocarbons which can be useful as a solvent include $C_6$ to $C_{20}$ halogenated aromatic hydrocarbons, or $C_6$ to $C_{10}$ halogenated aromatic hydrocarbons, for example. Non-limiting examples of suitable halogenated aromatic hydrocarbons which can be used as a solvent include chlorobenzene, dichlorobenzene, or combinations thereof, for example.

The choice of solvent can be made on the basis of convenience in processing. For example, isobutane can be chosen to be compatible with diluents used for the formation of polyolefins in a subsequent processing step. In some embodiments, the solvent can be chosen to be easily separable from the oligomerization product, trimerization product, tetramerization product, or trimerization and tetramerization product. In some embodiments, a component of the oligomerization product or feedstock can be utilized as the solvent. For example, since 1-hexene can be the oligomerization product of an ethylene trimerization process, it can be chosen as the solvent to decrease the need for separation. In additional or alternative embodiments, a process can be carried out in a solvent which is a product of the olefin oligomerization process. Therefore, the choice of reactor diluent, or medium, can be based on the selection of the initial olefin reactant and/or the oligomerization product. For example, if the oligomerization catalyst system is used to trimerize ethylene to 1-hexene, the solvent for the oligomerization reaction can be 1-hexene. If ethylene and hexene are trimerized, the oligomerization reaction solvent can be 1-hexene, and/or a trimerization product. If 1,3-butadiene was trimerized to 1,5-cyclooctadiene, the trimerization reactor solvent can be 1,3-butadiene or 1,5-cyclooctadiene.

In the context of using the reaction systems described herein for an ethylene trimerization process, a ethylene tetramerization process, or an ethylene trimerization and tetramerization process, the reaction mixture and/or the reaction system feed(s) (or alternatively, the ethylene trimerization mixture and/or the ethylene trimerization reaction system feeds(s), the ethylene tetramerization mixture and/or the ethylene tetramerization reaction system feeds(s), or the ethylene trimerization and tetramerization mixture and/or the ethylene trimerization and tetramerization reaction system feeds(s)) can further comprise a catalyst system (ethylene trimerization catalyst system, ethylene tetramerization catalyst system, or ethylene trimerization and tetramerization catalyst system), or further comprise one or more components of the catalyst system. The oligomerization catalyst system, the ethylene trimerization catalyst system, ethylene tetramerization catalyst system, or ethylene trimerization and tetramerization catalyst system can comprise, minimally, a transition metal compound, a heteroatomic ligand, and a metal alkyl compound. In an embodiment, the oligomerization catalyst system, the ethylene trimerization catalyst system, ethylene tetramerization catalyst system, or ethylene trimerization and tetramerization catalyst system can comprise, minimally, transition metal compound complexed to a heteroatomic ligand and a metal alkyl compound. In an embodiment, the oligomerization catalyst system, the ethylene trimerization catalyst system, ethylene tetramerization catalyst system, or ethylene trimerization and tetramerization catalyst system can comprise, minimally, a chromium compound, a heteroatomic ligand, and a metal alkyl compound. In an embodiment, the oligomerization catalyst system, the ethylene trimerization catalyst system, ethylene tetramerization catalyst system, or ethylene trimerization and tetramerization catalyst system can comprise, minimally, chromium compound complexed to a heteroatomic ligand and a metal alkyl compound. In another aspect, the oligomerization catalyst system, ethylene trimerization catalyst system, ethylene tetramerization catalyst system, or ethylene trimerization and tetramerization catalyst system can further comprise a halogen containing compound. The transition metal compound, transition metal compound complexed to a heteroatomic ligand, chromium compound, chromium compound complexed to a heteroatomic ligand, heteroatomic ligand, metal alkyl, and optional halogen containing compound are independent elements of the catalyst system. These elements of the catalyst system are independently described herein and the catalyst system can be further described utilizing any combination of the transition metal (or chromium compound) described herein, the heteroatomic ligand described herein, transition metal compound complexed to a heteroatomic ligand (or chromium compound complexed to a heteroatomic ligand) described herein, metal alkyl compound described herein, and optional halogen containing compound described herein.

Generally, the transition metal compound for the catalyst systems described herein can be a group 5, 6, 7, 8, 9, 10, or 11 transition metal compound. In some embodiments, the transition metal compound for the catalyst systems described herein can be a chromium compound, a nickel compound, a cobalt compound, an iron compound, a molybdenum compound, or a copper compound. In one or more specific embodiments, the transition metal compound for the catalyst systems described herein can be a chromium compound. The chromium compound (of the catalyst systems described herein) can have a chromium oxidation state of from 0 to 6, or from 2 to 3 (i.e., a chromium(II) compound or a chromium(III) compound). For example, chromium(II) compounds which can be used as the transition metal compound for the catalyst system described herein can comprise chromium(II) nitrate, chromium(II) sulfate, chromium(II) fluoride, chromium(II) chloride, chromium(II) bromide, or chromium(II) iodide. Also by way of example, the chromium(III) compounds which can be used as the transition metal compound for the catalyst systems described herein can comprise chromium(III) nitrate, chromium(III) sulfate, chromium(III) fluoride, chromium(III) chloride, chromium(III) bromide, or chromium(III) iodide. In yet an additional aspect of this disclosure and in any embodiment, the transition metal compound for the catalyst system can comprise a chromium(II) alkoxide, a chromium(II) carboxylate, a chromium(II) beta-dionate, a chromium(III) alkoxide, a chromium(III) carboxylate, or a chromium(III) beta-dionate. In an embodiment, each carboxylate group of the chromium compound independently can be a $C_2$ to $C_{24}$ carboxylate group, or a $C_4$ to $C_{19}$ carboxylate group, or a $C_5$ to $C_{12}$ carboxylate group. In some embodiments, each alkoxy group of the chromium compound independently can be a $C_1$ to $C_{24}$ alkoxy group, or a $C_4$ to $C_{19}$ alkoxy group, or a $C_5$ to $C_{12}$ alkoxy group. In other embodiments, each aryloxy group of the chromium compound independently can be a $C_6$ to $C_{24}$ aryloxy group, or a $C_6$ to $C_{19}$ aryloxy group, or a $C_6$ to $C_{12}$ aryloxy group. In yet other embodiments, each beta-dionate group of the chromium compound independently can be a $C_5$ to $C_{24}$ beta-dionate group, or a $C_5$ to $C_{19}$ beta-dionate group, or a $C_5$ to $C_{12}$ beta-dionate group. Chromium carboxylates are particularly useful transition metal compounds for some catalyst systems described herein. Thus, in one aspect, the catalyst systems described herein can use a chromium carboxylate composition in which the carboxylate is a $C_2$ to $C_{24}$ monocarboxylate, or a $C_4$ to $C_{19}$ monocarboxylate, or a $C_5$ to $C_{12}$ monocarboxylate.

In an embodiment, each carboxylate group of the chromium carboxylate independently can be an acetate, a propionate, a butyrate, a pentanoate, a hexanoate, a heptanoate, an octanoate, a nonanoate, a decanoate, an undecanoate, a dodecanoate, a tridecanoate, a tetradecanoate, a pentadecanoate, a hexadecanoate, a heptadecanoate, or an octadecanoate; alternatively, a pentanoate, a hexanoate, a heptanoate, a octanoate, a nonanoate, a decanoate, a undecanoate, or a dodecanoate. In some embodiments, each carboxylate group of the chromium carboxylate independently can be acetate, propionate, n-butyrate, isobutyrate, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, laurate (n-dodecanoate), or stearate (n-octadecanoate); alternatively, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate).

In an aspect and in any embodiment, the transition metal compound for the catalyst system systems described herein can comprise, consist essentially of, or can be, a chromium(II) carboxylate or a chromium(III) carboxylate. Exemplary chromium(II) carboxylates can comprise, consist essentially of, or can be, chromium(II) acetate, chromium(II) propionate, chromium(II) butyrate, chromium(II) isobutyrate, chromium(II) neopentanoate, chromium(II) oxalate, chromium(II) octanoate, chromium(II) 2-ethylhexanoate, chromium(II) laurate, or chromium(II) stearate; alternatively, chromium(II) acetate, chromium(II) propionate, chromium(II) butyrate, chromium(II) isobutyrate, chromium(II) neopentanoate, chromium(II) octanoate, chromium(II) 2-ethylhexanoate, chromium(II) laurate, or chromium(II) stearate. In an aspect and in any embodiment, the transition metal compound utilized in the catalyst system can comprise, consist essentially of, or can be, chromium(III) acetate, chromium(III) propionate, chromium(III) butyrate, chromium(III) isobutyrate, chromium(III) neopentanoate, chromium(III) oxalate, chromium(III) octanoate, chromium(III) 2-ethylhexanoate, chromium(III) 2,2,6,6,-tetramethylheptanedionate, chromium(III) naphthenate, chromium(III) laurate, or chromium(III) stearate.

In an embodiment, the heteroatomic ligand (whether it is a separate component of the catalyst system or is a ligand complexed to the transition metal or chromium compound of the catalyst system) can comprise, consist essentially of, or can be, an amine, amide, or imide compound. In one or more embodiments, the heteroatomic ligand (whether it is a separate component of the catalyst system or is a ligand complexed to the transition metal or chromium compound of the catalyst system) can comprise, consist essentially of, or can be, a pyrrole compound, a diphosphinoaminyl compound, a $N^2$-phosphinylamidine compounds, a $N^2$-phosphinylformadine compounds, a phosphinyl guanidine compound or any combination thereof. In some embodiments, the heteroatomic ligand (whether it is a separate component of the catalyst system or is a ligand complexed to the transition metal or chromium compound of the catalyst system) can comprise, consist essentially of, or can be, a pyrrole compound; alternatively, a diphosphinoaminyl compound; alternatively, a $N^2$-phosphinylamidine compounds; alternatively, a $N^2$-phosphinylformadine compound; or alternatively, a phosphinyl guanidine compound.

In an embodiment, the amine compound can be a $C_2$ to $C_{30}$ amine; alternatively, a $C_2$ to $C_{20}$ amine; alternatively, $C_2$ to $C_{15}$ amine; or alternatively, a $C_2$ to $C_{10}$ amine. In an embodiment, the amine compound can be a $C_3$ to $C_{30}$ amide; alternatively, a $C_3$ to $C_{20}$ amide; alternatively, $C_3$ to $C_{15}$ amide; or alternatively, a $C_3$ to $C_{10}$ amide. In an embodiment, the amine compound can be a $C_4$ to $C_{30}$ amide; alternatively, a $C_4$ to $C_{20}$ amide; alternatively, $C_4$ to $C_{15}$ amide; or alternatively, a $C_4$ to $C_{10}$ amide.

In an aspect, the pyrrole compound (also called the "pyrrole") which can be utilized in the catalyst systems described herein can comprise any pyrrole compound that can form a transition metal pyrrolide complex (e.g., chromium pyrrolide complex). As used in this disclosure, the term "pyrrole compound" refers to pyrrole ($C_5H_5N$), derivatives of pyrrole (e.g., indole), substituted pyrroles, as well as metal pyrrolide compounds. A pyrrole compound is defined as a compound comprising a 5-membered, nitrogen-containing heterocycle, such as, for example, pyrrole, derivatives of pyrrole, and mixtures thereof. Broadly, the pyrrole compound can be pyrrole or any heteroleptic or homoleptic metal complex or salt containing a pyrrolide radical or ligand. Generally, the pyrrole compound can be a $C_4$ to $C_{30}$ pyrrole; alternatively, a $C_4$ to $C_{20}$ pyrrole; alternatively, $C_4$ to $C_{15}$ pyrrole; or alternatively, a $C_4$ to $C_{10}$ pyrrole.

In an aspect, the pyrrole compound which can be utilized in the catalyst systems described herein can have Formula P1 or Formula I1. In an embodiment, the pyrrole compound which can be utilized in the catalyst systems described herein can have Formula P1; or alternatively Formula I1.

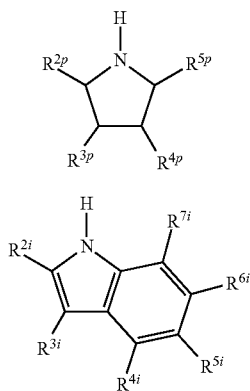

In an aspect, $R^{2p}$, $R^{3p}$, $R^{4p}$, and $R^{5p}$ of Formula P1 and $R^{2i}$, $R^{3i}$, $R^{4i}$, $R^{5i}$, $R^{6i}$, and $R^{7i}$ of Formula I1 independently can be a hydrogen, a $C_1$ to $C_{18}$ organyl group, or a $C_3$ to $C_{60}$ silyl group; alternatively, hydrogen, a $C_1$ to $C_{15}$ organyl group, or a $C_3$ to $C_{45}$ silyl group; alternatively, hydrogen, a $C_1$ to $C_{10}$ organyl group, or a $C_3$ to $C_{30}$ silyl group; alternatively, hydrogen, a $C_1$ to $C_5$ organyl group, or a $C_3$ to $C_{15}$ silyl group; alternatively, hydrogen or a $C_1$ to $C_{18}$ organyl group; alternatively, hydrogen or a $C_1$ to $C_{15}$ organyl group; alternatively, hydrogen or a $C_1$ to $C_{10}$ organyl group; or alternatively, hydrogen or a $C_1$ to $C_5$ organyl group. In an embodiment, $R^{2p}$, $R^{3p}$, $R^{4p}$, and $R^{5p}$ of Formula P1 and $R^{2i}$, $R^{3i}$, $R^{4i}$, $R^{5i}$, $R^{6i}$, and $R^{7i}$ of Formula I1 independently can be a hydrogen, a $C_1$ to $C_{18}$ hydrocarbyl group, or a $C_3$ to $C_{60}$ silyl group; alternatively, hydrogen, a $C_1$ to $C_{15}$ hydrocarbyl group, or a $C_3$ to $C_{45}$ silyl group; alternatively, hydrogen, a $C_1$ to $C_{10}$ hydrocarbyl group, or a $C_3$ to $C_{35}$ silyl group; alternatively, hydrogen, a $C_1$ to $C_5$ hydrocarbyl group, or a $C_3$ to $C_{15}$ silyl group; alternatively, hydrogen or a $C_1$ to $C_{18}$ hydrocarbyl group; alternatively, hydrogen or a $C_1$ to $C_{15}$ hydrocarbyl group; alternatively, hydrogen or a $C_1$ to $C_{10}$ hydrocarbyl group; or alternatively, hydrogen or a $C_1$ to $C_5$ hydrocarbyl group.

In an embodiment, the pyrrole compound which can be utilized in the catalyst systems described herein can comprise, can consist essentially of, or can be, individually or in any combination, pyrrole, 2,5-dimethylpyrrole, 2-methyl-5-ethylpyrrole, 2-methyl-5-propylpyrrole, 2,5-diethylpyrrole, 3,4-dimethylpyrrole, 2,5-di-n-propylpyrrole, 2,5-di-n-butylpyrrole, 2,5-di-n-pentylpyrrole, 2,5-di-n-hexylpyrrole, 2,5-di-n-heptylpyrrole, 2,5-di-n-octylpyrrole, 2,5-dibenzylpyrrole, 2,4-dimethyl-3-ethylpyrrole, 2,3,5-triethylpyrrole, 2,3,5-tri-n-butylpyrrrole, 2,3,5-tri-n-pentylpyrrrole, 2,3,5-tri-n-hexylpyrrrole, 2,3,5-tri-n-heptylpyrrole, 2,3,5-tri-n-octylpyrrrole, 2,3,4,5-tetraethylpyrrole, 2,3,4,5-tetra-n-butylpyrrole, 2,3,4,5-tetra-n-hexylpyrrole, 2,5-bis(2',2',2'-trifluoroethyl)pyrrole, 2,5-bis(2'-methoxymethyl)pyrrole, 2-methyl-4-isopropylpyrrole, 2-ethyl-4-isopropylpyrrole, 2-methyl-4-sec-butylpyrrole, 2-ethyl-4-sec-butylpyrrole, 2-methyl-4-isobutylpyrrole, 2-ethyl-4-isobutylpyrrole, 2-methyl-4-t-butylpyrrole, 2-ethyl-4-t-butylpyrrole, 2-methyl-4-neo-pentylpyrrole, 2-ethyl-4-neopentylpyrrole, 3,4-diisopropylpyrrole, 3,4-di-sec-butylpyrrole, 3,4-di-isobutylpyrrole, 3,4-di-t-butylpyrrole, 3,4-di-neo-pentylpropylpyrrole, tetrahydroindole, dipyrrolylmethane, indole, 3,4-dichloropyrrole, 2,3,4,5-tetrachloropyrrole, pyrrole-2-carboxylic acid, 2-acetylpyrrole, pyrrole-2-carboxaldehyde, 3-acetyl-2,4-dimethylpyrrole, ethyl-2,4-dimethyl-5-(ethoxycarbonyl)-3-pyrrole-proprionate, or ethyl-3,5-dimethyl-2-pyrrolecarboxylate. In some embodiments, pyrrole compounds that can be used in the catalyst system comprise, but are not limited to pyrrole-2-carboxylic acid, 2-acetylpyrrole, pyrrole-2-carboxaldehyde, tetrahydroindole, 2,5-dimethylpyrrole, 2,4-dimethyl-3-ethylpyrrole, 3-acetyl-2,4-dimethylpyrrole, ethyl-2,4-dimethyl-5-(ethoxycarbonyl)-3-pyrrole-proprionate, ethyl-3,5-dimethyl-2-pyrrolecarboxylate, 3,4-dichloropyrrole, 2,3,4,5-tetrachloropyrrole, 2-acetylpyrrole, pyrazole, pyrrolidine, indole, and dipyrrolylmethane, and mixtures thereof. In other embodiments, the pyrrole compound which can be utilized in the catalyst systems described herein can comprise, can consist essentially of, or can be, individually or in any combination, pyrrole, 2,5-dimethylpyrrole, 2-methyl-5-ethylpyrrole, 2-methyl-5-propylpyrrole, or 2,5-diethylpyrrole; alternatively, pyrrole; alternatively, 2,5-dimethylpyrrole; alternatively, 2-methyl-5-ethylpyrrole; alternatively, 2-methyl-5-propylpyrrole; or alternatively, 2,5-diethylpyrrole.

In an embodiment, the pyrrole compound which can be utilized in the catalyst systems described herein can comprise a metal pyrrolide, such as an alkyl metal pyrrolide. In some embodiments, the pyrrole compound which can be utilized in the catalyst systems described herein can comprise, individually or in any combination, a dialkylaluminum pyrrolide of any pyrrole provided herein. Alkyl groups have been described herein (e.g., as alkyl group for the metal alkyl) and these alkyl groups can be utilized to further describe the alkyl metal pyrrolide and/or the dialkylaluminum pyrrolide which can be utilized as the pyrrole compound which can be utilized in the catalyst systems described herein. In other embodiments, the pyrrole compound which can be utilized in the catalyst systems described herein can comprise, individually or in any combination, diethylaluminum 2,5-dimethylpyrrolide, ethylaluminum di(2,5-dimethylpyrrolide), or aluminum tri(2,5-dimethylpyrrolide).

In an embodiment, the heteroatomic ligand can be a diphosphinylaminyl compound. A diphosphinylaminyl compound is a compound having a moiety characterized by having a P—N—P (phosphorus-nitrogen-phosphorus) linkage. The moiety having the P—N—P linkage can hereafter be referred to a PNP moiety or as a diphosphino aminyl moiety. The heteroatomic ligand comprising the diphosphino aminyl moiety can be referred to as a PNP ligand, a diphosphino aminyl ligand, or a diphosphino aminyl compound.

In an embodiment, the heteroatomic ligand can comprise a diphosphino aminyl moiety having Structure PNP1:

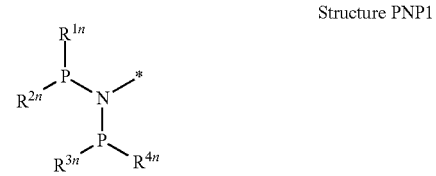

Structure PNP1 wherein $R^{1n}$, $R^{2n}$, $R^{3n}$, and $R^{4n}$ can be any group described herein and the undesignated aminyl nitrogen valence (*) represents the remainder of the heteroatomic ligand. In an embodiment, $R^{1n}$, $R^{2n}$, $R^{3n}$, and $R^{4n}$ can each be different. In some embodiments, $R^{1n}$, $R^{2n}$, $R^{3n}$, and $R^{4n}$ can each be the same. In other embodiments, $R^{1n}$ and $R^{2n}$ can be the same and $R^{3n}$ and $R^{4n}$ can be the same but different from $R^{1n}$ and $R^{2n}$. In yet other embodiments, $R^{1n}$ and $R^{3n}$ can be the same and $R^{2n}$ and $R^{4n}$ can be the same but different from $R^{1n}$ and $R^{3n}$.

In an embodiment, $R^{1n}$, $R^{2n}$, $R^{3n}$, and $R^{4n}$ independently can be an organyl group; alternatively, an organyl group comprising inert functional groups; or alternatively, a hydrocarbyl group. In an embodiment, the organyl group which can be utilized as $R^{1n}$, $R^{2n}$, $R^{3n}$, and $R^{4n}$ can be a $C_1$ to $C_{30}$ organyl group; alternatively, a $C_1$ to $C_{20}$ organyl group; alternatively, a $C_1$ to $C_{15}$ organyl group; alternatively, a $C_1$ to $C_{10}$ organyl group; or alternatively, a $C_1$ to $C_5$ organyl group. In an embodiment, the organyl group comprising inert functional groups which can be utilized as $R^{1n}$, $R^{2n}$, $R^{3n}$, and $R^{4n}$ can be a $C_1$ to $C_{30}$ organyl group comprising inert functional groups; alternatively, a $C_1$ to $C_{20}$ organyl group comprising inert functional groups; alternatively, a $C_1$ to $C_{15}$ organyl group comprising inert functional groups; alternatively, a $C_1$ to $C_{10}$ organyl group comprising inert functional groups; or alternatively, a $C_1$ to $C_5$ organyl group comprising inert functional groups. In an embodiment, the hydrocarbyl group which can be utilized as $R^{1n}$, $R^{2n}$, $R^{3n}$, and $R^{4n}$ can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_5$ hydrocarbyl group. In further embodiments, two or more of $R^{1n}$, $R^{2n}$, $R^{3n}$, and $R^{4n}$ can be joined to form a ring or a ring system.

In an embodiment, the heteroatomic ligand can be compound having a $N^2$-phosphinyl formamidine group. Generally, a formamidine group is a group having the general structure

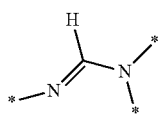

Within the formamidine group the nitrogen participating in a double bond with the central carbon atom is referred to as the $N^1$ nitrogen and the nitrogen atom participating in a single bond with the central carbon atom is referred to as the $N^2$ nitrogen. Similarly, the groups attached to the $N^1$ and $N^2$ nitrogen atoms are referred to as the $N^1$ group and $N^2$ group respectively. An $N^2$-phosphinyl formamidine group has the general structure

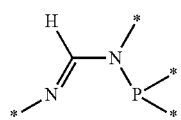

Within the $N^2$-phosphinyl formamidine group the $N^1$ and $N^2$ nitrogen atoms and $N^1$ and $N^2$ groups have the same meaning as described for the formamidine group. Consequently, an $N^2$-phosphinyl formamidine group has the phosphinyl group is attached to the $N^2$ nitrogen atom.

In an embodiment, the heteroatomic ligand can be an $N^2$-phosphinyl formamidine compound having Structure NPF1. In some embodiments, the transition metal compound complexed to an $N^2$-phosphinylformamidine compound can have Structure NPFMC1. In an embodiment, the transition metal compound complexed to an $N^2$-phosphinylformamidine compound can be a chromium compound complexed to an $N^2$-phosphinylformamidine compound having Structure NPFCr1.

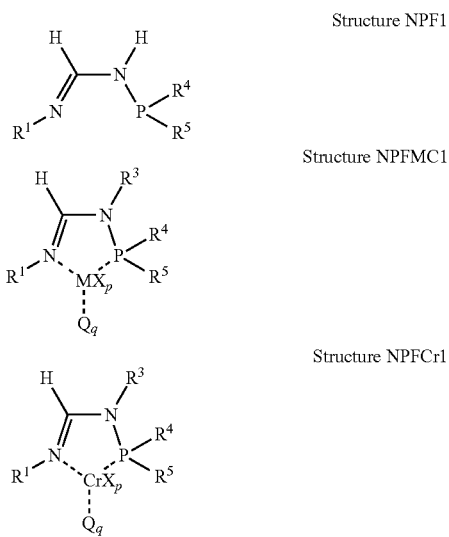

$R^1$, $R^3$, $R^4$, and $R^5$ within the $N^2$-phosphinyl formamidine compound having Structure NPF1, $N^2$-phosphinyl formamidine transition metal complex having Structure NPFMC1, and the $N^2$-phosphinyl formamidine chromium complex having Structure NPFCr1 are independently described herein and can be utilized without limitation to further describe the $N^2$-phosphinyl formamidine compound having Structure NPF1, the $N^2$-phosphinyl formamidine transition metal complex having Structure NPFMC1, and the $N^2$-phosphinyl formamidine chromium complex having Structure NPFCr1. $MX_p$ represents the transition metal compound of the $N^2$-phosphinyl formamidine transition metal complex having Structure NPFMC1. $CrX_p$ represents the chromium compound of the $N^2$-phosphinyl formamidine chromium complex having Structure NPFCr1. Q represents an optional neutral ligand within the $N^2$-phosphinyl formamidine transition metal complex having Structure NPFMC1 and the $N^2$-phosphinyl formamidine chromium complex having Structure NPFCr1, while q represents the number of optional neutral ligands present. $MX_p$, $CrX_p$, Q, and q are independently described herein and can be utilized without limitation to further describe the $N^2$-phosphinyl formamidine transition metal complex having Structure NPFMC1 and the $N^2$-phosphinyl formamidine chromium complex having Structure NPFCr1. Additionally, $MX_p$, $CrX_p$, Q, and q can be combined with the independently described $R^1$, $R^3$, $R^4$, and $R^5$ to further describe the $N^2$-phosphinyl formamidine transition metal complex having Structure NPFMC1 and the $N^2$-phosphinyl formamidine chromium complex having Structure NPFCr1.

In an embodiment, the heteroatomic ligand can be compound having a $N^2$-phosphinyl amidine group. Generally, an amidine group is a group having the general structure

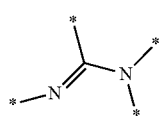 [SMILES: */N=C(\*)N(*)*]

Within the amidine group the nitrogen participating in a double bond with the central carbon atom is referred to as the $N^1$ nitrogen and the nitrogen atom participating in a single bond with the central carbon atom is referred to as the $N^2$ nitrogen. Similarly, the groups attached to the $N^1$ and $N^2$ nitrogen atoms are referred to as the $N^1$ group and $N^2$ group respectively. An $N^2$-phosphinyl amidine group has the general structure

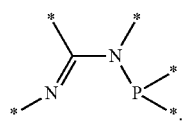

Within the $N^2$-phosphinyl amidine group the $N^1$ and $N^2$ nitrogen atoms and $N^1$ and $N^2$ groups have the same meaning as described for the amidine group. Consequently, an $N^2$-phosphinyl amidine group has the phosphinyl group is attached to the $N^2$ nitrogen atom. Within the amidine group and $N^2$-phosphinyl amidine group the carbon atom between the two nitrogen atoms is the central carbon atom and any substituent attached to it is referred to as the central carbon group. For the purpose of this disclosure and claims, a compound having a pyridine group with a 2-amine group (or its analogues—e.g., a pyrimidine ring, an imidazole ring, a compound having 2-aminopyridine group, and the like) or having a 2-phosphinylamine group is not considered to constitute an amidine group or $N^2$-phosphinyl amidine group, respectively.

In an aspect, the $N^2$-phosphinyl amidine metal complex can have Structure NPAMC1.

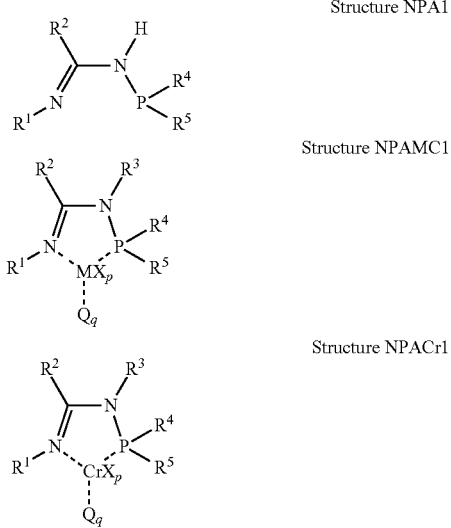

Structure NPA1

Structure NPAMC1

Structure NPACr1

$R^1$, $R^2$, $R^3$, $R^4$, and $R^5$ within the $N^2$-phosphinyl amidine compound having Structure NPA1, $N^2$-phosphinyl amidine transition metal complex having Structure NPAMC1, and the $N^2$-phosphinyl amidine chromium complex having Structure NPACr1 are independently described herein and can be utilized without limitation to further describe the $N^2$-phosphinyl amidine compound having Structure NPA1, the $N^2$-phosphinyl amidine transition metal complex having Structure NPAMC1, and the $N^2$-phosphinyl amidine chromium complex having Structure NPACr1. $MX_p$ represents the transition metal compound of the $N^2$-phosphinyl amidine transition metal complex having Structure NPAMC1. $CrX_p$ represents the chromium compound of the $N^2$-phosphinyl amidine chromium complex having Structure NPACr1. Q represents an optional neutral ligand of the $N^2$-phosphinyl amidine transition metal complex having Structure NPAMC1 and the $N^2$-phosphinyl amidine chromium complex having Structure NPACr1, while q represents the number of optional neutral ligands present. $MX_p$, $CrX_p$, Q, and q are independently described herein and can be utilized without limitation to further describe the $N^2$-phosphinyl amidine transition metal complex having Structure NPAMC1 and the $N^2$-phosphinyl amidine chromium complex having Structure NPACr1. Additionally, $MX_p$, $CrX_p$, Q, and q can be combined with the independently described $R^1$, $R^2$, $R^3$, $R^4$, and $R^5$ to further describe the $N^2$-phosphinyl amidine transition metal complex having Structure NPAMC1 and the $N^2$-phosphinyl amidine chromium complex having Structure NPACr1.

In an embodiment, the heteroatomic ligand can be compound having a $N^2$-phosphinyl guanidine group. Generally, a guanidine group, is a group having the general structure

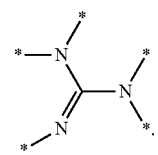

Within the guanidine core, the nitrogen participating in a double bond with the central carbon atom is referred to as the $N^1$ nitrogen and the two nitrogen atoms participating in a single bond with the central carbon atom are referred to as the $N^2$ nitrogen and the $N^3$ nitrogen. Similarly, the groups attached to the $N^1$, $N^2$ and $N^3$ nitrogen atoms are referred to as the $N^1$ group, $N^2$ group, and $N^3$ group respectively. An $N^2$-phosphinyl guanidine group, such as those found in a ligand of the $N^2$-phosphinyl guanidine complexes described herein, has the general structure

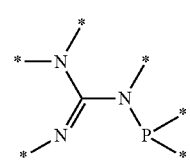 [SMILES: */N=C(\N(*)*)N(*)P(*)*]

Within an $N^2$-phosphinyl guanidine group, the nitrogen participating in a double bond with the central carbon atom of the guanidine core is referred to as the $N^1$ nitrogen, the nitrogen atom participating in a single bond with the central carbon atom of the guanidine core and a bond with the phosphorus atom of the phosphinyl group is referred to as the $N^2$ nitrogen, and the remaining nitrogen atom participating in a single bond with the central carbon atom of the guanidine core is referred to as the $N^3$ nitrogen. It should be noted that a guanidine core or an $N^2$-phosphinyl guanidine group can be a portion of a larger group (or compound) which does not contain guanidine in it name. For example, while the compound 7-dimethylphosphinylimidazo[1,2-a]imidazole could be classified as a compound having an imidazo[1,2-a]imidazole core (or a compound having a phosphinylimidazo[1,2-a]imidazole group), 7-dimethylphosphinylimidazo[1,2-a]imidazole would still be classified as a compound having a guanidine core (or as a compound having an $N^2$-phosphinyl guanidine group) since it contains the defined general structure of the guanidine core (or the $N^2$-phosphinyl guanidine group).

In an embodiment, the $N^2$-phosphinyl guanidine compound can have Structure Gu1, Gu2, Gu3, Gu4, or Gu5: alternatively, Structure Gu1; alternatively, Structure Gu2; alternatively, Structure Gu3; alternatively, Gu4; or alternatively, Gu5. In an embodiment, the $N^2$-phosphinyl guanidine transition metal complex can have Structure GuMC1, GuMC2, GuMC3, GuMC4, or GuMC5: alternatively, Structure GuMC1; alternatively, Structure GuMC2; alternatively, Structure GuMC3; alternatively, GuMC4; or alternatively, GuMC5. In an embodiment, the $N^2$-phosphinyl guanidine chromium complex can have Structure GuCr1, GuCr2, GuCr3, GuCr4, or GuCr5: alternatively, Structure GuCr1; alternatively, Structure GuCr2; alternatively, Structure GuCr3; alternatively, GuCr4; or alternatively, GuCr5.

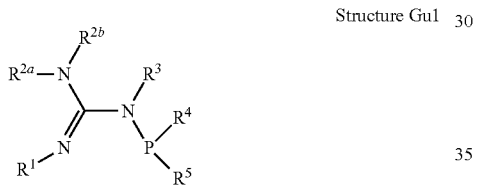

Structure Gu1

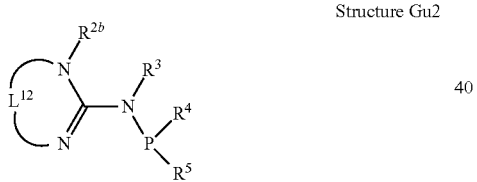

Structure Gu2

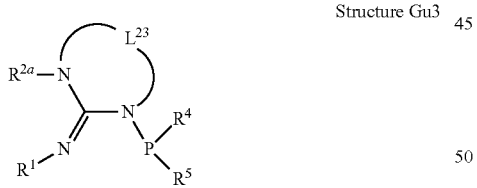

Structure Gu3

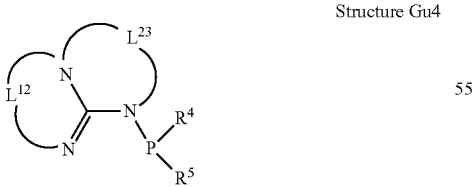

Structure Gu4

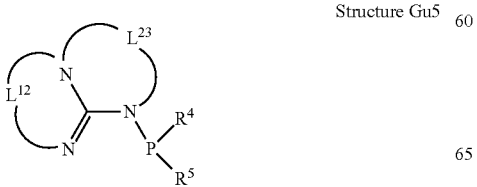

Structure Gu5

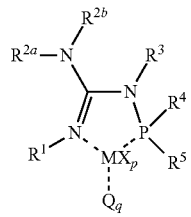

Structure GuMC1

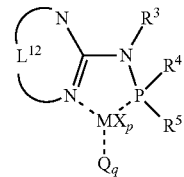

Structure GuMC2

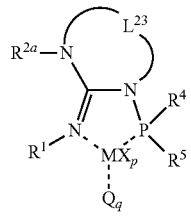

Structure GuMC3

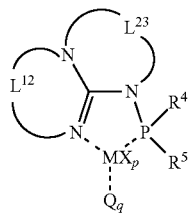

Structure GuMC4

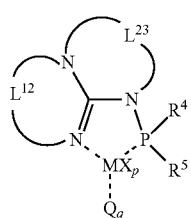

Structure GuMC5

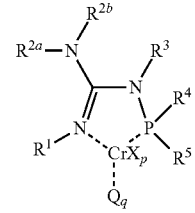

Structure GuCr1

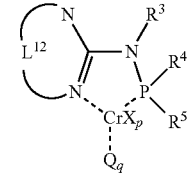

Structure GuCr2

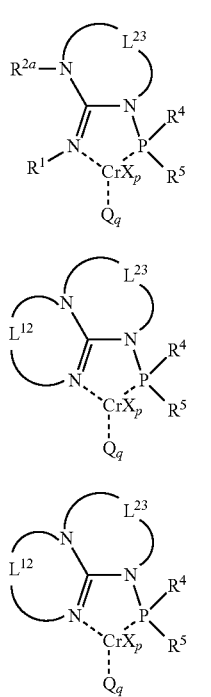

Structure GuCr3

Structure GuCr4

Structure GuCr5

$R^1$, $R^{2a}$, $R^{2b}$, $R^4$, $R^5$, $L^{12}$, and $L^{22}$, within the appropriate i) $N^2$-phosphinyl guanidine compound Structures Gu1, Gu2, Gu3, Gu4, and/or Gu5, ii) $N^2$-phosphinyl guanidine transition metal complex Structures GuMC1, GuMC2, GuMC3, GuMC4, and/or GuMC5, and/or iii) $N^2$-phosphinyl guanidine chromium complex Structures GuCr1, GuCr2, GuCr3, GuCr4, and/or GuCr5 are independently described herein and can be utilized without limitation to further describe the appropriate i) $N^2$-phosphinyl guanidine compound Structures Gu1, Gu2, Gu3, Gu4, and/or Gu5, ii) $N^2$-phosphinyl guanidine transition metal complex Structures GuMC1, GuMC2, GuMC3, GuMC4, and/or GuMC5, and/or iii) $N^2$-phosphinyl guanidine chromium complex Structures GuCr1, GuCr2, GuCr3, GuCr4, and/or GuCr5. $MX_p$ within the $N^2$-phosphinyl guanidine transition metal complexes having $N^2$-phosphinyl guanidine transition metal complex Structures GuMC1, GuMC2, GuMC3, GuMC4, and GuMC5 represents the transition metal compound of the $N^2$-phosphinyl guanidine transition metal complexes. $CrX_p$ within the $N^2$-phosphinyl guanidine chromium complex Structures GuCr1, GuCr2, GuCr3, GuCr4, and/or GuCr5 represents the chromium compound of the $N^2$-phosphinyl guanidine chromium complexes. Q represents an optional neutral ligand of i) the $N^2$-phosphinyl guanidine transition metal complex Structures GuMC1, GuMC2, GuMC3, GuMC4, and GuMC5, and iii) the $N^2$-phosphinyl guanidine chromium complex Structures GuCr1, GuCr2, GuCr3, GuCr4, and/or GuCr5, while q represents the number of optional neutral ligands present. $MX_p$, $CrX_p$, Q, and q are independently described herein and can be utilized without limitation to further describe i) the $N^2$-phosphinyl guanidine transition metal complex Structures GuMC1, GuMC2, GuMC3, GuMC4, and GuMC5, and iii) the $N^2$-phosphinyl guanidine chromium complex Structures GuCr1, GuCr2, GuCr3, GuCr4, and/or GuCr5. Additionally, $MX_p$, $CrX_p$, Q, and q can be combined with the independently described $R^1$, $R^2$, $R^3$, $R^4$, and $R^5$ to further described i) the $N^2$-phosphinyl guanidine transition metal complex Structures GuMC1, GuMC2, GuMC3, GuMC4, and GuMC5, and iii) the $N^2$-phosphinyl guanidine chromium complex Structures GuCr1, GuCr2, GuCr3, GuCr4, and/or GuCr5.

Generally, $R^1$ for the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes which have an $R^1$ group can be an organyl group; alternatively, an organyl group consisting essentially of inert functional groups; or alternatively, a hydrocarbyl group. In an embodiment, the $R^1$ organyl group for the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes which have an $R^1$ group can be a $C_1$ to $C_{30}$ organyl group; alternatively, a $C_1$ to $C_{20}$ organyl group; alternatively, a $C_1$ to $C_{15}$ organyl group; alternatively, a $C_1$ to $C_{10}$ organyl group; or alternatively, a $C_1$ to $C_5$ organyl group. In an embodiment, the $R^1$ organyl group consisting essentially of inert functional groups for the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes which have an $R^1$ group can be a $C_1$ to $C_{30}$ organyl group consisting essentially of inert functional groups; alternatively, a $C_1$ to $C_{20}$ organyl group consisting essentially of inert functional groups; alternatively, a $C_1$ to $C_{15}$ organyl group consisting essentially of inert functional groups; alternatively, a $C_1$ to $C_{10}$ organyl group consisting essentially of inert functional groups; or alternatively, a $C_1$ to $C_5$ organyl group consisting essentially of inert functional groups. In an embodiment, the $R^1$ hydrocarbyl group for the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes which have an $R^1$ group can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; alternatively, a $C_1$ to $C_5$ hydrocarbyl group; alternatively, a $C_1$ to $C_{30}$ alkyl group; alternatively, a $C_1$ to $C_{20}$ alkyl group; alternatively, a $C_1$ to $C_{15}$ alkyl group; or alternatively, a $C_1$ to $C_{10}$ alkyl group; or alternatively, a $C_1$ to $C_5$ alkyl group. In yet other embodiments, the $R^1$ group for the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes which have an $R^1$ group can be a $C_3$ to $C_{30}$ aromatic group; alternatively, a $C_3$ to $C_{20}$ aromatic group; alternatively, a $C_3$ to $C_{15}$ aromatic group; or alternatively, a $C_3$ to $C_{10}$ aromatic group. In further embodiments, the $R^1$ group for the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes which have an $R^1$ group can be a phenyl group or a $C_6$ to $C_{30}$ substituted phenyl group; alternatively, a phenyl group or a $C_6$ to $C_{20}$ substituted phenyl group; alternatively, a phenyl group or a $C_6$ to $C_{15}$ substituted phenyl group; or alternatively, a phenyl group or a $C_6$ to $C_{10}$ substituted phenyl group. General substituent groups are provided herein and these general substituent groups can be utilized to further describe the substituted phenyl groups which can be utilized as $R^1$ for the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes.

Generally, $R^2$ for the $N^2$-phosphinyl amidine compounds, the $N^2$-phosphinyl amidine transition metal complexes, and the $N^2$-phosphinyl amidine chromium complexes can be an organyl group; alternatively, an organyl group consisting essentially of inert functional groups; or alternatively, a hydrocarbyl group. In an embodiment, $R^2$ for the $N^2$-phosphinyl amidine compounds, the $N^2$-phosphinyl amidine transition metal complexes, and the $N^2$-phosphinyl amidine chromium complexes can be a $C_1$ to $C_{30}$ organyl group; alternatively, a $C_1$ to $C_{20}$ organyl group; alternatively, a $C_1$ to $C_{15}$ organyl group; alternatively, a $C_1$ to $C_{10}$ organyl group; or alternatively, a $C_1$ to $C_5$ organyl group. In an embodiment, $R^2$ for the $N^2$-phosphinyl amidine compounds, the $N^2$-phosphinyl amidine transition metal complexes, and the $N^2$-phosphinyl amidine chromium complexes can be a $C_1$ to $C_{30}$ organyl group consisting essentially of inert functional groups; alternatively, a $C_1$ to $C_{20}$ organyl group consisting essentially of inert functional groups; alternatively, a $C_1$ to $C_{15}$ organyl group consisting essentially of inert functional groups; alternatively, a $C_1$ to $C_{10}$ organyl group consisting essentially of inert functional groups; or alternatively, a $C_1$ to $C_5$ organyl group consisting essentially of inert functional groups. In an embodiment, $R^2$ for the $N^2$-phosphinyl amidine compounds, the $N^2$-phosphinyl amidine transition metal complexes, and the $N^2$-phosphinyl amidine chromium complexes can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; alternatively, a $C_1$ to $C_5$ hydrocarbyl group; alternatively, a $C_1$ to $C_{30}$ alkyl group; alternatively, a $C_1$ to $C_{20}$ alkyl group; alternatively, a $C_1$ to $C_{15}$ alkyl group; or alternatively, a $C_1$ to $C_{10}$ alkyl group; alternatively, a $C_1$ to $C_5$ alkyl group. In yet other embodiments, $R^2$ for the $N^2$-phosphinyl amidine compounds, the $N^2$-phosphinyl amidine transition metal complexes, and the $N^2$-phosphinyl amidine chromium complexes can be a $C_3$ to $C_{30}$ aromatic group; alternatively, a $C_3$ to $C_{20}$ aromatic group; alternatively, a $C_3$ to $C_{15}$ aromatic group; or alternatively, a $C_3$ to $C_{10}$ aromatic group. In yet other embodiments, $R^2$ for the $N^2$-phosphinyl amidine compounds, the $N^2$-phosphinyl amidine transition metal complexes, and the $N^2$-phosphinyl amidine chromium complexes can be a phenyl group or a $C_6$ to $C_{30}$ substituted phenyl group; alternatively, a phenyl group or a $C_6$ to $C_{20}$ substituted phenyl group; alternatively, a phenyl group or a $C_6$ to $C_{15}$ substituted phenyl group; or alternatively, phenyl group or a $C_6$ to $C_{10}$ substituted phenyl group. In further embodiments, $R^2$ for the $N^2$-phosphinyl amidine compounds, the $N^2$-phosphinyl amidine transition metal complexes, and the $N^2$-phosphinyl amidine chromium complexes can be a benzyl group or a $C_6$ to $C_{30}$ substituted benzyl group; alternatively, a benzyl group or a $C_6$ to $C_{20}$ substituted benzyl group; alternatively, a benzyl group or a $C_6$ to $C_{15}$ substituted benzyl group; or alternatively, a benzyl group or a $C_6$ to $C_{10}$ substituted benzyl group. General substituent groups are provided herein and these general substituent groups can be utilized to further describe the substituted phenyl groups and/or substituted benzyl groups which can be utilized as $R^2$ for the $N^2$-phosphinyl amidine compounds, the $N^2$-phosphinyl amidine transition metal complexes, and the $N^2$-phosphinyl amidine chromium complexes.

Generally, $R^{2a}$ and/or $R^{2b}$ for the $N^2$-phosphinyl guanidine compounds, the $N^2$-phosphinyl guanidine transition metal complexes, and/or the $N^2$-phosphinyl guanidine chromium complexes, which have an $R^{2a}$ and/or $R^{2b}$ group independently can be hydrogen or an organyl group; alternatively, hydrogen; or alternatively, an organyl group. In another aspect, $R^{2a}$ and/or $R^{2b}$ for the $N^2$-phosphinyl guanidine compounds, the $N^2$-phosphinyl guanidine transition metal complexes, and/or the $N^2$-phosphinyl guanidine chromium complexes, which have an $R^{2a}$ and/or $R^{2b}$ group independently can be hydrogen or an organyl group consisting essentially of inert functional groups; alternatively, hydrogen; or alternatively, an organyl group consisting essentially of inert functional groups. In an aspect, $R^{2a}$ and/or $R^{2b}$ for the $N^2$-phosphinyl guanidine compounds, the $N^2$-phosphinyl guanidine transition metal complexes, and/or the $N^2$-phosphinyl guanidine chromium complexes, which have an $R^{2a}$ and/or $R^{2b}$ group independently can be hydrogen or a hydrocarbyl group; alternatively, hydrogen; or alternatively, a hydrocarbyl group. In an embodiment, $R^{2a}$ and $R^{2b}$ the organyl group for the $N^2$-phosphinyl guanidine compounds, the $N^2$-phosphinyl guanidine transition metal complexes, and/or the $N^2$-phosphinyl guanidine chromium complexes, which have an $R^{2a}$ and/or $R^{2b}$ organyl group independently can be a $C_1$ to $C_{30}$ organyl group; alternatively, a $C_1$ to $C_{20}$ organyl group; alternatively, a $C_1$ to $C_{15}$ organyl group; alternatively, a $C_1$ to $C_{10}$ organyl group; or alternatively, a $C_1$ to $C_5$ organyl group. In some embodiments, the organyl group consisting of inert functional group $R^{2a}$ and/or $R^{2b}$ the organyl group consisting of inert functional group for the $N^2$-phosphinyl guanidine compounds, the $N^2$-phosphinyl guanidine transition metal complexes, and/or the $N^2$-phosphinyl guanidine chromium complexes, which have an $R^{2a}$ and/or $R^{2b}$ organyl consisting of inert functional groups independently can be a $C_1$ to $C_{30}$ organyl group consisting essentially of inert functional groups; alternatively, a $C_1$ to $C_{20}$ organyl group consisting essentially of inert functional groups; alternatively, a $C_1$ to $C_{15}$ organyl group consisting essentially of inert functional groups; alternatively, a $C_1$ to $C_{10}$ organyl group consisting essentially of inert functional groups; or alternatively, a $C_1$ to $C_5$ organyl group consisting essentially of inert functional groups. In other embodiments, $R^{2a}$ and/or $R^{2b}$ hydrocarbyl group for the $N^2$-phosphinyl guanidine compounds, the $N^2$-phosphinyl guanidine transition metal complexes, and/or the $N^2$-phosphinyl guanidine chromium complexes, which have an $R^{2a}$ and/or $R^{2b}$ hydrocarbyl group independently can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; alternatively, a $C_1$ to $C_5$ hydrocarbyl group; alternatively, a $C_1$ to $C_{30}$ alkyl group; alternatively, a $C_1$ to $C_{20}$ alkyl group; alternatively, a $C_1$ to $C_{15}$ alkyl group; or alternatively, a $C_1$ to $C_{10}$ alkyl group; or alternatively, a $C_1$ to $C_5$ alkyl group. In yet other embodiments, $R^{2a}$ and/or $R^{2b}$ for the $N^2$-phosphinyl guanidine compounds, the $N^2$-phosphinyl guanidine transition metal complexes, and/or the $N^2$-phosphinyl guanidine chromium complexes, which have an $R^{2a}$ and/or $R^{2b}$ group independently can be a $C_3$ to $C_{30}$ aromatic group; alternatively, a $C_3$ to $C_{20}$ aromatic group; alternatively, a $C_3$ to $C_{15}$ aromatic group; or alternatively, a $C_3$ to $C_{10}$ aromatic group. In yet other embodiments, $R^{2a}$ and/or $R^{2b}$ for the $N^2$-phosphinyl guanidine compounds, the $N^2$-phosphinyl guanidine transition metal complexes, and/or the $N^2$-phosphinyl guanidine chromium complexes which have an $R^{2a}$ and/or $R^{2b}$ group can be a phenyl group or a $C_6$ to $C_{30}$ substituted phenyl group; alternatively, a phenyl group or a $C_6$ to $C_{20}$ substituted phenyl group; alternatively, a phenyl group or a $C_6$ to $C_{15}$ substituted phenyl group; or alternatively, phenyl group or a $C_6$ to $C_{10}$ substituted phenyl group. General substituent groups are provided herein and these general substituent groups can be utilized to further describe the substituted phenyl groups which can be utilized as $R^{2a}$ and/or $R^{2b}$ for the $N^2$-phosphinyl guanidine compounds, the $N^2$-phosphinyl guanidine transition metal complexes, and/or the $N^2$-phosphinyl guanidine chromium complexes.

In an aspect, $R^1$ and $R^{2a}$ of the $N^2$-phosphinyl guanidine compounds, the $N^2$-phosphinyl guanidine transition metal complexes, and/or the $N^2$-phosphinyl guanidine chromium complexes can be joined to form a group, $L^{12}$, wherein $L^{12}$, the $N^1$ nitrogen atom, and the $N^3$ nitrogen atom can form a ring or a ring system. In another aspect, $R^3$ and $R^{2b}$ of the $N^2$-phosphinyl guanidine compounds, the $N^2$-phosphinyl guanidine transition metal complexes, and/or the $N^2$-phosphinyl guanidine chromium complexes can be joined to form a group, $L^{23}$, wherein $L^{23}$, the $N^2$ nitrogen atom, and the $N^3$ nitrogen atom can form a ring or a ring system. In an embodiment, $L^{12}$ and/or $L^{23}$ for the $N^2$-phosphinyl guanidine compounds, the $N^2$-phosphinyl guanidine transition metal complexes, and/or the $N^2$-phosphinyl guanidine chromium complexes which have an $L^{12}$ group and/or an $L^{23}$ group independently can be an organylene group; alternatively, an organylene group consisting of inert functional groups; or alternatively, a hydrocarbylene group. The organylene group which can be utilized as $L^{12}$ and/or $L^{23}$ of the $N^2$-phosphinyl guanidine compounds, the $N^2$-phosphinyl guanidine transition metal complexes, and/or the $N^2$-phosphinyl guanidine chromium complexes which have an $L^{12}$ group and/or an $L^{23}$ group independently can be a $C_2$ to $C_{20}$ organylene group; alternatively, a $C_2$ to $C_{15}$ organylene group; alternatively, a $C_2$ to $C_{10}$ organylene group; or alternatively, a $C_2$ to $C_5$ organylene group. The organylene group consisting of inert functional groups which can be utilized as $L^{12}$ and/or $L^{23}$ of the $N^2$-phosphinyl guanidine compounds, the $N^2$-phosphinyl guanidine transition metal complexes, and/or the $N^2$-phosphinyl guanidine chromium complexes which have an $L^{12}$ group and/or an $L^{23}$ group can be a $C_2$ to $C_{20}$ organylene group consisting of inert functional groups; alternatively, a $C_2$ to $C_{15}$ organylene group consisting of inert functional groups; alternatively, a $C_2$ to $C_{10}$ organylene group consisting of inert functional groups; or alternatively, a $C_2$ to $C_5$ organylene group consisting of inert functional groups. The hydrocarbylene group which can be utilized as $L^{12}$ and/or $L^{23}$ of the $N^2$-phosphinyl guanidine compounds, the $N^2$-phosphinyl guanidine transition metal complexes, and/or the $N^2$-phosphinyl guanidine chromium complexes which have an $L^{12}$ group and/or an $L^{23}$ group can be a $C_2$ to $C_{20}$ hydrocarbylene group; alternatively, a $C_2$ to $C_{15}$ hydrocarbylene group; alternatively, a $C_2$ to $C_{10}$ hydrocarbylene group; or alternatively, a $C_2$ to $C_5$ hydrocarbylene group.

In an embodiment, $L^{12}$ and/or $L^{23}$ can have any structure provided in Table 1. In some embodiments, $L^{12}$ and/or $L^{23}$ can have Structure 1L, Structure 2L, Structure 3L, Structure 4L or Structure 5L. In some embodiments, $L^{12}$ and/or $L^{23}$ can have Structure 2L or Structure 3L; alternatively, Structure 4L or Structure 5L. In other embodiments, $L^{12}$ and/or $L^{23}$ can have Structure 1L; alternatively, Structure 2L; alternatively, Structure 3L; alternatively, Structure 4L; or alternatively, Structure 5L. In some embodiments, $L^{12}$ and/or $L^{23}$ can have Structure 6L. It should be noted that when $L^{12}$ has Structure 6L the corresponding $R^{2b}$ is null because of the double bond link (depicted as real but can be delocalized through aromatic resonance) with the $N^3$ nitrogen atom of the $N^2$-phosphinyl guanidine metal complex.

TABLE 1

Structures for Linking Groups $L^{12}$ and/or $L^{23}$.

| | |
|---|---|
| —(CR$^{L1}$R$^{L2}$)$_m$— | Structure 1L |
| —CR$^{L3}$R$^{L4}$—CR$^{L5}$R$^{L6}$— | Structure 2L |
| —CR$^{L3}$R$^{L4}$—CR$^{L7}$R$^{L8}$—CR$^{L5}$R$^{L6}$— | Structure 3L |
| —CR$^{11L}$=CR$^{12L}$— | Structure 4L |
| $R^{L23}$, $R^{L26}$, $R^{L24}$, $R^{L25}$ (substituted benzene ring) | Structure 5L |
| =CR$^{27}$—CR$^{28}$=CR$^{29}$— | Structure 6L |

Within the structures of Table 1, the undesignated valencies represent the points at which $L^{12}$ and/or $L^{23}$, when present, attach to the respective nitrogen atoms of the $N^2$-phosphinyl guanidine compound, $N^2$-phosphinyl guanidine transition metal complex, or $N^2$-phosphinyl chromium complex. Generally, m can be an integer ranging from 2 to 5. In further embodiments, m can be 2 or 3; alternatively, m can be 2; or alternatively, m can be 3. $R^{L1}$ and $R^{L2}$ of the linking group having Structure 1L, $R^{L3}$, $R^{L4}$, $R^{L5}$, and $R^{L6}$ of the linking group having Structure 2L, $R^{L3}$, $R^{L4}$, $R^{L5}$, $R^{L6}$, $R^{L7}$, and $R^{L8}$, of the linking group having Structure 3L, $R^{L11}$ and $R^{L12}$ of the linking group having Structure 4L, $R^{L22}$, $R^{L23}$, $R^{L24}$, $R^{L25}$, and $R^{L26}$ of the linking group having Structure 5L, $R^{L27}$, $R^{L28}$, and $R^{L29}$ of the linking group having Structure 6L independently can be a hydrogen or a non-hydrogen substituent group; or alternatively, hydrogen. Non-hydrogen substituent group are independently disclosed herein and can be utilized without limitation to further describe the linking group having Structure 1L, Structure 2L, Structure 3L, Structure 4L, and/or Structure 5L. In an embodiment, $L^{12}$ and/or $L^{23}$ can be an eth-1,2-ylene group (—CH$_2$CH$_2$—), an ethen-1,2-ylene group (—CH=CH—), a prop-1,3-ylene group (—CH$_2$CH$_2$CH$_2$—), a 1-methylethen-1,2-ylene group (—C(CH$_3$)=CH—), a but-1,3-ylene group (—CH$_2$CH$_2$CH(CH$_3$)—), a 3-methylbut-1,3-ylene group (—CH$_2$CH$_2$C(CH$_3$)$_2$—), or a phen-1,2-ylene group. In some non-limiting embodiments, L$^{12}$ and/or L$^{23}$ be an eth-1,2-ylene group (—CH$_2$CH$_2$—), a prop-1,3-ylene group (—CH$_2$CH$_2$CH$_2$—), a 1-methylethen-1,2-ylene group (—C(CH$_3$)=CH—), a but-1,3-ylene group (—CH$_2$CH$_2$CH(CH$_3$)—), or a 3-methylbut-1,3-ylene group (—CH$_2$CH$_2$C(CH$_3$)$_2$—); alternatively, an eth-1,2-ylene group (—CH$_2$CH$_2$—), an ethen-1,2-ylene group (—CH=CH—), a prop-1,3-ylene group (—CH$_2$CH$_2$CH$_2$—), or a phen-1,2-ylene group; alternatively, an eth-1,2-ylene group (—CH$_2$CH$_2$—) or a prop-1,3-ylene group (—CH$_2$CH$_2$CH$_2$—); alternatively, an ethen-1,2-ylene group (—CH=CH—) or a phen-1,2-ylene group. In other embodiments, L$^{12}$ and/or L$^{23}$ can be an eth-1,2-ylene group (—CH$_2$CH$_2$—); alternatively, an ethen-1,2-ylene group (—CH=CH—); alternatively, a prop-1,3-ylene group (—CH$_2$CH$_2$CH$_2$—); alternatively, a 1-methylethen-1,2-ylene group (—C(CH$_3$)=CH—); alternatively, a but-,3-lene group (—CH$_2$CH$_2$CH(CH$_3$)—); alternatively, a 3-methylbut-1,3-ylene group (—CH$_2$CH$_2$C(CH$_3$)$_2$—); or alternatively, a phen-1,2-ylene group. In some embodiments, L$^{12}$ and/or L$^{23}$ can be a —CH=CH—CH= group. In an embodiment, L$^{12}$ can have a structure that can comprise at least one substituent located on the carbon atom attached to the N$^1$ nitrogen atom of the N$^2$-phosphinyl guanidine compound, N$^2$-phosphinyl guanidine transition metal complex, or N$^2$-phosphinyl guanidine chromium complex; alternatively, can comprise only one substituent located on the carbon atom attached to the N$^1$ nitrogen atom of the N$^2$-phosphinyl guanidine compound, N$^2$-phosphinyl guanidine transition metal complex, or N$^2$-phosphinyl guanidine chromium complex; or alternatively, can comprise two substituents located on the carbon atom attached to the N$^1$ nitrogen atom of the N$^2$-phosphinyl guanidine compound, N$^2$-phosphinyl guanidine transition metal complex, or N$^2$-phosphinyl guanidine chromium complex. In another embodiment, L$^{12}$ can have a structure that can consist of one substituent located on the carbon atom attached to N$^1$ nitrogen atom of the N$^2$-phosphinyl guanidine compound, N$^2$-phosphinyl guanidine transition metal complex, or N$^2$-phosphinyl guanidine chromium complex; or alternatively, can consist of two substituents located on the carbon atom attached to N$^1$ nitrogen atom of the N$^2$-phosphinyl guanidine compound, N$^2$-phosphinyl guanidine transition metal complex, or N$^2$-phosphinyl guanidine chromium complex.

In an embodiment, R$^{2a}$ and R$^{2b}$ of the N$^2$-phosphinyl guanidine compounds, the N$^2$-phosphinyl guanidine transition metal complexes, and/or the N$^2$-phosphinyl guanidine chromium complexes can be joined to form a group, L$^{22}$, wherein R$^{2a}$, R$^{2b}$, the N$^3$ nitrogen (or L$^{22}$ and the N$^3$ nitrogen) forms a ring or ring system. In an embodiment, L$^{22}$ of the N$^2$-phosphinyl guanidine compounds, the N$^2$-phosphinyl guanidine transition metal complexes, and/or the N$^2$-phosphinyl guanidine chromium complexes having an L$^{22}$ group can be an organylene group; alternatively, an organylene group consisting of inert functional groups; or alternatively, a hydrocarbylene group. The organylene group which can be utilized as L$^{22}$ of the N$^2$-phosphinyl guanidine compounds, the N$^2$-phosphinyl guanidine transition metal complexes, and/or the N$^2$-phosphinyl guanidine chromium complexes having an L$^{22}$ group can be a C$_3$ to C$_{20}$ organylene group; alternatively, a C$_3$ to C$_{15}$ organylene group; or alternatively, a C$_3$ to C$_{10}$ organylene group. The organylene group consisting of inert functional groups which can be utilized as L$^{22}$ of the N$^2$-phosphinyl guanidine compounds, the N$^2$-phosphinyl guanidine transition metal complexes, and/or the N$^2$-phosphinyl guanidine chromium complexes having an L$^{22}$ group can be a C$_3$ to C$_{20}$ organylene group consisting of inert functional groups; alternatively, a C$_3$ to C$_{15}$ organylene group consisting of inert functional groups; or alternatively, a C$_3$ to C$_{10}$ organylene group consisting of inert functional groups. The hydrocarbylene group which can be utilized as L$^{22}$ of the N$^2$-phosphinyl guanidine compounds, the N$^2$-phosphinyl guanidine transition metal complexes, and/or the N$^2$-phosphinyl guanidine chromium complexes having an L$^{22}$ group can be a C$_4$ to C$_{20}$ hydrocarbylene group; alternatively, a C$_4$ to C$_{15}$ hydrocarbylene group; or alternatively, a C$_4$ to C$_{10}$ hydrocarbylene group.

In an embodiment, L$^{22}$ can have any structure provided in Table 2. In some embodiments, L$^{22}$ can have Structure 11L, Structure 12L, Structure 13L, Structure 14L, Structure 15L; or Structure 16L. In other embodiments, L$^{22}$ can have Structure 11L; alternatively, Structure 12L; alternatively, Structure 13L; alternatively, Structure 14L; or alternatively, Structure 15L.

TABLE 2

Structures for Linking Groups L$^{22}$.

| —(CR$^{L31}$R$^{L32}$)$_n$— | —CR$^{L41}$R$^{L42}$—CR$^{L45}$R$^{L46}$CR$^{L47}$CR$^{L48}$CR$^{L43}$R$^{L44}$— |
|---|---|
| Structure 11L | Structure 12L |
| —CR$^{L41}$R$^{L42}$—CR$^{L45}$R$^{L46}$—CR$^{L49}$R$^{L50}$—CR$^{L47}$R$^{L48}$—CR$^{L43}$R$^{L44}$— | |
| Structure 13L | |
| —CR$^{L41}$R$^{L42}$—CR$^{L45}$R$^{L46}$—O—CR$^{L47}$R$^{L48}$—CR$^{L43}$R$^{L44}$— | —CR$^{L51}$=CR$^{L53}$—CR$^{L54}$=CR$^{L52}$— |
| Structure 14L | Structure 15L |

Within the structures of Table 2, the undesignated valencies represent the points at which L$^{22}$ of the N$^2$-phosphinyl guanidine compound, N$^2$-phosphinyl guanidine transition metal complexes, or N$^2$-phosphinyl chromium complex, when present, attaches to the N$^3$ nitrogen atom of the N$^2$-phosphinyl guanidine transition metal complex, or N$^2$-phosphinyl chromium complex. Generally, n can be an integer ranging from 4 to 7. In further embodiments, n can be 4 or 5; alternatively, n can be 4; or alternatively, n can be 5. R$^{L31}$ and R$^{L32}$ of the linking group having Structure 11L, R$^{L41}$, R$^{L42}$, R$^{L43}$, R$^{L44}$, R$^{L45}$, R$^{L46}$, R$^{L47}$, and R$^{L48}$ of the linking group having Structure 12L, R$^{L41}$, R$^{L42}$, R$^{L43}$, R$^{L44}$, R$^{L45}$, R$^{L46}$, R$^{L47}$, R$^{L48}$, R$^{L49}$, and R$^{L50}$ of the linking group having Structure 13L, R$^{L41}$, R$^{L42}$, R$^{L43}$, R$^{L44}$, R$^{L45}$, R$^{L46}$, R$^{L47}$, and R$^{L48}$ of the linking group having Structure 14L, R$^{L41}$, R$^{L42}$, R$^{L43}$, R$^{L44}$, R$^{L45}$, R$^{L46}$, R$^{L47}$, and R$^{L48}$ of the linking group having Structure 15L, and R$^{L51}$, R$^{L52}$, R$^{L53}$, and R$^{L54}$ of the linking group having Structure 16L independently can be a hydrogen or a non-hydrogen substituent group; alternatively, hydrogen. Non-hydrogen substituent groups are independently disclosed herein and can be utilized without limitation to further describe the linking group having Structure 11L, Structure 12L, Structure 13L, Structure 14L, and/or Structure 15L. In an embodiment, $L^{22}$ can be a but-1,4-ylene group, a pent-1,4-ylene group, a pent-1,5-ylene group, a hex-2,5-ylene group, a hex-1,5-ylene group, a hept-2,5-ylene group, a buta-1,3-dien-1,4-ylene group, or a bis(eth-2-yl)ether group; alternatively, a but-1,4-ylene group, a pent-1,5-ylene group, or a bis(eth-2-yl) ether group; alternatively, a but-1,4-ylene group; alternatively, a pent-1,5-ylene group; alternatively, a buta-1,3-dien-1,4-ylene group; or alternatively, a bis(eth-2-yl)ether group.

Generally, $R^3$ of the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes which have an $R^3$ group can be hydrogen or an organyl group; hydrogen or an organyl group consisting essentially of inert functional group; alternatively, hydrogen or a hydrocarbyl group; alternatively, hydrogen; alternatively, an organyl group; alternatively, an organyl group consisting essentially of inert functional group; or alternatively, a hydrocarbyl group. In some embodiments, the organyl group which can utilized as $R^3$ of the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes which have an $R^3$ group can be a $C_1$ to $C_{30}$ organyl group; alternatively, a $C_1$ to $C_{20}$ organyl group; alternatively, a $C_1$ to $C_{15}$ organyl group; alternatively, a $C_1$ to $C_{10}$ organyl group; or alternatively, a $C_1$ to $C_5$ organyl group. In some embodiments, the organyl group consisting of inert function groups which can utilized as $R^3$ of the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes which have an $R^3$ group can be a $C_1$ to $C_{30}$ organyl group consisting essentially of inert functional groups; alternatively, a $C_1$ to $C_{20}$ organyl group consisting essentially of inert functional groups; alternatively, a $C_1$ to $C_{15}$ organyl group consisting essentially of inert functional groups; alternatively, a $C_1$ to $C_{10}$ organyl group consisting essentially of inert functional groups; or alternatively, a $C_1$ to $C_5$ organyl group consisting essentially of inert functional groups. In some embodiments, the hydrocarbyl group which can utilized as $R^3$ of the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes which have an $R^3$ group can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_5$ hydrocarbyl group. In other embodiments, $R^3$ of the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes which have an $R^3$ group can be a $C_1$ to $C_{30}$ alkyl group; alternatively, a $C_1$ to $C_{20}$ alkyl group; alternatively, a $C_1$ to $C_{15}$ alkyl group; or alternatively, a $C_1$ to $C_{10}$ alkyl group; or alternatively, a $C_1$ to $C_5$ alkyl group. In yet other embodiments, $R^3$ of the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes which have an $R^3$ group can be a $C_3$ to $C_{30}$ aromatic group; alternatively, a $C_3$ to $C_{20}$ aromatic group; alternatively, a $C_3$ to $C_{15}$ aromatic group; or alternatively, a $C_3$ to $C_{10}$ aromatic group. In further embodiments, $R^3$ of the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes which have an $R^3$ group can be a phenyl group or a $C_6$ to $C_{30}$ substituted phenyl group; alternatively, a phenyl group or a $C_6$ to $C_{20}$ substituted phenyl group; alternatively, a phenyl group or a $C_6$ to $C_{15}$ substituted phenyl group; or alternatively, a phenyl group or a $C_6$ to $C_{10}$ substituted phenyl group. General substituent groups are provided herein and these general substituent groups can be utilized to further describe the substituted phenyl groups which can be utilized as $R^3$ for the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes.

Generally, $R^4$ and/or $R^5$ of the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes independently can be an organyl group; alternatively, an organyl group consisting essentially of inert functional groups; or alternatively, a hydrocarbyl group. In an embodiment, $R^4$ and/or $R^5$ of the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes independently can be a $C_1$ to $C_{30}$ organyl group; alternatively, a $C_1$ to $C_{20}$ organyl group; alternatively, a $C_1$ to $C_{15}$ organyl group; alternatively, a $C_1$ to $C_{10}$ organyl group; or alternatively, a $C_1$ to $C_5$ organyl group. In an embodiment, $R^4$ and/or $R^5$ of the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes independently can be a $C_1$ to $C_{30}$ organyl group consisting essentially of inert functional groups; alternatively, a $C_1$ to $C_{20}$ organyl group consisting essentially of inert functional groups; alternatively, a $C_1$ to $C_{15}$ organyl group consisting essentially of inert functional groups; alternatively, a $C_1$ to $C_{10}$ organyl group consisting essentially of inert functional groups; or alternatively, a $C_1$ to $C_5$ organyl group consisting essentially of inert functional groups. In an embodiment, $R^4$ and/or $R^5$ of the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes independently can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_5$ hydrocarbyl group.

In other embodiments, $R^4$ and $R^5$ of the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes independently can be a $C_1$ to $C_{30}$ alkyl group; alternatively, a $C_1$ to $C_{20}$ alkyl group; alternatively, a $C_1$ to $C_{15}$ alkyl group; or alternatively, a $C_1$ to $C_{10}$ alkyl group; or alternatively, a $C_1$ to $C_5$ alkyl group. In yet other embodiments, $R^4$ and $R^5$ of the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes independently can be a $C_6$ to $C_{30}$ aromatic group; alternatively, a $C_6$ to $C_{20}$ aromatic group; alternatively, a $C_6$ to $C_{15}$ aromatic group; or alternatively, a $C_6$ to $C_{10}$ aromatic group. In yet other embodiments, $R^4$ and $R^5$ of the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes independently can be a phenyl group or a $C_6$ to $C_{30}$ substituted phenyl group; alternatively, a phenyl group or a $C_6$ to $C_{20}$ substituted phenyl group; alternatively, a phenyl group or a $C_6$ to $C_{15}$ substituted phenyl group; alternatively, a phenyl group or a $C_6$ to $C_{10}$ substituted phenyl group; or alternatively, a phenyl group. In some embodiments, $R^4$ and $R^5$ of the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes independently can be can be joined to form a ring (regardless of particular type of group—organyl, organyl consisting of inert functional groups, hydrocarbyl, or any species within) containing the phosphorus atom of the $N^2$-phosphinyl formamidine metal complex, the $N^2$-phosphinyl amidine metal complex, and/or the $N^2$-phosphinyl guanidine metal complex. General substituent groups are provided herein and these general substituent groups can be utilized to further describe the substituted phenyl groups which can be utilized as $R^4$ and/or $R^5$ for the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes.

Various aspects and embodiments described herein refer to substituents or non-hydrogen substituents (or alternatively, substituent group). Each substituent or non-hydrogen substituent can be a halide, a hydrocarbyl group, or a hydrocarboxy group; alternatively, a halide or a hydrocarbyl group; alternatively, a halide or a hydrocarboxy group; alternatively, a hydrocarbyl group or a hydrocarboxy group; alternatively, a halide; alternatively, a hydrocarbyl group; or alternatively, a hydrocarboxy group. Each substituent or non-hydrogen substituent of any aspect or embodiment calling for a substituent independently can be a halide, a $C_1$ to $C_{10}$ hydrocarbyl group, or a $C_1$ to $C_{10}$ hydrocarboxy group; alternatively, a halide or a $C_1$ to $C_{10}$ hydrocarbyl group; alternatively, a halide or a $C_1$ to $C_{10}$ hydrocarboxy group; alternatively, a $C_1$ to $C_{10}$ hydrocarbyl group or a $C_1$ to $C_{10}$ hydrocarboxy group; alternatively, a halide; alternatively, a $C_1$ to $C_{10}$ hydrocarbyl group; or alternatively, a $C_1$ to $C_{10}$ hydrocarboxy group. In other embodiments, each substituent or non-hydrogen substituent of any aspect or embodiment calling for a substituent independently can be a halide, a $C_1$ to $C_5$ hydrocarbyl group, or a $C_1$ to $C_5$ hydrocarboxy group; alternatively, a halide or a $C_1$ to $C_5$ hydrocarbyl group; alternatively, a halide or a $C_1$ to $C_5$ hydrocarboxy group; alternatively, a $C_1$ to $C_5$ hydrocarbyl group or a $C_1$ to $C_5$ hydrocarboxy group; alternatively, a halide; alternatively, a $C_1$ to $C_5$ hydrocarbyl group; or alternatively, a $C_1$ to $C_5$ hydrocarboxy group.

In an embodiment, each halide substituent of any aspect or embodiment calling for a substituent or non-hydrogen substituent independently can be a fluoride, chloride, bromide, or iodide; alternatively, a fluoride or chloride. In some embodiments, each halide substituent of any aspect or embodiment calling for a substituent of non-hydrogen substituent independently can be a fluoride; alternatively, a chloride; alternatively, a bromide; or alternatively, an iodide.

In an embodiment, each hydrocarbyl substituent of any aspect or embodiment calling for a substituent or non-hydrogen substituent independently can be an alkyl group, an aryl group, or an aralkyl group; alternatively, an alkyl group; alternatively, an aryl group; or alternatively, an aralkyl group. In an embodiment, each alkyl substituent of any aspect or embodiment calling for a substituent or non-hydrogen substituent independently can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an embodiment, each aryl substituent of any aspect or embodiment calling for a substituent or non-hydrogen substituent independently can be phenyl group, a tolyl group, a xylyl group, or a 2,4,6-trimethylphenyl group; alternatively, a phenyl group; alternatively, a tolyl group; alternatively, a xylyl group; or alternatively, a 2,4,6-trimethylphenyl group. In an embodiment, each aralkyl substituent of any aspect or embodiment calling for a substituent or non-hydrogen substituent independently can be benzyl group or an ethylphenyl group (2-phenyleth-1-yl or 1-phenyleth-1-yl); alternatively, a benzyl group; alternatively, an ethylphenyl group; alternatively a 2-phenyleth-1-yl group; or alternatively, a 1-phenyleth-1-yl group.

In an embodiment, each hydrocarboxy substituent of any aspect or embodiment calling for a substituent or non-hydrogen substituent independently can be an alkoxy group, an aryloxy group, or an aralkoxy group; alternatively, an alkoxy group; alternatively, an aryloxy group, or an aralkoxy group. In an embodiment, each alkoxy substituent of any aspect or embodiment calling for a substituent or non-hydrogen substituent can be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an embodiment, each aryloxy substituent of any aspect or embodiment calling for a substituent or non-hydrogen substituent independently can be phenoxy group, a toloxy group, a xyloxy group, or a 2,4,6-trimethylphenoxy group; alternatively, a phenoxy group; alternatively, a toloxy group; alternatively, a xyloxy group; or alternatively, a 2,4,6-trimethylphenoxy group. In an embodiment, each aralkoxy substituent of any aspect or embodiment calling for a substituent or non-hydrogen substituent independently can be benzoxy group.

Generally, the neutral ligand, Q, of the $N^2$-phosphinyl formamidine transition metal complexes, the $N^2$-phosphinyl formamidine chromium complexes, the $N^2$-phosphinyl amidine transition metal complexes, the $N^2$-phosphinyl amidine chromium complexes, the $N^2$-phosphinyl guanidine transition metal complexes, and/or the $N^2$-phosphinyl guanidine chromium complexes, if present, independently can be any neutral ligand that forms an isolatable compound with the $N^2$-phosphinyl formamidine transition metal complex, the $N^2$-phosphinyl formamidine chromium complex, the $N^2$-phosphinyl amidine transition metal complex, the $N^2$-phosphinyl amidine chromium complex, the $N^2$-phosphinyl guanidine transition metal complex, and/or the $N^2$-phosphinyl guanidine chromium complex. In an aspect, each neutral ligand independently can be a nitrile or an ether. In an embodiment, the neutral ligand can be a nitrile; or alternatively, an ether. The number of neutral ligands, q, of the $N^2$-phosphinyl formamidine transition metal complexes, the $N^2$-phosphinyl formamidine chromium complexes, the $N^2$-phosphinyl amidine transition metal complexes, the $N^2$-phosphinyl amidine chromium complexes, the $N^2$-phosphinyl guanidine transition metal complexes, and/or the $N^2$-phosphinyl guanidine chromium complexes can be any number that forms an isolatable compound with the $N^2$-phosphinyl formamidine transition metal complex, the $N^2$-phosphinyl formamidine chromium complex, the $N^2$-phosphinyl amidine transition metal complex, the $N^2$-phosphinyl amidine chromium complex, the $N^2$-phosphinyl guanidine transition metal complex, and/or the $N^2$-phosphinyl guanidine chromium complex. In an aspect, the number of neutral ligands can be from 0 to 6; alternatively, 0 to 3; alternatively, 0; alternatively, 1; alternatively, 2; alternatively, 3; or alternatively, 4.

Generally, each neutral nitrile ligand independently can be a $C_2$ to $C_{20}$ nitrile; or alternatively, a $C_2$ to $C_{10}$ nitrile. In an embodiment, each neutral nitrile ligand independently can be a $C_2$ to $C_{20}$ aliphatic nitrile, a $C_7$ to $C_{20}$ aromatic nitrile, a $C_8$ to $C_{20}$ aralkane nitrile, or any combination thereof; alternatively, a $C_2$ to $C_{20}$ aliphatic nitrile; alternatively, a $C_7$ to $C_{20}$ aromatic nitrile; or alternatively, a $C_8$ to $C_{20}$ aralkane nitrile. In some embodiments, each neutral nitrile ligand independently can be a $C_2$ to $C_{10}$ aliphatic nitrile, a $C_7$ to $C_{10}$ aromatic nitrile, a $C_8$ to $C_{10}$ aralkane nitrile, or any combination thereof; alternatively, a $C_1$ to $C_{10}$ aliphatic nitrile; alternatively, a $C_7$ to $C_{10}$ aromatic nitrile; or alternatively, a $C_8$ to $C_{10}$ aralkane nitrile. In an embodiment, each aliphatic nitrile independently can be acetonitrile, propionitrile, a butyronitrile, benzonitrile, or any combination thereof; alternatively, acetonitrile; alternatively, propionitrile; alternatively, a butyronitrile; or alternatively, benzonitrile.

Generally, each neutral ether ligand independently can be a $C_2$ to $C_{40}$ ether; alternatively, a $C_2$ to $C_{30}$ ether; or alternatively, a $C_2$ to $C_{20}$ ether. In an embodiment, each neutral ligand independently can be a $C_2$ to $C_{40}$ aliphatic ether, a $C_3$ to $C_{40}$ aliphatic cyclic ether, a $C_4$ to $C_{40}$ aromatic cyclic ether; alternatively, a $C_2$ to $C_{40}$ aliphatic acyclic ether or a $C_3$ to $C_{40}$ aliphatic cyclic ether; alternatively, a $C_2$ to $C_{40}$ aliphatic acyclic ether; alternatively, a $C_3$ to $C_{40}$ aliphatic cyclic ether; or alternatively, a $C_4$ to $C_{40}$ aromatic cyclic ether. In some embodiments, each neutral ether ligand independently can be a $C_2$ to $C_{30}$ aliphatic ether, a $C_3$ to $C_{30}$ aliphatic cyclic ether, a $C_4$ to $C_{30}$ aromatic cyclic ether; alternatively, a $C_2$ to $C_{30}$ aliphatic acyclic ether or a $C_3$ to $C_{30}$ aliphatic cyclic ether; alternatively, a $C_2$ to $C_{30}$ aliphatic acyclic ether; alternatively, a $C_3$ to $C_{30}$ aliphatic cyclic ether; or alternatively, a $C_4$ to $C_{30}$ aromatic cyclic ether. In other embodiments, each neutral ether ligand independently can be a $C_2$ to $C_{20}$ aliphatic ether, a $C_3$ to $C_{20}$ aliphatic cyclic ether, a $C_4$ to $C_{20}$ aromatic cyclic ether; alternatively, a $C_2$ to $C_{20}$ aliphatic acyclic ether or a $C_3$ to $C_{20}$ aliphatic cyclic ether; alternatively, a $C_2$ to $C_{20}$ aliphatic acyclic ether; alternatively, a $C_3$ to $C_{20}$ aliphatic cyclic ether; or alternatively, a $C_4$ to $C_{20}$ aromatic cyclic ether. In some embodiments, each neutral ether ligand independently can be dimethyl ether, diethyl ether, a dipropyl ether, a dibutyl ether, methyl ethyl ether, a methyl propyl ether, a methyl butyl ether, tetrahydrofuran, a dihydrofuran, 1,3-dioxolane, tetrahydropyran, a dihydropyran, a pyran, a dioxane, furan, benzofuran, isobenzofuran, isobenzofuran, dibenzofuran, diphenyl ether, a ditolyl ether, or any combination thereof; alternatively, dimethyl ether, diethyl ether, a dipropyl ether, a dibutyl ether, methyl ethyl ether, a methyl propyl ether, a methyl butyl ether, or any combination thereof; tetrahydrofuran, a dihydrofuran, 1,3-dioxolane, tetrahydropyran, a dihydropyran, a pyran, a dioxane, or any combination thereof; furan, benzofuran, isobenzofuran, isobenzofuran, dibenzofuran, or any combination thereof; diphenyl ether, a ditolyl ether, or any combination thereof; alternatively, dimethyl ether; alternatively, diethyl ether; alternatively, a dipropyl ether; alternatively, a dibutyl ether; alternatively, methyl ethyl ether; alternatively, a methyl propyl ether; alternatively, a methyl butyl ether; alternatively, tetrahydrofuran; alternatively, a dihydrofuran; alternatively, 1,3-dioxolane; alternatively, tetrahydropyran; alternatively, a dihydropyran; alternatively, a pyran; alternatively, a dioxane; alternatively, furan; alternatively, benzofuran; alternatively, isobenzofuran; alternatively, isobenzofuran; alternatively, dibenzofuran; alternatively, diphenyl ether; or alternatively, a ditolyl ether.

The metal alkyl compound which can be utilized in any catalyst system described herein can be any heteroleptic or homoleptic metal alkyl compound. In an embodiment, the metal alkyl can comprise, consist essentially of, or consist of, a non-halide metal alkyl, a metal alkyl halide, or any combination thereof; alternatively, a non-halide metal alkyl; or alternatively, a metal alkyl halide.

In an embodiment, the metal of the metal alkyl compound can comprise, consist essentially of, or consist of, a group 1, 2, 11, 12, 13, or 14 metal; or alternatively, a group 13 or 14 metal; or alternatively, a group 13 metal. In some embodiments, the metal of the metal alkyl compound (non-halide metal alkyl or metal alkyl halide) can be lithium, sodium, potassium, rubidium, cesium, beryllium, magnesium, calcium, strontium, barium, zinc, cadmium, boron, aluminum, or tin; alternatively, lithium, sodium, potassium, magnesium, calcium, zinc, boron, aluminum, or tin; alternatively, lithium, sodium, or potassium; alternatively, magnesium or calcium; alternatively, lithium; alternatively, sodium; alternatively, potassium; alternatively, magnesium; alternatively, calcium; alternatively, zinc; alternatively, boron; alternatively, aluminum; or alternatively, tin. In some embodiments, the metal alkyl compound (non-halide metal alkyl or metal alkyl halide) can comprise, consist essentially of, or consist of, a lithium alkyl compound, a sodium alkyl compound, a magnesium alkyl compound, a boron alkyl compound, a zinc alkyl compound, or an alkylaluminum compound. In some embodiments, the metal alkyl (non-halide metal alkyl or metal alkyl halide) can comprise, consist essentially of, or consist of, an alkylaluminum compound.

In an embodiment, the alkylaluminum compound can be a trialkylaluminum, an alkylaluminum halide, an alkylaluminum alkoxide, an aluminoxane, or any combination thereof. In some embodiments, the alkylaluminum compound can be a trialkylaluminum, an alkylaluminum halide, an aluminoxane, or any combination thereof; a trialkylaluminum, an alkylaluminum halide, or any combination thereof; or alternatively, a trialkylaluminum, an aluminoxane, or any combination thereof. In other embodiments, the alkylaluminum compound can be a trialkylaluminum; alternatively, an alkylaluminum halide; alternatively, an alkylaluminum alkoxide; or alternatively, an aluminoxane.

In a non-limiting embodiment, the aluminoxane can have a repeating unit characterized by the Formula I:

Formula I wherein R' is a linear or branched alkyl group. Alkyl groups for metal alkyl compounds are independently described herein and can be utilized without limitation to further describe the aluminoxanes having Formula I. Generally, n of Formula I can be greater than 1; or alternatively, greater than 2. In an embodiment, n can range from 2 to 15; or alternatively, range from 3 to 10.

In an aspect, each halide of any metal alkyl halide disclosed herein independently can be, comprise, or consist essentially of, fluoride, chloride, bromide, or iodide; alternatively, chloride, bromide, or iodide. In an embodiment, each halide of any metal alkyl halide disclosed herein can be fluoride; alternatively, chloride; alternatively, bromide; or alternatively, iodide.

In an aspect, each alkyl group of any metal alkyl compound disclosed herein (non-halide metal alkyl or metal alkyl halide) independently can be, comprise, or consist essentially of, a $C_1$ to $C_{20}$ alkyl group; alternatively, a $C_1$ to $C_{10}$ alkyl group; or alternatively, a $C_1$ to $C_6$ alkyl group. In an embodiment, each alkyl group(s) of any metal alkyl compound disclosed herein (non-halide metal alkyl or metal alkyl halide) independently can be, comprise, or consist essentially of, a methyl group, an ethyl group, a propyl group, a butyl group, a pentyl group, a hexyl group, a heptyl group, or an octyl group; alternatively, a methyl group, a ethyl group, a butyl group, a hexyl group, or an octyl group. In some embodiments, alkyl group independently can be, comprise, or consist essentially of, a methyl group, an ethyl group, an n-propyl group, an n-butyl group, an iso-butyl group, an n-hexyl group, or an n-octyl group; alternatively, a methyl group, an ethyl group, an n-butyl group, or an iso-butyl group; alternatively, a methyl group; alternatively, an ethyl group; alternatively, an n-propyl group; alternatively, an n-butyl group; alternatively, an iso-butyl group; alternatively, an n-hexyl group; or alternatively, an n-octyl group.

In an aspect, each alkoxide group of any metal alkyl alkoxide disclosed herein independently can be, comprise, or consist essentially of, a $C_1$ to $C_{20}$ alkoxy group; alternatively, a $C_1$ to $C_{10}$ alkoxy group; or alternatively, a $C_1$ to $C_6$ alkoxy group. In an embodiment, each alkoxide group of any metal alkyl alkoxide disclosed herein independently can be, comprise, or consist essentially of, a methoxy group, an ethoxy group, a propoxy group, a butoxy group, a pentoxy group, a hexoxy group, a heptoxy group, or an octoxy group; alternatively, a methoxy group, a ethoxy group, a butoxy group, a hexoxy group, or an octoxy group. In some embodiments, each alkoxide group of any metal alkyl alkoxide disclosed herein independently can be, comprise, or consist essentially of, a methoxy group, an ethoxy group, an n-propoxy group, an n-butoxy group, an iso-butoxy group, an n-hexoxy group, or an n-octoxy group; alternatively, a methoxy group, an ethoxy group, an n-butoxy group, or an iso-butoxy group; alternatively, a methoxy group; alternatively, an ethoxy group; alternatively, an n-propoxy group;

alternatively, an n-butoxy group; alternatively, an iso-butoxy group; alternatively, an n-hexoxy group; or alternatively, an n-octoxy group.

In a non-limiting embodiment, the metal alkyl compound can be, comprise, or consist essentially of, methyl lithium, n-butyl lithium, sec-butyl lithium, tert-butyl lithium, diethyl magnesium, di-n-butylmagnesium, ethylmagnesium chloride, n-butylmagnesium chloride, or diethyl zinc.

In a non-limiting embodiment, the trialkylaluminum compound can be, comprise, or consist essentially of, trimethylaluminum, triethylaluminum, tripropylaluminum, tributylaluminum, trihexylaluminum, trioctylaluminum, or mixtures thereof. In some non-limiting embodiments, the trialkylaluminum compound can be, comprise, or consist essentially of, trimethylaluminum, triethylaluminum, tripropylaluminum, tri-n-butylaluminum, tri-isobutylaluminum, trihexylaluminum, tri-n-octylaluminum, or mixtures thereof; alternatively, triethylaluminum, tri-n-butylaluminum, tri-isobutylaluminum, trihexylaluminum, tri-n-octylaluminum, or mixtures thereof; alternatively, triethylaluminum, tri-n-butylaluminum, trihexylaluminum, tri-n-octylaluminum, or mixtures thereof. In other non-limiting embodiments, the trialkylaluminum compound can be, comprise, or consist essentially of, trimethylaluminum; alternatively, triethylaluminum; alternatively, tripropylaluminum; alternatively, tri-n-butylaluminum; alternatively, tri-isobutylaluminum; alternatively, trihexylaluminum; or alternatively, tri-n-octylaluminum.

In a non-limiting embodiment, the alkylaluminum halide can be, comprise, or consist essentially of, diethylaluminum chloride, diethylaluminum bromide, ethylaluminum dichloride, ethylaluminum sesquichloride, and mixtures thereof. In some non-limiting embodiments, the alkylaluminum halide can be, comprise, or consist essentially of, diethylaluminum chloride, ethylaluminum dichloride, ethylaluminum sesquichloride, and mixtures thereof. In other non-limiting embodiments, the alkylaluminum halide can be, comprise, or consist essentially of, diethylaluminum chloride; alternatively, diethylaluminum bromide; alternatively, ethylaluminum dichloride; or alternatively, ethylaluminum sesquichloride.

In a non-limiting embodiment, the aluminoxane can be, comprise, or consist essentially of, methylaluminoxane (MAO), ethylaluminoxane, modified methylaluminoxane (MMAO), n-propylaluminoxane, iso-propyl-aluminoxane, n-butylaluminoxane, sec-butylaluminoxane, iso-butylaluminoxane, t-butylaluminoxane, 1-pentyl-aluminoxane, 2-entylaluminoxane, 3-pentyl-aluminoxane, iso-pentyl-aluminoxane, neopentylaluminoxane, or mixtures thereof. In some non-limiting embodiments, the aluminoxane can be, comprise, or consist essentially of, methylaluminoxane (MAO), modified methylaluminoxane (MMAO), isobutyl aluminoxane, t-butyl aluminoxane, or mixtures thereof. In other non-limiting embodiments, the aluminoxane can be, comprise, or consist essentially of, methylaluminoxane (MAO); alternatively, ethylaluminoxane; alternatively, modified methylaluminoxane (MMAO); alternatively, n-propylaluminoxane; alternatively, iso-propyl-aluminoxane; alternatively, n-butylaluminoxane; alternatively, sec-butylaluminoxane; alternatively, iso-butylaluminoxane; alternatively, t-butyl aluminoxane; alternatively, 1-pentyl-aluminoxane; alternatively, 2-pentylaluminoxane; alternatively, 3-pentyl-aluminoxane; alternatively, iso-pentyl-aluminoxane; or alternatively, neopentylaluminoxane.

In an embodiment, the halogen containing compound can comprise a chloride containing compound, a bromide containing compound, an iodide containing compound, or any combination thereof. In an embodiment, the halogen containing compound, regardless of whether it is a chloride, bromide, or iodide containing compound, can comprise a metal halide, alkyl metal halide, or an organic halide; alternatively, a metal halide; alternatively, an alkyl metal halide; or alternatively, an organic halide. In additional or alternative embodiments, the halogen containing compound can comprise a group 3 metal halide, a group 4 metal halide, a group 5 metal halide, a group 13 metal halide, a group 14 metal halide, a group 15 metal halide, or any combination thereof. By way of example, the halogen containing compound can comprise scandium chloride, yttrium chloride, lanthanum chloride, titanium tetrachloride, zirconium tetrachloride, hafnium tetrachloride, boron trichloride, aluminum chloride, gallium chloride, silicon tetrachloride, trimethyl chlorosilane, germanium tetrachloride, tin tetrachloride, phosphorus trichloride, antimony trichloride, antimony pentachloride, bismuth trichloride, boron tribromide, aluminum tribromide, silicon tetrachloride, silicon tetrabromide, aluminum fluoride, molybdenum pentachloride, tungsten hexachloride, trityl hexachloroantimonate, or any combination thereof.

In additional or alternative embodiments, the halogen containing compound can comprise a dialkylaluminum halide, an alkylaluminum dihalide, or an alkylaluminum sesquihalide, or any combination thereof. Moreover and in this aspect, the halogen containing compound can comprise diethylaluminum chloride, ethylaluminum sesquichloride, ethylaluminum dichloride, tributyltin chloride, dibutyltin dichloride, or any combination thereof; alternatively, diethylaluminum chloride, ethylaluminum sesquichloride, ethylaluminum dichloride or any combination thereof. In additional or alternative embodiments, the halogen containing compound can comprise a $C_1$ to $C_{15}$ organic halide; alternatively, a $C_1$ to $C_{10}$ organic halide; alternatively, a $C_1$ to $C_8$ organic halide. By way of example, according to this aspect, the halogen containing compound can comprise carbon tetrachloride, carbon tetrabromide, chloroform, bromoform, dichloromethane, dibromoethane, diiodomethane, chloromethane, bromomethane, iodomethane, dichloroethane, tetrachloroethane, trichloroacetone, hexachloroacetone, hexachlorocyclohexane, 1,3,5-trichlorobenzene, hexachlorobenzene, trityl chloride, benzyl chloride, benzyl bromide, benzyl iodide, chlorobenzene, bromobenzene, iodobenzene, hexafluorobenzene, or any combination thereof.

In an aspect, the catalyst system to which the present invention can be applied can be selected from a catalyst system comprising a) a transition metal compound, a pyrrole compound, a metal alkyl compound, and optionally, a halide containing compound, b) a transition metal compound, a diphosphinoaminyl compound, and a metal alkyl compound, c) a transition metal compound complexed to a diphosphinoaminyl compound, and a metal alkyl compound, d) a transition metal compound, an $N^2$-phosphinylamidine compound, and a metal alkyl compound, e) a transition metal compound complexed to an $N^2$-phosphinylamidine compound, and a metal alkyl compound, f) a transition metal compound, an $N^2$-phosphinylformamidine compound, and a metal alkyl compound, g) a transition metal compound complexed to an $N^2$-phosphinylformamidine compound, and a metal alkyl compound, h) a transition metal compound, an $N^2$-phosphinyl guanidine compound, and a metal alkyl compound, i) a transition metal compound complexed to an $N^2$-phosphinyl guanidine compound, and a metal alkyl compound, and j) combinations thereof. In another aspect, the catalyst system to which the present invention can be applied can be selected from a catalyst system comprising a)

a chromium compound, a pyrrole compound, a metal alkyl compound, and optionally, a halide containing compound, b) a chromium compound, a diphosphinoaminyl compound, and a metal alkyl compound, c) a chromium compound complexed to a diphosphinoaminyl compound, and a metal alkyl compound, d) a chromium compound, an $N^2$-phosphinylamidine compound, and a metal alkyl compound, e) a chromium compound complexed to an $N^2$-phosphinylamidine compound, and a metal alkyl compound, f) a chromium compound, an $N^2$-phosphinylformamidine compound, and a metal alkyl compound, g) a chromium compound complexed to an $N^2$-phosphinylformamidine compound, and a metal alkyl compound, h) a chromium compound, an $N^2$-phosphinyl guanidine compound, and a metal alkyl compound, i) a chromium compound complexed to an $N^2$-phosphinyl guanidine compound, and a metal alkyl compound, and j) combinations thereof.

In an embodiment, the catalyst system can comprise a transition metal compound, an amine, amide, or imide compound, a metal alkyl compound, and optionally, a halide containing compound. In an embodiment, the catalyst system can comprise a chromium compound, an amine, amide, or imide compound, a metal alkyl compound, and optionally, a halide containing compound. In some embodiments, the catalyst system can comprise a chromium compound, a pyrrole compound, a metal alkyl compound, and optionally, a halide containing compound. The catalyst system using a pyrrole compound can be referred to as a chromium-pyrrole catalyst system. The chromium-pyrrole catalyst system can be an ethylene trimerization catalyst system where the specified oligomerization product (or trimerization product) typically comprises at least 70 wt. % hexenes. In some chromium-pyrrole catalyst system embodiments, the chromium compound can comprise, or consist essentially of, a chromium carboxylate and the alkylaluminum compound can comprise, or consist essentially of, a trialkylaluminum compound, a dialkylaluminum halide, an alkylaluminum dihalide, an alkylaluminum sesquihalide, or any combination thereof. In some chromium-pyrrole catalyst system embodiments, the optional halide containing compound can be an organo halide compound, a metal halide compound (e.g., an inorganic metal halide compound or an alkyl metal halide compound), or a combination thereof. In a chromium-pyrrole catalyst system embodiment, the catalyst system can comprise chromium(III) 2-ethylhexanoate, 2,5-dimethyl pyrrole, triethylaluminum, and diethylaluminum chloride. Additional information regarding the use of chromium-pyrrole catalyst systems for oligomerizing (or trimerizing) ethylene (including specific examples) can be found in, but not limited to, U.S. Pat. No. 5,198,563, U.S. Pat. No. 5,288,823, EP 608447A1, U.S. Pat. No. 5,331,104, U.S. Pat. No. 5,340,785, U.S. Pat. No. 5,360,879, U.S. Pat. No. 5,376,612, U.S. Pat. No. 5,382,738, U.S. Pat. No. 5,399,539, U.S. Pat. No. 5,438,027, U.S. Pat. No. 5,470,926, U.S. Pat. No. 5,543,375, U.S. Pat. No. 5,523,507, U.S. Pat. No. 5,563,312, EP 706983A1, U.S. Pat. No. 5,689,028, U.S. Pat. No. 5,750,816, U.S. Pat. No. 5,763,723, U.S. Pat. No. 5,814,575, U.S. Pat. No. 5,856,257, U.S. Pat. No. 5,856,612, U.S. Pat. No. 5,859,303, U.S. Pat. No. 5,910,619, U.S. Pat. No. 6,133,495, U.S. Pat. No. 6,380,451, U.S. Pat. No. 6,455,648, U.S. Pat. No. 7,157,612, U.S. Pat. No. 7,384,886, U.S. Pat. No. 7,476,775, U.S. Pat. No. 7,718,838, U.S. Pat. No. 7,820,581, U.S. Pat. No. 7,910,670, U.S. Pat. No. 8,049,052, U.S. Pat. No. 8,329,608, U.S. Pat. No. 8,344,198, U.S. Pat. No. 8,471,085, US 2010/0036185, US 2010/0113257, US 2010/0113851, US 2010/0113852, US 2013/0150605, US 2010/0331503, or US 2013/0150642.

In an embodiment, the catalyst system can comprise a transition metal compound, a diphosphinoaminyl compound, and a metal alkyl compound; or alternatively, a transition metal compound complexed to a diphosphinoaminyl compound and a metal alkyl compound. In another embodiment, the catalyst system can comprise a chromium compound complexed to a diphosphinoaminyl compound, and a metal alkyl compound; or alternatively, a chromium compound complexed to a diphosphinoaminyl compound and a metal alkyl compound. These catalyst systems can be generically referred to as chromium-PNP catalyst systems. Depending upon the diphosphinoaminyl compound, the chromium-PNP catalyst systems can be an ethylene tetramerization catalyst system where the specified oligomer comprises at least 70 wt. % octenes or a trimerization and tetramerization catalyst system where the specified oligomer comprises at least 70 wt. % hexenes and octenes. In some chromium-PNP catalyst system embodiments, the chromium compound of the catalyst system or the chromium compound of the chromium compound complexed to a diphosphinoaminyl compound, can comprise, or consist essentially of, a chromium halide, carboxylate, β-diketonate, hydrocarboxide, nitrate, sulfate, phosphate, or chlorate; alternatively, a chromium halide, carboxylate, or β-diketonate; alternatively, a chromium halide; alternatively, a chromium carboxylate; or alternatively, chromium β-diketonate. In some chromium-PNP catalyst system embodiments, the alkylaluminum compound can comprise, or consist essentially of, a trialkylaluminum compound, an alkylaluminum halide (e.g., a dialkylaluminum halide, an alkylaluminum dihalide, and/or an alkylaluminum sesquihalide), an aluminoxane, or combinations thereof; or alternatively, comprises an alumoxane. Additional information regarding the use of chromium-PNP catalyst systems for oligomerizing ethylene (including specific examples) can be found in, but not limited to, U.S. Pat. No. 7,285,607, U.S. Pat. No. 7,297,832, U.S. Pat. No. 7,323,524, U.S. Pat. No. 7,323,524, U.S. Pat. No. 7,378,537, U.S. Pat. No. 7,511,183, U.S. Pat. No. 7,525,009, U.S. Pat. No. 7,829,749, U.S. Pat. No. 7,906,681, U.S. Pat. No. 7,964,763, U.S. Pat. No. 7,994,363, U.S. Pat. No. 8,076,523, U.S. Pat. No. 8,134,038, U.S. Pat. No. 8,252,956, U.S. Pat. No. 8,252,955, U.S. Pat. No. 8,268,941, U.S. Pat. No. 8,334,420, U.S. Pat. No. 8,367,786, U.S. Pat. No. 8,461,406, US 2009/0306442, US 2011/0257350, US 2011/0282016, US 2012/0041241, US 2012/0088933, US2012/0101321, US 2012/0142989, US 2012/0199467, US 2012/0271087, US 2012/0316303, and WO 2013013300.

In another embodiment, the catalyst system can comprise a transition metal compound, an $N^2$-phosphinylamidine compound, and a metal alkyl compound; or alternatively, a transition metal compound complexed to an $N^2$-phosphinylamidine compound, and a metal alkyl compound. In another embodiment, the catalyst system can comprise a chromium compound, an $N^2$-phosphinylamidine compound, and a metal alkyl compound. In another embodiment, the catalyst system can comprise a chromium compound complexed to an $N^2$-phosphinylamidine compound and a metal alkyl compound. These catalyst systems can be generically referred to as chromium-$N^2$-phosphinylamidine catalyst systems. Depending upon the $N^2$-phosphinylamidine compound, these catalyst systems can be an ethylene trimerization catalyst system where the specified oligomer comprises at least 70 wt. % hexenes or a trimerization and tetramerization catalyst system where the specified oligomer comprises at least 70 wt. % hexenes and octenes. In some chromium-$N^2$-phosphinylamidine catalyst system embodiments, the chromium compound of the catalyst system or the chromium compound of the chromium compound complexed to a $N^2$-phosphinylamidine compound, can comprise, or consist essentially of, a chromium halide, carboxylate, β-diketonate, hydrocarboxide, nitrate, or chlorate; alternatively, a chromium halide, carboxylate, hydrocarboxide, or β-diketonate; alternatively, a chromium halide; alternatively, a chromium carboxylate; alternatively, a chromium hydrocarboxide; or alternatively, chromium β-diketonate. In some chromium-$N^2$-phosphinylamidine catalyst system embodiments, the alkylaluminum compound can comprise, or consist essentially of, a trialkylaluminum compound, an alkylaluminum halide (e.g., a dialkylaluminum halide, an alkylaluminum dihalide, and/or an alkylaluminum sesquihalide), an alkylaluminum alkoxide, an aluminoxane, or combinations thereof; or alternatively, comprises an alumoxane. Additional information regarding the use of chromium-$N^2$-phosphinylamidine catalyst systems for oligomerizing ethylene (including specific examples) can be found in, but not limited to, U.S. Pat. No. 8,680,003.

In another embodiment, the catalyst system can comprise a transition metal compound, an $N^2$-phosphinylformamidine compound, and a metal alkyl compound; or alternatively, a transition metal compound complexed to an $N^2$-phosphinylformamidine compound and a metal alkyl compound. In another embodiment, the catalyst system can comprise a chromium compound, an $N^2$-phosphinylformamidine compound, and a metal alkyl compound. In another embodiment, the catalyst system can comprise a chromium compound complexed to an $N^2$-phosphinylformamidine compound and a metal alkyl compound. These catalyst systems can be generically referred to as chromium compound-$N^2$-phosphinylformamidine catalyst systems. Depending upon the $N^2$-phosphinylformamidine compound, these catalyst systems can be an ethylene trimerization catalyst system where the specified oligomer comprises at least 70 wt. % hexenes or a trimerization and tetramerization catalyst system where the specified oligomer comprises at least 70 wt. % hexenes and octenes. In some chromium-$N^2$-phosphinylforamidine catalyst system embodiments, the chromium compound of the catalyst system or the chromium compound of the chromium compound complexed to a $N^2$-phosphinylformamidine compound, can comprise, or consist essentially of, a chromium halide, carboxylate, β-diketonate, hydrocarboxide, nitrate, or chlorate; alternatively, a chromium halide, carboxylate, hydrocarboxide, or β-diketonate; alternatively, a chromium halide; alternatively, a chromium carboxylate; alternatively, a chromium hydrocarboxide; or alternatively, chromium β-diketonate. In some chromium-$N^2$-phosphinylforamidine catalyst system embodiments, the alkylaluminum compound can comprise, or consist essentially of, a trialkylaluminum compound, an alkylaluminum halide (e.g., a dialkylaluminum halide, an alkylaluminum dihalide, and/or an alkylaluminum sesquihalide), an alkylaluminum alkoxide, an aluminoxane, or combinations thereof; or alternatively, comprises an alumoxane. Additional information regarding the use of the chromium compound-$N^2$-phosphinylformamidine catalyst systems for oligomerizing ethylene (including specific examples) can be found in, but not necessarily limited to, PCT patent application PCT/US13/75936.

In yet another embodiment, the catalyst system can comprise a transition metal compound, an $N^2$-phosphinylguanidine compound, and a metal alkyl compound; or alternatively, a transition metal compound complexed to an $N^2$-phosphinylguanidine compound and a metal alkyl compound. In yet another embodiment, the catalyst system can comprise a chromium compound, an $N^2$-phosphinylguanidine compound, and a metal alkyl compound. In still another embodiment, the catalyst system can comprise a chromium compound complexed to an $N^2$-phosphinylguanidine compound and a metal alkyl compound. These catalyst systems can be generically referred to as chromium compound-$N^2$-phosphinylguanidine catalyst systems. Depending upon the $N^2$-phosphinyl guanidine compound, these catalyst systems can be an ethylene trimerization catalyst system where the specified oligomer comprises at least 70 wt. % hexenes or a trimerization and tetramerization catalyst system where the specified oligomer comprises at least 70 wt. % hexenes and octenes. In some chromium-$N^2$-phosphinylguanidine catalyst system embodiments, the chromium compound of the catalyst system or the chromium compound of the chromium compound complexed to a $N^2$-phosphinylguanidine compound, can comprise, consist essentially of, a chromium halide, carboxylate, β-diketonate, hydrocarboxide, nitrate, or chlorate; alternatively, a chromium halide, carboxylate, hydrocarboxide, or β-diketonate; alternatively, a chromium halide; alternatively, a chromium carboxylate; alternatively, a chromium hydrocarboxide; or alternatively, chromium β-diketonate. In some chromium-$N^2$-phosphinylguanidine catalyst system embodiments, the alkylaluminum compound can comprise, or consist essentially of, a trialkylaluminum compound, an alkylaluminum halide (e.g., a dialkylaluminum halide, an alkylaluminum dihalide, and/or an alkylaluminum sesquihalide), an alkylaluminum alkoxide, an aluminoxane, or combinations thereof; or alternatively, comprises an alumoxane. Additional information regarding the use of chromium compound-$N^2$-phosphinylguanidine catalyst systems for oligomerizing ethylene (including specific examples) can be found in, but not necessarily limited to, US 2013/0331629.

Combinations of more than one catalyst systems described herein can be employed, if desired. Moreover, the processes disclosed herein are not limited solely to the catalyst systems provided hereinabove.

In embodiments, the catalyst system can be prepared by contacting the catalyst system with hydrogen. Alternatively, in other olefin oligomerization process, an olefin trimerization process, olefin tetramerization process, or olefin trimerization and tetramerization process embodiments, (e.g., ethylene oligomerization process, an ethylene trimerization process, ethylene tetramerization process, or an ethylene trimerization and tetramerization process embodiments), hydrogen can be added to the oligomerization reactor to accelerate the reaction and/or increase catalyst system activity. If desired, hydrogen also can be added to suppress polymer production. When hydrogen is utilized, the hydrogen partial pressure at which the ethylene oligomerization product, ethylene trimerization product, ethylene tetramerization product, or ethylene trimerization and tetramerization product can be formed can range from 2 psi to 100 psi; alternatively, 5 psi to 75 psi; alternatively, 10 psi to 50 psi.

Relating the reaction to oligomerization processes describes herein, the oligomerization reactor can operate at any pressure that can facilitate the oligomerization of an olefin. In an embodiment, the pressure at which the oligomerization reactor can operate can be any pressure that produces the desired oligomerization product(s). In some embodiments, the ethylene oligomerization product, ethylene trimerization product, ethylene tetramerization product, or ethylene trimerization and tetramerization product can be formed at a pressure greater than or equal to 0 psig (0 KPa); alternatively, greater than or equal to 50 psig (344 KPa); alternatively, greater than or equal to 100 psig (689 KPa);

alternatively, greater than or equal to 150 psig (1.0 MPa). In other embodiments, the ethylene oligomerization product, ethylene trimerization product, ethylene tetramerization product, or ethylene trimerization and tetramerization product can be formed at a pressure ranging from 0 psig (0 KPa) to 2,500 psig (17.3 MPa); alternatively, 0 psig (KPa) to 1,600 psig (11.0 MPa); alternatively, 0 psig (KPa) to 1,500 psig (10.4 MPa); alternatively, 50 psig (344 KPa) to 2,500 psig (17.3 MPa); alternatively, 100 psig (689 KPa) to 2,500 psig (17.3 MPa); alternatively, 150 psig (1.0 MPa) to 2,000 psig (13.8 MPa); alternatively, 300 psig (2.0 MPa) to 900 psig (6.2 MPa). In embodiments wherein the monomer reactant is a gas (e.g., ethylene), the oligomerization product can be formed under a monomer gas pressure. When the oligomerization mixture produces an ethylene oligomerization product, ethylene trimerization product, ethylene tetramerization product, or ethylene trimerization and tetramerization product, the pressure can be the ethylene pressure or ethylene partial pressure. In some embodiments, the ethylene pressure (or ethylene partial pressure) at which the ethylene oligomerization product, ethylene trimerization product, ethylene tetramerization product, or ethylene trimerization and tetramerization product can be formed can be greater than or equal to 0 psig (0 KPa); alternatively, greater than or equal to 50 psig (344 KPa); alternatively, greater than or equal to 100 psig (689 KPa); alternatively, greater than or equal to 150 psig (1.0 MPa). In other embodiments, the ethylene pressure at which the ethylene oligomerization product, ethylene trimerization product, ethylene tetramerization product, or ethylene trimerization and tetramerization product can be formed can range from 0 psig (0 KPa) to 2,500 psig (17.3 MPa); alternatively, 50 psig (344 KPa) to 2,500 psig (17.3 MPa); alternatively, 100 psig (689 KPa) to 2,500 psig (17.3 MPa); alternatively, 150 psig (1.0 MPa) to 2,000 psig (13.8).

In an embodiment, the temperature at which the olefin oligomerization product, olefin trimerization product, olefin tetramerization product, or olefin trimerization and tetramerization product (or alternatively, ethylene oligomerization product, ethylene trimerization product, ethylene tetramerization product, or ethylene trimerization and tetramerization product) can be formed can be at least 0° C.; alternatively, at least 10° C.; alternatively, at least 20° C.; alternatively, at least 30° C.; alternatively, at least 40° C.; alternatively, at least 50° C.; alternatively, at least 60° C.; alternatively, at least 70° C.; alternatively, at least 80° C.; alternatively, at least 90° C.; alternatively, at least 100° C.; alternatively, at least 110° C.; alternatively, at least 120° C.; alternatively, at least 130° C.; alternatively, at least 140° C.; alternatively, at least 150° C.; alternatively, at least 160° C.; alternatively, at least 170° C.; alternatively, at least 180° C. In some embodiments, the maximum temperature at which the olefin oligomerization product, olefin trimerization product, olefin tetramerization product, or olefin trimerization and tetramerization product (or alternatively, ethylene oligomerization product, ethylene trimerization product, ethylene tetramerization product, or ethylene trimerization and tetramerization product) can be formed can be 180° C.; alternatively, 160° C.; alternatively, 140° C.; alternatively, 120° C.; alternatively, 100° C.; alternatively, 90° C.; alternatively, 80° C. In some embodiments, the temperature at which the olefin oligomerization product, olefin trimerization product, olefin tetramerization product, or olefin trimerization and tetramerization product (or alternatively, ethylene oligomerization product, ethylene trimerization product, ethylene tetramerization product, or ethylene trimerization and tetramerization product) can be formed can range from any minimum temperature described herein to any maximum reaction temperature described herein as long as the maximum temperature is greater than the minimum temperature. In a non-limiting example, the temperature at which the olefin oligomerization product, olefin trimerization product, olefin tetramerization product, or olefin trimerization and tetramerization product (or alternatively, ethylene oligomerization product, ethylene trimerization product, ethylene tetramerization product, or ethylene trimerization and tetramerization product) can be formed can range from 0° C. to 180° C.; alternatively, range from 10° C. to 160° C.; alternatively, range from 20° C. to 140° C.; alternatively, range from 30° C. to 120° C.; alternatively, range from 40° C. to 100° C.; alternatively, range from 50° C. to 100° C.; alternatively, range from 60° C. to 140° C. Other temperature ranges at which the olefin oligomerization product, olefin trimerization product, olefin tetramerization product, or olefin trimerization and tetramerization product (or alternatively, ethylene oligomerization product, ethylene trimerization product, ethylene tetramerization product, or ethylene trimerization and tetramerization product) can be formed can be understood by those skilled in the art with the aid of this disclosure.

The reaction time can comprise any time that can produce the desired quantity of olefin oligomerization product, olefin trimerization product, olefin tetramerization product, or olefin trimerization and tetramerization product (or alternatively, ethylene oligomerization product, ethylene oligomerization product, ethylene trimerization product, ethylene tetramerization product, or ethylene trimerization and tetramerization product) can be formed; alternatively, any time that can provide a desired catalyst system productivity; alternatively, any time that can provide a desired conversion of olefin (or alternatively, ethylene). For example, the olefin monomer (or alternatively, ethylene monomer) can be at least 30 wt. % percent; alternatively, at least 35 wt. % percent; alternatively, at least 40 wt. % percent; alternatively, at least 45 wt. % percent.

In an embodiment, the ethylene trimerization product can comprise at least 70 wt. % hexene; alternatively, at least 75 wt. % hexene; alternatively, at least 80 wt. % hexene; alternatively, at least 85 wt. % hexene; or alternatively, at least 90 wt. % hexene based upon the weight of the oligomerization product. In some embodiments, the ethylene trimerization product can comprise from 70 wt. % to 99.8 wt. % hexene; alternatively, from 75 wt. % to 99.7 wt. % hexene; or alternatively, from 80 wt. % to 99.6 wt. % hexene based upon the weight of the ethylene trimerization product. In an embodiment, the ethylene tetramerization product can comprise at least 70 wt. % octene; alternatively, at least 75 wt. % octene; alternatively, at least 80 wt. % octene; alternatively, at least 85 wt. % octene; or alternatively, at least 90 wt. % octene based upon the weight of the ethylene tetramerization product. In some embodiments, the ethylene tetramerization product can comprise from 70 wt. % to 99.8 wt. % octene; alternatively, from 75 wt. % to 99.7 wt. % octene; or alternatively, from 80 wt. % to 99.6 wt. % octene based upon the weight of the ethylene tetramerization product. In other embodiments, the ethylene trimerization and tetramerization product can comprise at least 70 wt. % hexene and octene; alternatively, at least 75 wt. % hexene and octene; alternatively, at least 80 wt. % hexene and octene; alternatively, at least 85 wt. % hexene and octene; or alternatively, at least 90 wt. % hexene and octene based upon the weight of the ethylene trimerization and tetramerization product. In other embodiments, the ethylene trimerization and tetramerization product can comprise from 70 wt. % to 99.8 wt. % hexene and octene; alternatively, from 75 wt. % to 99.7 wt. % hexene and octene; or alternatively, from 80 wt. % to 99.6 wt. % hexene and octene based upon the weight of the ethylene trimerization and tetramerization product.

In ethylene oligomerization, ethylene trimerization, or ethylene trimerization and tetramerization embodiments, the ethylene trimer can comprise at least 85 wt. % 1-hexene; alternatively, at least 87.5 wt. % 1-hexene; alternatively, at least 90 wt. % 1-hexene; alternatively, at least 92.5 wt. % 1-hexene; alternatively, at least 95 wt. % 1-hexene; alternatively, at least 97 wt. % 1-hexene; or alternatively, at least 98 wt. % 1-hexene by weight of the ethylene trimer, or from 85 wt. % to 99.9 wt. % 1-hexene; alternatively, from 87.5 wt. % to 99.9 wt. % 1-hexene; alternatively, from 90 wt. % to 99.9 wt. % 1-hexene; alternatively, from 92.5 wt. % to 99.9 wt. % 1-hexene; alternatively, from 95 wt. % to 99.9 wt. % 1-hexene; alternatively, from 97 wt. % to 99.9 wt. % 1-hexene; or alternatively, from 98 wt. % to 99.9 wt. % 1-hexene by weight of the ethylene trimer.

In ethylene oligomerization, ethylene tetramerization, or ethylene trimerization and tetramerization embodiments, the ethylene tetramer can comprise at least 85 wt. % 1-octene; alternatively, at least 87.5 wt. % 1-octene; alternatively, at least 90 wt. % 1-octene; alternatively, at least 92.5 wt. % 1-octene; alternatively, at least 95 wt. % 1-octene; alternatively, at least 97 wt. % 1-octene; or alternatively at least 98 wt. % 1-octene by weight of the ethylene tetramer or from 85 wt. % to 99.9 wt. % 1-octene; alternatively, from 87.5 wt. % to 99.9 wt. % 1-octene; alternatively, from 90 wt. % to 99.9 wt. % 1-octene; alternatively, from 92.5 wt. % to 99.9 wt. % 1-octene; alternatively, from 95 wt. % to 99.9 wt. % 1-octene; alternatively, from 97 wt. % to 99.9 wt. % 1-octene; or alternatively, from 98 wt. % to 99.9 wt. % 1-octene by weight of the ethylene tetramer.

The term "reaction system effluent," and it derivatives (e.g., oligomerization reaction system effluent, trimerization reaction system effluent, tetramerization reaction system effluent, or trimerization and tetramerization reaction system effluent) generally refers to all the material which exits the reaction system through a reaction system outlet/discharge which discharges a reaction mixture and can include reaction system feed(s) (e.g., olefin, catalyst system or catalyst system components, and/or solvent), and/or reaction product (e.g., oligomerization product including oligomers and non-oligomers). The term "reaction system effluent" and its derivatives, can be qualified to refer to certain portions by use of additional qualifying terms. For example, while reaction system effluent refers to all material which exits the reaction system through the reaction system outlet/discharge, a reaction system oligomerization product effluent refers to only the oligomerization product within the reaction system effluent.

The reaction system effluent can be treated and subjected to one or more separation processes to recover components from the reaction system effluent (e.g., unreacted feed(s) solvent, product(s), and/or by-product, among others).

Prior to the recovery of the oligomer, trimer, tetramer, or trimer and tetramer, the reaction system effluent can be contacted with a catalyst system deactivating and quench agent (alternatively, referred to herein as a "catalyst system kill agent" to deactivate and quench the active catalyst system. In an embodiment, the reaction system effluent can be contacted with a catalyst system deactivating agent to at least partially deactivate the catalyst system and then a portion of the reaction system effluent containing the deactivated catalyst system or deactivated catalyst system components can be contacted with a catalyst system quench agent to quench the catalyst system. The catalyst system deactivating and quench agent, catalyst system deactivating agent, and/or catalyst system quench agent can be independently selected from the group consisting of mono-alcohols, diols, polyols, and mixtures thereof. In an embodiment, the catalyst system deactivating and quench agent, catalyst system deactivating agent, and/or catalyst system quench agent can comprise any mono-alcohol, diol, or polyol which is soluble in the reaction system effluent. The mono-alcohol, diol, or polyol can be selected by boiling point, molecular weight, or such that the mono-alcohol, diol, or polyol does not form an azeotrope with the oligomer(s), trimer, and/or tetramer (and/or reaction solvent). In some embodiments, the mono-alcohol, diol, or polyol can have a boiling point different from the oligomer(s), trimer, and/or tetramer (and/or reaction solvent) in the reaction system effluent. In an embodiment, the mono-alcohol can be a $C_4$ to $C_{30}$, $C_4$ to $C_{20}$, or $C_4$ to $C_{12}$ mono-alcohol. In some embodiments, the mono-alcohol can be selected to be easily removable from the oligomer(s), trimer, or tetramer (e.g., 1-hexene in an ethylene trimerization process). Suitable mono-alcohols can comprise 1-hexanol, 2-hexanol, 3-hexanol, 2-ethyl-hexanol, 1-heptanol, 2-heptanol, 3-heptanol, 4-heptanol, 2-methyl-3-heptanol, 1-octanol, 2-octanol, 3-octanol, 4-octanol, 7-methyl-2-decanol, 1-decanol, 2-decanol, 3-decanol, 4-decanol, 5-decanol, 2-ethyl-1-decanol, or mixtures thereof. In one or more specific embodiments, the mono-alcohol can comprise 2-ethyl-1-hexanol.

In an embodiment, the catalyst deactivating and quench agent can be contacted with the reaction system effluent in an amount sufficient to deactivate the catalyst system (i.e., an amount that can inhibit, or halt: (1) production of undesirable solids, i.e., polymer; and/or (2) oligomer(s), trimer, and/or, tetramer) product purity degradation due to isomerization, in subsequent product separation processes and quench the catalyst system (i.e., an amount that can inhibit the pyrophoric nature of residual catalyst components). In these catalyst system deactivation and quench agent embodiments, the catalyst system deactivating and quench agent can be contacted with the reaction system effluent at an alcohol to metal of the metal hydrocarbyl compound (including metal hydrocarbyl compound which can be designated as a halogen containing compound) molar ratio (also referred to as an alcohol to metal molar ratio) up to 100:1; alternatively, up to 50:1; alternatively, up to 25:1; alternatively, up to 10:1; or alternatively, up to 5:1, or from 0.01:1 to 100:1; alternatively, ranging from 0.1:1 to 50:1; or alternatively, ranging from 0.5:1 to 25:1; alternatively, ranging from 0.75:1 to 5:1; alternatively, ranging from 1:1 to 4:1; or alternatively, from 2:1 to 3:1. Additional information about the catalyst system deactivation and quench process are described in U.S. Pat. No. 5,689,028, and U.S. Pat. No. 8,344,198, among other documents.

In an embodiment, the reaction system effluent can be contacted with a catalyst system deactivation agent to at least partially deactivate the catalyst system and later a portion of the reaction system effluent containing the deactivated catalyst system (e.g., a portion remaining after the oligomer, trimer, tetramer, and/or reaction solvent separated from the stream containing the at least partially deactivated catalyst system) can be contacted with the catalyst system quench agent to quench the catalyst system. In these catalyst system deactivating embodiments, the catalyst system deactivating agent can be contacted with the reaction system effluent at a catalyst deactivating agent to metal atoms in the catalyst system compound (including metal hydrocarbyl compound which can be designated as a halogen containing compound) ranging from 0.75:1 to 1.25:1; alternatively, ranging from 0.8:1 to 1.2:1; alternatively, ranging from 0.85:1 to 1.15:1; or alternatively, about 1:1. In these embodiments, the catalyst quench agent can be contacted with a stream containing the at least partially deactivated catalyst system at a catalyst quench agent to metal atoms in the catalyst system compound ranging from 0.5:1 to 1.5:1; alternatively, ranging from 0.7:1 to 1.2:1; alternatively, ranging from 0.8:1 to 1.1:1; or alternatively, about 1:1. Additional information regarding the split catalyst system deactivation and catalyst system quench can be found in U.S. Pat. No. 8,049,052.

After the catalyst system has been deactivated, or deactivated and quenched, the oligomer(s), trimer, tetramer, trimer and tetramer, and/or reaction solvent can be separated from the deactivated or deactivated and quenched reaction system effluent. Any separation process or combination of processes can be used, including, for example, distillation. In one or more embodiments, the separation process can comprise at least one separation vessel selected from columns, tanks, flash vessels, distillation columns, or combinations thereof.

As previously discussed herein, the reaction system effluent can comprise components present in the reaction mixture. For example in an ethylene oligomerization (or alternatively, ethylene trimerization, ethylene tetramerization, or ethylene trimerization and tetramerization), the reaction system effluent generally includes ethylene, the ethylene oligomerization product, (or alternatively, ethylene trimerization product, ethylene tetramerization product, or ethylene trimerization and tetramerization product), the catalyst system (including a transition metal compound, e.g., chromium containing compound, which may or may not be in the same form as the transition metal compound or chromium compound contacted to form the catalyst system), and/or reaction solvent, among other components. A deactivated reaction system effluent and/or deactivated and quenched reaction system effluent generally represents the reaction system effluent which has been contacted with the catalyst system deactivating agent or the catalyst system deactivating quench agent, respectively, that generally comprises ethylene, the ethylene oligomerization product (or alternatively, ethylene trimerization product, ethylene tetramerization product, or ethylene trimerization and tetramerization product), the deactivated or the deactivated and quenched catalyst system (including a transition metal containing compound, e.g., chromium containing compound, and other deactivated or deactivated and quenched catalyst system components), and/or reaction solvent, among other components. In regards to the reaction system effluent, deactivated reaction system effluent, or deactivated and quenched reaction system effluent, the transition metal containing compound, e.g., chromium containing compound, may be the same as (or alternatively, may not be in the same form as) the chromium compound present in the catalyst system prior to reaction As such, the term "transition metal containing compound" or "chromium containing compound" and their derivatives refers to all transition metal compounds or chromium compounds, respectively, regardless of form, that are present in the reaction system effluent, deactivated reaction system effluent, deactivated and quenched reaction system effluent, or reaction system effluent stream (deactivated or deactivated and quenched) which has been processed to remove one or more materials comprising all or a portion of ethylene, the ethylene oligomerization product (or alternatively, ethylene trimerization product, ethylene tetramerization product, or ethylene trimerization and tetramerization product), and/or reaction solvent. The term "transition metal compound" or "chromium compound" and their derivatives refer to transition metal compound or chromium compound, respectively, which are used to form the catalyst system or refer to the transition metal compound or chromium compound, respectively, of the transition metal compound complexed to a heteroatomic ligand or the chromium metal compound complexed to a heteroatomic ligand, respectively, of the catalyst system.

Applicants have unexpectedly discovered that the deactivated reaction system effluent, the deactivated and quench catalyst reaction system effluent, and/or reaction system effluent stream (deactivated or deactivated and quenched) processed to remove one or more materials comprising all or a portion of ethylene, the ethylene oligomerization product (or alternatively, ethylene trimerization product, ethylene tetramerization product, or ethylene trimerization and tetramerization product), and/or the reaction solvent contains one or more transition metal containing species (or alternatively, chromium containing species) which can exhibit pyrophoric behavior. These one or more transition metal containing species (or alternatively, chromium containing species) which exhibit pyrophoric behavior can include transition metal containing solid species (or alternatively, chromium containing solid species). In this patent application the one or more transition metal containing species (or alternatively, chromium containing species) which can exhibit pyrophoric behavior can be referred to as "black solids". The term "black solids" should not be construed to imply that all the transition metal containing species (or alternatively, chromium containing species) which can exhibit pyrophoric behavior are black and/or solid. The term "black solids" is used colloquially to refer to the transition metal species (or alternatively, chromium containing species which can exhibit pyrophoric behavior. As used herein, the term "pyrophoric" refers to a compound capable of spontaneously igniting upon exposure to air and/or oxygen. Without being limited by theory, it is believed that i) during the oligomerization, trimerization, tetramerization, or trimerization and tetramerization, a portion of the transition metal compound (or alternatively, chromium compound) used in the catalyst system, (whether as the transition metal compound or chromium compound used in the catalyst system or as the transition metal compound complexed to a heteroatomic ligand or chromium compound complexed to a heteroatomic ligand), or ii) during the deactivation or deactivation and quenching of the catalyst system in the reaction system effluent a portion of the transition metal compound or the chromium compound used in the catalyst system, (whether as the transition metal compound or chromium compound used in the catalyst system or as the transition metal compound complexed to a heteroatomic ligand or chromium compound complexed to a heteroatomic ligand) can change oxidation state or form a compound which can exhibit pyrophoric behavior when exposed to air or oxygen. Applicants have further unexpectedly found that treating a stream which contains the transition metal containing species or the chromium containing species which exhibit pyrophoric behavior with a beta-diketone can reduce the pyrophoric behavior of the pyrophoric transition metal containing species or the pyrophoric chromium containing species. Without being limited to theory, it is believed that treating a stream containing the pyrophoric transition metal containing species or the pyrophoric chromium containing species with a beta-diketone can change the oxidation state of the pyrophoric transition metal containing species or the pyrophoric chromium containing species to an oxidation state or form a compound which can have a significantly reduced pyrophoric behavior.

In an embodiment, the processes described herein can comprise contacting a transition metal containing compound (or alternatively, a chromium containing compound) with a beta-diketone. In further embodiments, the processes described herein can comprise contacting a transition metal containing compound (or alternatively, a chromium containing compound) with a beta-diketone at conditions capable of changing the oxidation state of the transition metal (or alternatively, chromium). Generally the beta-diketone can be contacted with any stream containing the transition metal compound (or alternatively, the chromium containing compound); e.g., a reaction system effluent, a deactivated reaction system effluent, a deactivated and quenched reaction system effluent, or a reaction system effluent stream (deactivated or deactivated and quenched) which has been processed to remove one or more materials comprising all or a portion of ethylene, the ethylene oligomerization product (or alternatively, ethylene trimerization product, ethylene tetramerization product, or ethylene trimerization and tetramerization product), and/or reaction solvent.

In one or more embodiments, the beta-diketone can be selected from $C_5$ to $C_{30}$ beta-diketones, or $C_5$ to $C_{20}$ beta-diketones, or $C_5$ to $C_{10}$ beta-diketones. As used herein, the term "beta-diketone" refers to a molecule having two ketone groups where the two ketone groups are separated by a carbon atom

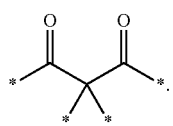

As used herein, the term "ketone" refers to an organic compound having the general group

In one or more specific embodiments, the beta-diketone can be selected from acetylacetone, dibenzoylmethane, dipivaloylmethane, hexafluoroacetylacetone, or combinations thereof. In other embodiments, the beta-diketone can be acetyl acetone; alternatively, dibenzoylmethane; alternatively, dipivaloylniethane; or alternatively, hexafluoroacetylacetone.

In an embodiment, the beta-diketone can have a water content less than 400 ppm, 300, ppm, 200, ppm, 100, ppm, 75 ppm, 50 ppm, 25 ppm, or 10 ppm by weight of the beta-diketone. In some embodiments, the beta-diketone can be contacted with a drying agent prior to contacting the beta-diketone with any stream described herein. In an embodiment, the drying agent can be a molecular sieve (e.g., 3A, 4A, or 5A, among others), alumina, silica gel, or a combination thereof; alternatively, a molecular sieve; alternatively, alumina; or alternatively, silica gel. In other embodiments, the drying agent can be anhydrous sodium sulfate, anhydrous magnesium sulfate, anhydrous calcium sulfate anhydrous potassium carbonate, or any combination thereof.

The beta-diketone can contact the reaction system effluent, deactivated reaction system effluent, deactivated and quenched reaction system effluent, or reaction system effluent stream (deactivated or deactivated and quenched) which has been processed to remove one or more materials comprising all or a portion of ethylene, the ethylene oligomerization product (or alternatively, ethylene trimerization product, ethylene tetramerization product, or ethylene trimerization and tetramerization product), and/or reaction solvent in an amount sufficient to reduce the pyrophoric nature of the transition metal containing compound (or alternatively, chromium containing compound), or in some embodiments, render the transition metal containing compound (or alternatively, chromium containing compound) non-pyrophoric. In an embodiment, the beta-diketone can contact the reaction system effluent, deactivated reaction system effluent, deactivated and quenched reaction system effluent, or reaction system effluent stream (deactivated or deactivated and quenched) which has been processed to remove one or more materials comprising all or a portion of ethylene, the ethylene oligomerization product (or alternatively, ethylene trimerization product, ethylene tetramerization product, or ethylene trimerization and tetramerization product), and/or reaction solvent at a beta-diketone to transition metal (or alternatively, chromium) molar ratio of up to 100:1; alternatively, up to 50:1; alternatively, up to 25:1; alternatively, up to 10:1; or alternatively, up to 5:1, or from 0.01:1 to 100:1; alternatively, ranging from 0.1:1 to 50:1; or alternatively, ranging from 0.5:1 to 25:1; or alternatively, ranging from 0.75:1 to 5:1.

In one or more embodiments, the beta-diketone can contact the reaction system effluent containing the transition metal containing compound (or alternatively, chromium containing compound) prior to first separation (i.e., the beta-diketone contacts the transition metal containing compound or chromium containing compound in the presence of ethylene, the ethylene oligomerization product (or alternatively, ethylene trimerization product, ethylene tetramerization product, or ethylene trimerization and tetramerization product), reaction solvent, and the catalyst system, either active or deactivated).

In other embodiments, the beta-diketone can contact the transition metal containing compound (or alternatively, the chromium containing compound) in a stream within a separation process. It is contemplated that the beta-diketone can contact the transition metal containing compound (or alternatively, the chromium containing compound) within any process stream containing the transition metal containing compound (or alternatively, the chromium containing compound). For example, in one or more specific embodiments, the separation process can comprise separating light boiling components from heavier boiling components present in the reaction system effluent (or deactivated reaction system effluent or deactivated and quenched reaction system effluent) within a first vessel to form a first vessel overhead stream and a first vessel bottoms steam. The first vessel bottoms stream can comprise at least a portion of the transition metal containing compound (or alternatively, the chromium containing compound) and the beta-diketone can contact the transition metal containing compound (or alternatively, the chromium containing compound) in the first vessel bottoms stream. In one or more specific embodiments, the first vessel can be a distillation column, or alternatively, a flash vessel.

In one or more embodiments, the first vessel bottoms stream can be passed to a second vessel adapted to separate the components therein and form a second vessel overhead stream and a second vessel bottom stream. The second vessel bottoms stream can comprise at least a portion of the transition metal containing compound (or alternatively, the chromium containing compound) and the beta-diketone can contact the transition metal containing compound (or alternatively, the chromium containing compound) in the second vessel bottoms stream (whether not the stream entering the second vessel has been contacted with the beta-diketone). In one or more specific embodiments, the second vessel can be a distillation column, or alternatively, a flash vessel.

In one or more embodiments, the second vessel bottoms stream can be passed to a third vessel adapted to separate the components therein and form a third vessel overhead stream and a third vessel bottoms stream. The third vessel bottoms stream can comprise at least a portion of the transition metal containing compound (or alternatively, chromium containing compound) and the beta-diketone can contact the transition metal containing compound (or alternatively, chromium containing compound) in the third vessel bottoms stream (whether not the stream entering the second vessel has been contacted with the beta-diketone). In one or more specific embodiments, the second vessel can be a distillation column, or alternatively, a flash vessel. Alternatively, the beta-diketone can contact the transition metal containing compound (or alternatively, the chromium containing compound) in the reaction system effluent (and/or the deactivated reaction system effluent and/or the deactivated and quenched reaction system effluent), the first vessel bottoms stream, the second vessel bottoms stream, the third vessel bottoms stream, the storage vessel or combinations thereof.

In yet other embodiments, the beta-diketone can contact the transition metal containing compound (or alternatively, the chromium containing compound) after the separation process (e.g., the bottoms stream of the last separation process flash vessel or distillation column or alternatively, in a storage vessel for the final stream that can comprise the transition metal containing compound or alternatively chromium containing compound). For example, at least a portion of the reaction system effluent (either prior, during or after separation) can be passed to a storage vessel and the beta-diketone can contact the transition metal containing compound (or alternatively, the chromium containing compound) within the storage vessel.

Further, the beta-diketone can contact the transition metal containing compound (or alternatively, the chromium containing compound) in the presence of a catalyst system deactivating and quench agent, catalyst system deactivating agent and/or catalyst system quench agent. In an embodiment, the beta-diketone can be a component of the catalyst system deactivating agent which contacts the reaction system effluent. In some embodiment, the beta-diketone can be a component of the catalyst system deactivating and quench agent which contacts the reaction system effluent. In other embodiments, the beta-diketone can be contacted with the deactivated reaction system effluent, or alternatively, contacted with the deactivated and quenched reaction system effluent. In some embodiment, the beta-diketone can be a component of the catalyst system quench agent; or alternatively, the beta-diketone can be contacted with a separation process stream in which the catalyst system has been quenched.

In one or more embodiments, the beta-diketone can be introduced to the reaction system effluent essentially simultaneously with the catalyst system deactivating agent, catalyst system deactivating and quench agent, or catalyst system quench agent. In other embodiments, the beta-diketone can be a component in the catalyst system quench composition, the catalyst system deactivation and quench composition, or the catalyst system quench composition. Alternatively, the beta-diketone can contact the transition metal containing compound (or alternatively, the chromium containing compound) subsequent to catalyst system deactivation, catalyst system deactivation and quench, or catalyst system quench.

In an embodiment, the beta-diketone can contact the reaction system effluent comprising the transition metal containing compound (or alternatively, the chromium containing compound) prior to contact of the reaction system effluent with the catalyst system deactivating agent or catalyst system deactivating and quench agent. In some embodiments, the beta-diketone can contact the reaction system effluent comprising the transition metal containing compound (or alternatively, the chromium containing compound) subsequent to contact of the reaction system effluent with a catalyst deactivating agent or catalyst system deactivating and quench agent. In other embodiments, the beta-diketone can contact the deactivated reaction system effluent comprising the transition metal containing compound (or alternatively, the chromium containing compound) subsequent to contact of the reaction system effluent with a catalyst deactivating agent but prior to contact of a stream comprising the transition metal containing compound (or alternatively, the chromium containing compound) with the catalyst system quench agent.

Returning to the figures, FIGS. 7-17 illustrate potential separation systems 700, 800, 900, 1000, 1200, 1300, 1400, 1500, 1600, and 1700 which can be utilized in the processing of a reaction system effluent as described herein. Separation systems 700, 800, 900, 1000, 1200, 1300, 1400, 1500, 1600, and 1700 can be discussed in terms of a separation system for the processing of a reaction system effluent from an ethylene trimerization process. However, one having ordinary skill in the art can readily recognize that separation systems 700, 800, 900, 1000, 1200, 1300, 1400, 1500, 1600, and 1700 can be readily adapted to the separation system for the processing of a reaction system effluent from an ethylene tetramerization process or an ethylene trimerization and tetramerization process. Additionally, the techniques described herein to deactivate the catalyst system, deactivate and quench the catalyst system, and quench the catalyst system in combination with the introduction of beta-diketones can be used with number of chemical processes. For example, other types of oligomerization reaction systems and reaction systems for other types of chemical products can use separation systems that deactivate, deactivate and quench, or quench a catalyst system of a reaction system effluent that can use a beta-diketone as depicted in and discussed for separation systems 700, 800, 900, 1000, 1200, 1300, 1400, 1500, 1600, and 1700. The use of these other types of oligomerization reaction systems for other types of chemical products separation systems that deactivate, deactivate and quench, or quench a catalyst system in a reaction system effluent are considered to be within the scope of the present invention.

Figure 7:
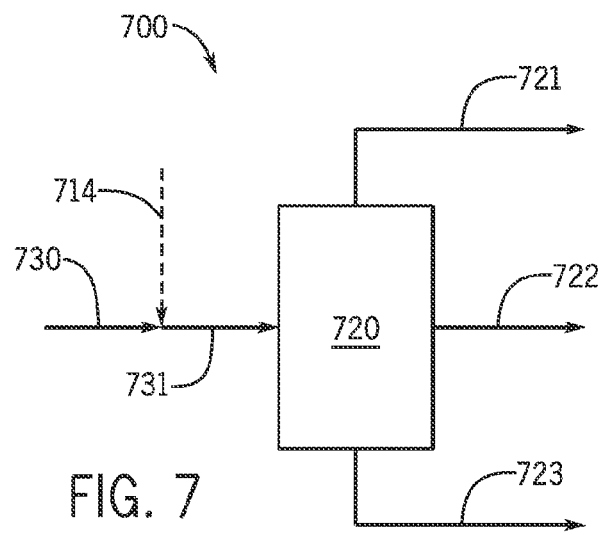
FIGS. 7-17 illustrate embodiments of a separation system.

Referring to FIG. 7, the diagram depicts separation system 700 used to separate components in a reaction system effluent 730 from a reaction system (not shown). Separation system 700 contacts a catalyst system deactivation and quench agent 714 with the reaction system effluent 730 to form catalyst system deactivated and quenched reaction system effluent 731, which then enters fractionation column 720 and is processed into i) an overhead stream 721, ii) a side stream 722, and iii) a bottoms stream 723.

In relation to ethylene trimerization, the reaction system effluent 730 can comprise ethylene, trimerization product (including light trimerization co-products, trimer, and heavy trimerization co-products), catalyst system and/or catalyst system components, and reaction solvent while the catalyst system deactivated and quenched reaction system effluent 731 can comprise ethylene, trimerization product (including light trimerization co-products, trimer, and heavy trimerization co-products), deactivated and quenched catalyst system and/or catalyst system components, and reaction solvent. In relation to the catalyst system deactivated and quenched reaction system effluent 731, fractionation column 720 provides i) an overhead stream 721 comprising ethylene and light trimerization co-products (trimerization product components having a boiling point less than the trimer), ii) a side stream 722 comprising trimer and reaction solvent, and iii) a bottoms stream 723 comprising heavy trimerization co-products (trimerization product components having a boiling point greater than the trimer), and deactivated and quenched catalyst system and/or catalyst system components. Side stream 722 can be further processed (not depicted) to separate the reaction solvent from the trimer and to optionally recycle the reaction solvent for re-use in the trimerization reactor. Overhead stream 721 can be further processed (not depicted) to isolate and/or purify the ethylene for recycle to the trimerization reactor. Bottoms stream 723 can be further processed (not depicted) to separate one or more heavy trimerization co-product streams from the deactivated and quenched catalyst system and/or catalyst system components.

The fractionation column 720 can be a continuous distillation column with separation stages comprised of trays, packing material, or combinations thereof. Fractionation column 720 can be operated by recycling a portion of the bottoms stream 723 back to the fractionation column 720 through a reboiler (not shown). In that example, the reboiler (i.e., heat exchanger) can be externally heated with heat transfer fluid, such as steam. Moreover, a portion of the overhead stream 721 can be condensed and returned to the fractionation column 720 as reflux (not shown). In certain embodiments, an accumulator vessel, reflux drum, and/or reflux pumps can facilitate introduction of the portion of overhead stream 721 utilized as reflux to the fractionation column 720.

The catalyst system deactivation and quench agent 714 can be stored in a vessel for addition to the process. In some embodiments, water and other contaminants can be removed from the catalyst system deactivation and quench agent 714 in a dryer (not shown). The addition of the catalyst system deactivation and quench agent 714 to the trimerization reaction system effluent 730 can take place near a control valve, for example, to facilitate mixing of the catalyst system deactivation and quench agent 714 with the reaction system effluent 730. In one example, the catalyst system deactivation and quench agent 714 can be injected downstream of a pressure control valve of the trimerization reaction system. In another example, the catalyst system deactivation and quench agent 714 can be added immediately upstream of the pressure control valve. However, for injection of the catalyst system deactivation and quench agent 714 upstream of a valve, the valve should typically be sufficiently isolated from the trimerization reaction system to prevent contamination, e.g., at the end of a leg or pipe coming from the trimerization reaction system. In these examples, the reaction system effluent 730 can flash across a control valve and can create turbulence which can assist in the mixing of the catalyst system deactivation and quench agent 714 with the reaction system effluent 730. The quantity of catalyst system deactivation and quench agent 714 injected can be controlled by a compound addition control valve. The catalyst system deactivation and quench agent 714 addition control valve can be adjusted based on the flow rate of catalyst system into the reaction system to maintain a desired proportion or ratio of the catalyst system deactivation and quench agent 714 to metals in the catalyst system.

In separation system 720, the beta-diketone can be contacted with the transition metal containing compound (or alternatively, chromium containing compound) in any one or more of streams within separation system 720 including i) the reaction system effluent 730 prior to contact with the catalyst system deactivating and quench agent 714, ii) the reaction system effluent 730 simultaneous with the contact of the catalyst system deactivating and quench agent 714, iii) the catalyst system deactivated and quenched reaction system effluent 731 prior to entering fractionation column 720, and iv) the bottoms stream 723 (either in the reboiler of the fraction column 720 or after the bottoms stream exits the fractionation column 720). Alternatively, or additionally, the beta-diketone can be contacted with the transition metal containing compound (or alternatively, chromium containing compound) present in other process streams within the separation system (e.g., a bottoms downstream storage tank, among others places).

Figure 8:
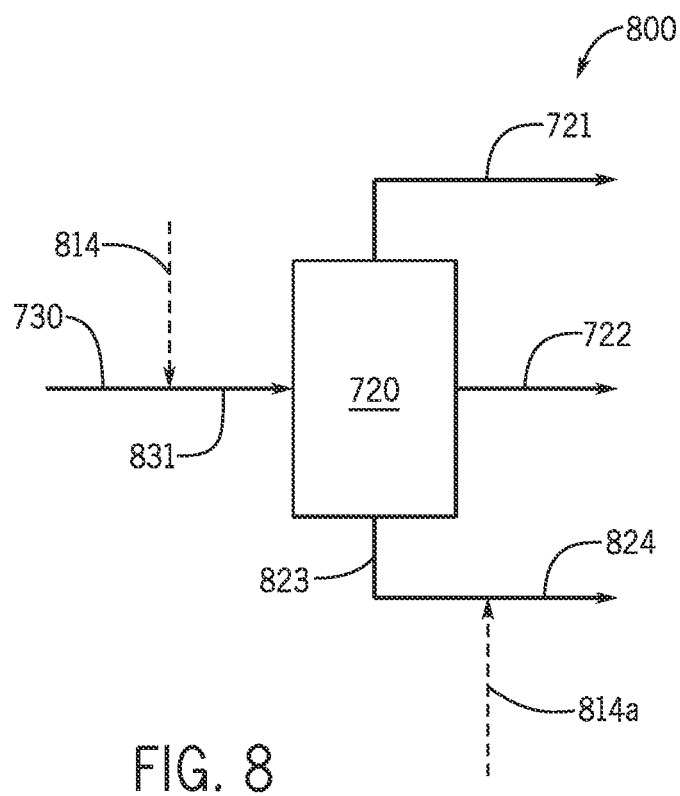

Referring to FIG. 8, the diagram depicts separation system 800 used to separate components in reaction system effluent 730 from a reaction system (not shown). Separation system 800 differs from separation system 700 in that the catalyst system deactivation and quench agent addition is separated into two distinct steps. Specifically, catalyst system deactivation agent 814 is added to reaction system effluent 730 to form catalyst system deactivated reaction system effluent 831 which enters fractionation column 720 and is processed into i) overhead stream 721, ii) side stream 722, and iii) bottoms stream 823 which is then contacted with catalyst system quench agent 814a to form quenched stream 824. Within separation system 800, equipment and streams having the same number designation as those in separation system 700 can operate, can be processed, can have the same compositions, and/or can have the same options described for processing streams as described for the separation system 700 equipment and streams with the exception that the catalyst system deactivated and quenched streams and components/compositions prior to the addition of the catalyst system quench agent are catalyst system deactivated streams and components/compositions. Specifically, a) deactivated reaction system effluent stream 831 can comprise can comprise ethylene, trimerization product (including light trimerization co-products, trimer, and heavy trimerization co-products), deactivated catalyst system and/or catalyst system components, and reaction solvent, b) bottoms stream 823 can comprise heavy trimerization co-products (trimerization product components having a boiling point greater than the trimer), and deactivated catalyst system and/or catalyst system components, and c) fractionation column 720 can be operated by recycling a portion of the bottoms stream 823 back to the fractionation column 720 through a reboiler (not shown). Finally, bottoms stream 824 can comprise heavy trimerization co-products (trimerization product components having a boiling point greater than the trimer), and deactivated and quenched catalyst system and/or catalyst system components (which may or may not be the same as the deactivated and quenched catalyst system and/or catalyst system components of bottoms stream 723 of separation system 700) which can be further processed (not depicted) to separate one or more heavy trimerization co-product streams from the deactivated and quenched catalyst system and/or catalyst system components.

The catalyst system deactivation agent 814 and/or catalyst system quench agent 814a can be stored in a vessel for addition to the process. In some embodiments, water and other contaminants can be removed from the catalyst system deactivation agent 814 and catalyst system 814a in a dryer. When the deactivation agent 814 and the catalyst system quench agent 814a are the same, they can be supplied by a common storage vessel. The addition of the catalyst system deactivation agent 814 to the trimerization reaction system effluent 730 can take place near a control valve, for example, to facilitate mixing of the catalyst system deactivation agent 814 with the reaction system effluent 730. In one example, the catalyst system deactivation agent 814 can be injected downstream of a pressure control valve of the trimerization reaction system. In another example, the catalyst system deactivation agent 814 can be added immediately upstream of the pressure control valve. However, for injection of agent 814 upstream of a valve, the valve should typically be sufficiently isolated from the trimerization reaction system to prevent contamination, e.g., at the end of a leg or pipe coming from the trimerization reaction system. In these examples, as the reaction system effluent 730 flashes across a control valve, the resulting turbulence can assist the mixing of the catalyst system deactivation agent 814 with the reaction system effluent 730. The quantity of catalyst system deactivation agent 814 injected can be controlled by a catalyst system deactivation addition control valve. The catalyst system deactivation agent addition control valve can be adjusted based on the rate of catalyst system flow into the reactor, maintaining the proportion or ratio of the catalyst system deactivation agent 814 to metals in the catalyst system. The catalyst system quench agent 814a can be added to the bottoms stream 823 or at other downstream points. The catalyst system quench agent 814a can be added near a control valve to facilitate mixing, near a reboiler (not depicted) on the bottoms stream 823 of column 720, and so on. The amount of catalyst system quench agent 814a added can be adjusted based on the amount of catalyst system added to the upstream trimerization reaction system, a flow rate of the bottoms stream 823, the flow rate of catalyst system deactivation agent 814, and so forth.

In separation system 800, the beta-diketone can be contacted with the transition metal containing compound (or alternatively, the chromium containing compound) at any one or more streams within the separation system including i) the reaction system effluent 730 prior to contact with the catalyst system deactivation agent 814, ii) the reaction system effluent 730 simultaneous with the contact of the catalyst system deactivation agent 814, iii) the catalyst system deactivated reaction system effluent 831 prior to entering fractionation column 720, iv) bottoms stream 823 prior to with the catalyst system quench agent, v) bottoms stream 823 simultaneous with the contact of bottoms stream 823 with the catalyst system quench agent 814a, and vi) quenched bottoms stream 824. Alternatively, or additionally, the beta-diketone can be contacted with the transition metal containing compound (or alternatively, chromium containing compound) present in other process streams within the separation system (e.g., a downstream heavies storage tank, among others).

Figure 9:
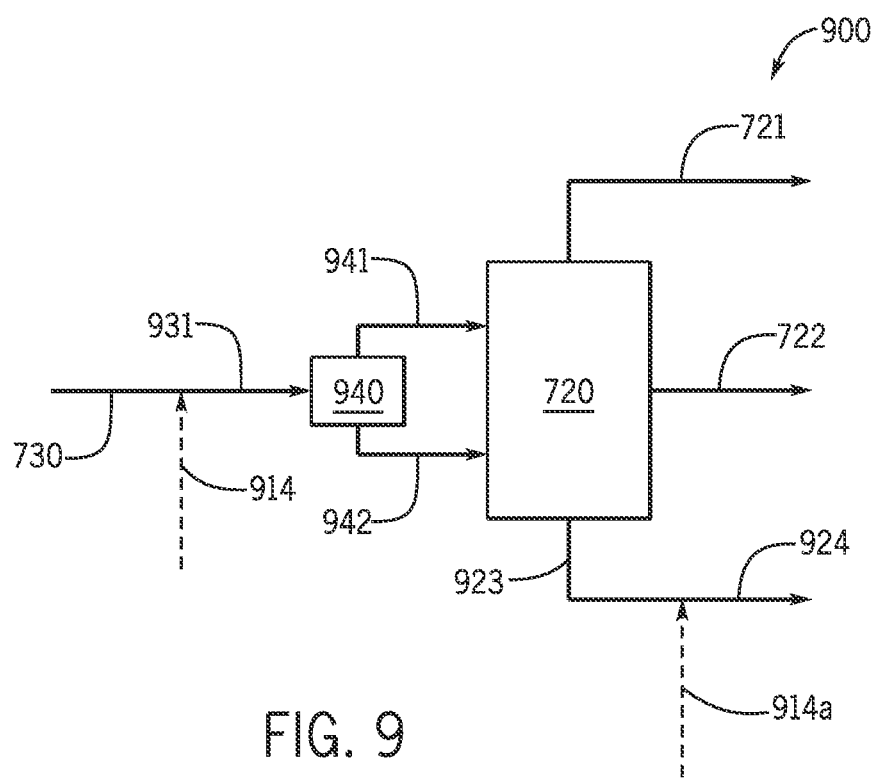

Referring to FIG. 9, the diagram depicts separation system 900 used for separation of reaction system effluent 730 from a reaction system (not shown). Separation system 900 includes a flash drum 940 (or vapor/liquid separator) prior to the fractionation tower 720 that can be added to separation system 700 or separation system 800. In separation system 900, the process flow can be configures with the option of i) contacting the reaction system effluent with a catalyst system deactivating and quench agent 914 to form a catalyst system deactivated and quenched reaction system effluent 931 (having the composition of deactivated and quenched reaction system effluent stream 731) and ultimately forming column 720 bottom stream 923 (having the composition of bottoms stream 723) or ii) contacting the reaction system effluent 730 with a catalyst system deactivation agent 914 to form a catalyst system deactivated reaction system effluent 931 (having the composition of deactivated reaction system effluent stream 831), and ultimately forming column 720 bottoms stream 923 (having the composition of bottoms stream 823) which can then be contacted with catalyst system quench agent 914a (shown as an optional addition) to form quenched stream 924 (having the same composition as bottoms stream 824 which may or may not be the same as bottoms stream 923/723 resulting from the produced in option i)). Separation system 900 differs from separation system 700 and separation system 800 in that deactivated and quenched reaction system effluent or deactivated reaction system effluent stream 931 can enter a flash drum 940 prior to entering the fractionation column 720. Flash drum 940 separates catalyst system deactivated and quenched reaction system effluent or catalyst system deactivated reaction system effluent 931 into a vapor stream 941 and a liquid stream 942. Vapor stream 941 and liquid stream 942 can be introduced into the fractionation column 720 at the appropriate locations. Employment of a flash drum 940 can improve the efficiency of fractionation column 720. Within separation system 900, equipment and streams having the same number designation as those in separation system 700 and/or 800 can operate, can be processed, can have the same compositions, and/or can have the same options described for processing streams as described for the separation system 700 and/or 800 equipment and streams. Additionally, options described for processing streams through fractionation column 720 and/or 720 (e.g., utilization of recycle streams, accumulator vessels, reflux drums, and/or reflux pumps among others) can also be utilized the appropriate situations for fractionation column 720 of separation system 900.

In separation system 900, the beta-diketone can be contacted with the transition metal containing compound (or alternatively, chromium containing compound) in any one or more streams within the separation system including i) the reaction system effluent 730 prior to contact with the catalyst system deactivation and quench agent or catalyst system deactivation agent 914, ii) the reaction system effluent 730 simultaneous with the contact of the catalyst system deactivation and quench agent or catalyst system deactivation agent 914, iii) the catalyst system deactivated and quenched reaction system effluent or catalyst system deactivated reaction system effluent 931 prior to entering flash drum 940, iv) flash drum liquid stream 942 prior to entering fractionation column 720, v) bottoms stream 923 prior to contacting the bottoms stream 923 with the optional catalyst system quench agent 914a (e.g., when the reaction system effluent 730 is only contacted with the catalyst system deactivation agent 914), vi) bottoms stream 923 simultaneous with the contact of the bottoms stream 923 with the optional catalyst system quench agent 914a (e.g., when the reaction system effluent 730 is only contacted with the catalyst system deactivation agent 914), and vii) quenched bottoms stream 924 (e.g., when the reaction system effluent 730 is only contacted with the catalyst system deactivation agent 914). Alternatively, or additionally, the beta-diketone can be contacted with the transition metal containing compound (or alternatively, chromium containing compound) present in other process streams within the separation system (e.g., a downstream heavies storage tank, among others).

Figure 10:
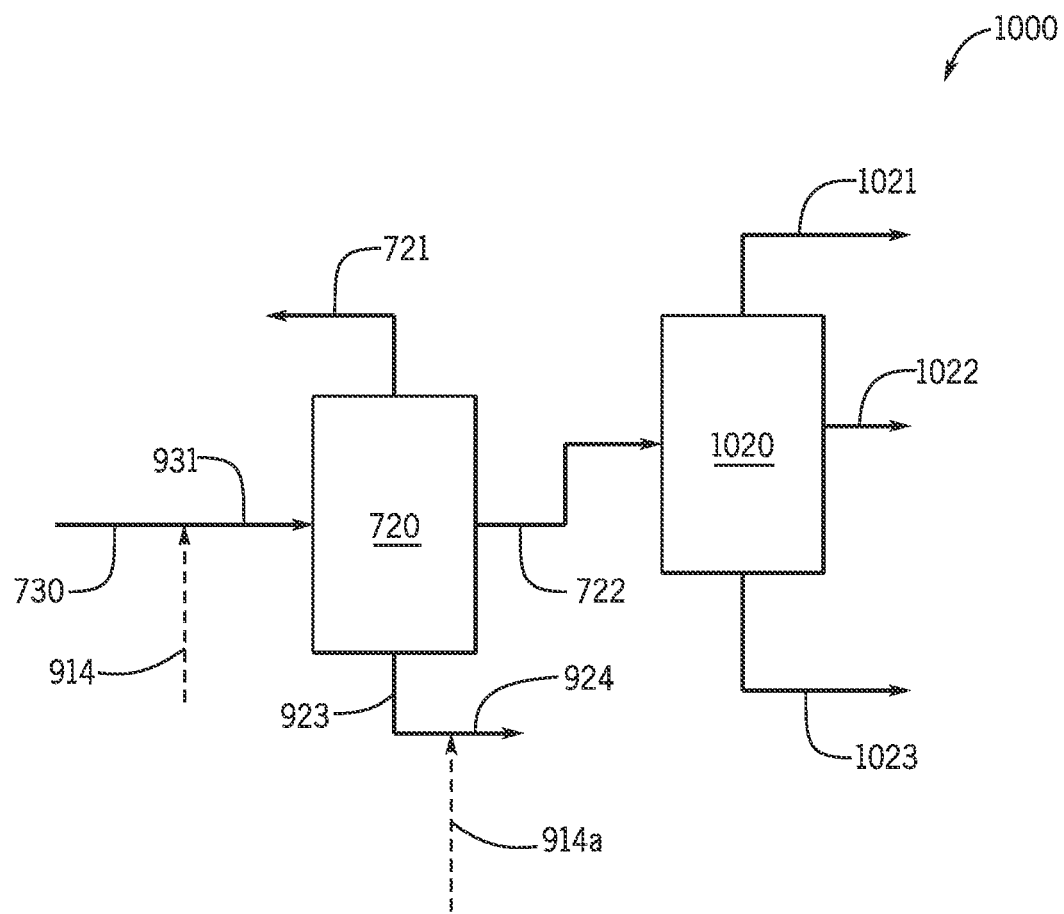

Referring to FIG. 10, the diagram depicts a separation system flow depicting a separation system 1000 for the separation of the components in a reaction system effluent 730 from a reaction system. Separation system 1000 includes a fractionation column 1020, which can be added to separation system 720 (in any of the embodiments depicted in FIGS. 7-9). Within separation system 1000, equipment and streams having the same number designation as those in separation system 700, 800, and/or 900 can operate, can be processed, can have the same compositions, and/or can have the same options described for processing streams through fractionation column 720 as described for the separation system 700, 800, and/or 900 equipment and streams. Separation system 1000 differs from separation systems 700, 800 and 900 in that side stream 722 can enter a fractionation column 1020. In an embodiment, fractionation column 1020 can separate the side stream 722 into an overhead stream 1021 (at least a portion of which may or may not be recycled back to fractionation column 720), a side stream 1022 comprising the reaction solvent (which may or may not be recycled back the reaction system with or without additional processing), and a bottoms stream 1023 comprising the product (e.g., trimer). In another embodiment, fractionation column 1020 can separate the side stream 722 into an overhead stream 1021 (at least a portion of which may or may not be recycled back to fractionation column 720), a side stream 1022 comprising the product (e.g., trimer), and a bottoms stream 1023 comprising reaction solvent (which may or may not be recycled back the reaction system with or without additional processing). In yet other embodiments, separation system 1000 can further employ a flash drum 940 as depicted in FIG. 9 (not shown) to separate a catalyst system deactivated and quenched reaction system effluent or a deactivated catalyst system reaction system effluent into a vapor stream 941 (not shown) and a liquid stream 942 (not shown). The vapor stream 941 (not shown) and the liquid stream 942 (not shown) from the flash drum 940 can be introduced into the fractionation column 720 at the appropriate locations. Employment of a flash drum 940 (not shown) can improve the efficiency of column 720.

The fractionation column 1020 can be a continuous distillation columns with separation stages comprised of trays, packing material, or combinations thereof. Fractionation column 1020 can be operated by recycling a portion of bottoms stream 1023 back to the fractionation column 1020 through a reboiler (not shown). In that example, the reboiler (i.e., heat exchanger) can be externally heated with heat transfer fluid, such as steam. Moreover, a portion of the overhead stream 1021 can be condensed and returned to the fractionation column 1020 as reflux (not shown). In certain embodiments, an accumulator vessel, reflux drum, and/or reflux pumps can facilitate introduction of the portion of overhead stream 1021 utilized as reflux to the fractionation column 1020.

In separation system 1000, the beta-diketone can be contacted with the transition metal containing compound (or alternatively, chromium containing compound) in any one or more streams within separation system including i) the reaction system effluent 730 prior to contact with the catalyst system deactivation and quench agent or catalyst system deactivation agent 914, ii) reaction system effluent 730 simultaneous with the contact of catalyst system deactivation and quench agent or catalyst system deactivation agent 914, iii) the catalyst system deactivated and quenched reaction system effluent or catalyst system deactivated reaction system effluent 931 prior to entering fractionation column 720, iv) the catalyst system deactivated and quenched reaction system effluent or catalyst system deactivated reaction system effluent 931 prior to entering fractionation column 720 or optional flash drum 940 (not shown), v) flash drum bottoms stream 942 (not shown) prior to entering fractionation column 720, vi) bottoms stream 923 prior to contacting the bottoms stream 923 with the optional catalyst system quench agent 914a, vii) bottoms stream 923 simultaneous with the contact of the bottoms stream 923 with the optional catalyst system quench agent 914a, and viii) quenched bottoms stream 924. Alternatively, or additionally, the beta-diketone can be added to the transition metal containing compound (or alternatively, chromium containing compound) present in other process streams within the separation system (e.g., a downstream heavies storage tank, among others).

Figure 11:
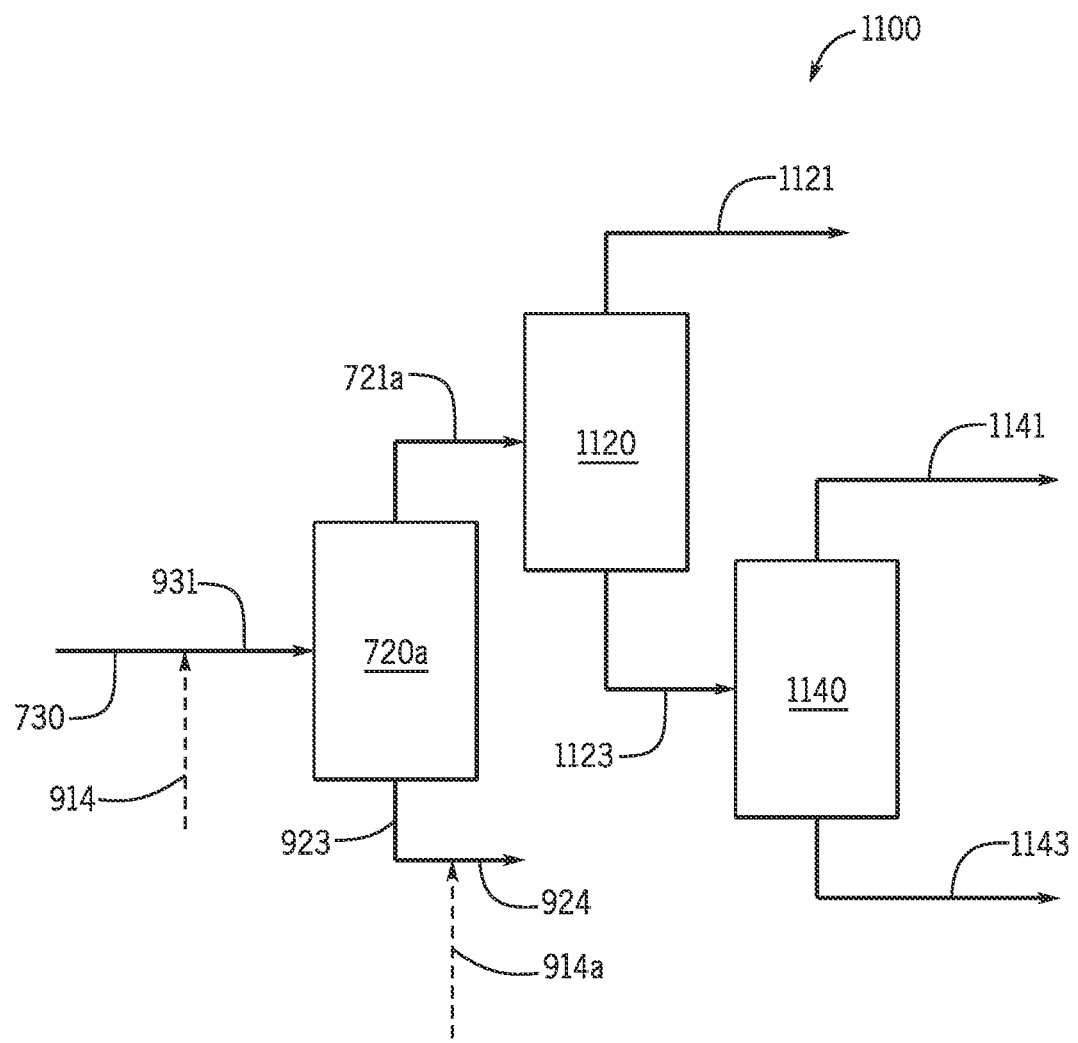

Referring to FIG. 11, the diagram depicts a separation system flow depicting a separation system 1100 for the separation of the components in reaction system effluent 730 from a reaction system. Within separation system 1100, equipment and streams having the same number designation as those in separation system 700, 800, 900, and/or 1000 can operate, can be processed, can have the same compositions, and/or can have the same options described for processing streams as described for the separation system 700, 800, 900 and/or 1000 equipment and streams. In comparison to separation system 700, 800, 900, and 1000, fractionation column 720a is configured without a product side draw. Instead, fractionation column 720a provides i) an overhead stream 721a comprising ethylene, light trimerization co-products (trimerization product components having a boiling point less than the trimer), trimer and reaction solvent, and ii) a bottoms stream 923 comprising heavy trimerization co-products (trimerization product components having a boiling point greater than the trimer) and deactivated and quenched or quenched catalyst system and/or catalyst system components. Overhead stream 721a can then be separated by fractionation column 1120 into a) an overhead stream 1121 comprising ethylene and light trimerization co-products (trimerization product components having a boiling point less than the trimer) and b) bottoms stream 1123 comprising trimer and reaction solvent. Bottoms stream 1123 can then be fed to fractionation column 1140. In one embodiment, fractionation column 1140 can provide i) overhead stream 1141 comprising trimer and ii) bottoms stream 1143 comprising reaction solvent (which may or may not be recycled back the reaction system with or without additional processing). In another embodiment, fractionation column 1140 provides i) overhead stream 1141 comprising reaction solvent (which may or may not be recycled back the reaction system with or without additional processing) and ii) bottoms stream 1143 comprising trimer. In some embodiments, fractionation column 1120 can be operated as having a side stream withdraw (not shown) which can be utilized in a manner where stream 1121 comprises ethylene and the side stream comprises light trimerization co-products. In yet other embodiments, separation system 1100 can further employ a flash drum 940 as depicted in FIG. 9 (not shown) to separate a catalyst system deactivated and quenched reaction system effluent or a deactivated catalyst system reaction system effluent into a vapor stream 941 (not shown) and a liquid stream 942 (not shown). The vapor stream 941 (not shown) and the liquid stream 942 (not shown) from the flash drum 940 can be introduced into the fractionation column 720a at the appropriate locations. Employment of a flash drum 940 (not shown) can improve the efficiency of column 720a.

Fractionation columns 721a, 1120, and 1140 can be continuous distillation columns with separation stages comprised of trays, packing material, or combinations thereof. A portion of the overhead stream 721a can be condensed and returned to the fractionation column 720a as reflux (not shown). Fractionation column 1120 can be operated by recycling a portion of bottoms stream 1123 back to the fractionation column 1120 through a reboiler (not shown). A portion of the overhead stream 1121 can be condensed and returned to the fractionation column 1120 as reflux (not shown). A portion of overhead stream 1121 can be further processed (not depicted) to isolate and/or purify the ethylene for recycle to the trimerization reactor. Fractionation column 1140 can be operated by recycling a portion of bottoms stream 1143 back to the fractionation column 1140 through a reboiler (not shown). A portion of the overhead stream 1141 can be condensed and returned to the fractionation column 1140 as reflux (not shown). The reboilers (i.e., heat exchangers) which can be utilized in the recycling of a portion of 1123, and/or 1143 to their respective fractionation column can be externally heated with heat transfer fluid. In an embodiment, accumulator vessels, reflux drums, and/or reflux pumps can facilitate introduction of the portion of the overhead stream 721a, 1121, and/or 1141 utilized as reflux to their respective fractionation column.

It is contemplated that the beta-diketone can be contacted with the transition metal containing compound (or alternatively, chromium containing compound) in any one or more streams within separation system such as those described in separation system 700, 800, 900, and/or 1000. Alternatively, or additionally, the beta-diketone can be added to the transition metal containing compound (or alternatively, chromium containing compound) present in other process streams within the separation system (e.g., a downstream heavies storage tank, among others) illustrated in separation system 1100.

Figure 12:
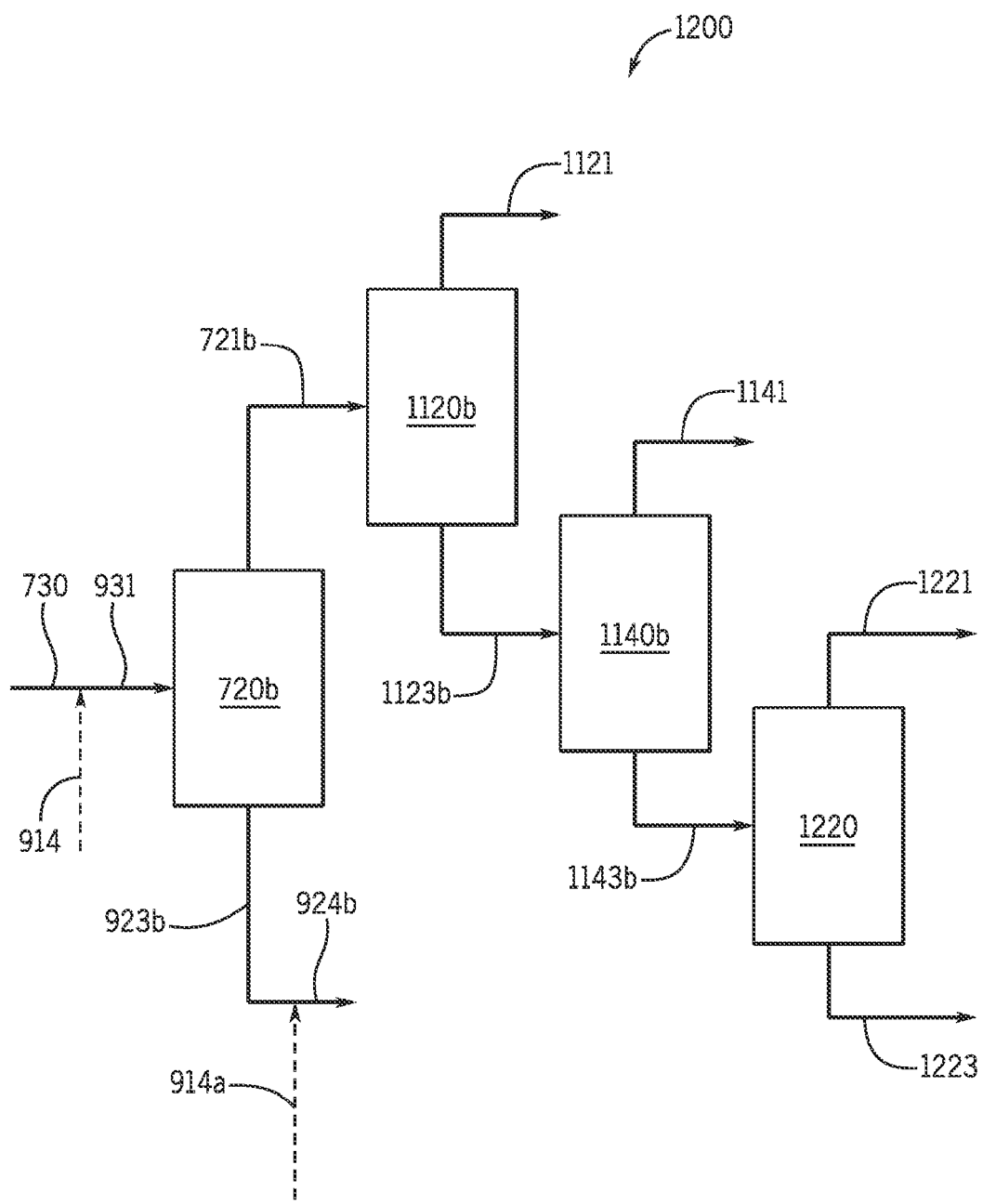

FIG. 12 depicts separation system 1200 used to separate components in a reaction system effluent 730 from a reaction system (not shown). Separation system 1200 has the option of i) contacting the reaction system effluent with a catalyst system deactivating and quench agent 914 to form a catalyst system deactivated and quenched reaction system effluent 931 (having the composition of a deactivated and quenched reaction system effluent stream 731) or ii) contacting the reaction system effluent 730 with a catalyst system deactivation agent 914 to form a catalyst system deactivated reaction system effluent 931 (having the composition of deactivated reaction system effluent stream 831). Catalyst system deactivated and quenched reaction system effluent or catalyst system deactivated reaction system effluent 931 can then be separated by fractionation column 720b into overhead stream 721b comprising ethylene, light trimerization co-products (trimerization product components having a boiling point less than the trimer), trimer, reaction solvent, and at least a portion of the liquid heavy trimerization co-products (liquid trimerization product components having a boiling point greater than trimer heavy trimerization co-product) and bottoms stream 923b comprising at least a portion of solid heavy trimerization co-products and deactivated and quenched or quenched catalyst system and/or catalyst system components. Fractionation column bottoms stream 923b can then be contacted with catalyst system quench agent 914a (shown as an optional addition), e.g., when reaction system effluent stream 730 is contacted with a catalyst system deactivation agent, to form quenched stream 924b (comprising at least a portion of the solid heavy trimerization co-products and deactivated and quenched catalyst system and/or catalyst system components). Fractionation column 720a overhead stream 721b can then be separated by fractionation column 1120b into a) an overhead stream 1121 comprising ethylene and light trimerization co-products (trimerization product components having a boiling point less than the trimer), and b) a bottoms stream 1123b comprising trimer, reaction solvent, and the at least a portion of the liquid heavy trimerization co-products. Bottoms stream 1123b can then be fed to fractionation column 1140b. In one embodiment, fractionation column 1140b can provide i) overhead stream 1141 comprising trimer and ii) bottoms stream 1143b comprising reaction solvent and the at least a portion of the liquid heavy trimerization co-products which can then be separated by fractionation column 1220 into a) an overhead stream 1221 comprising reaction solvent (which may or may not be recycled back the reaction system with or without additional processing) and b) a bottoms stream 1223 comprising the at least a portion of the liquid heavy trimerization co-products. In another embodiment, fractionation column 1140b can provide i) overhead stream 1141 comprising reaction solvent (which may or may not be recycled back the reaction system with or without additional processing) and ii) bottoms stream 1143b comprising trimer and the at least a portion of the liquid heavy trimerization co-products which can then be separated by fractionation column 1220 into a) an overhead stream 1221 comprising trimer and b) a bottoms stream 1223 comprising the at least a portion of the liquid heavy trimerization co-products. Overhead stream 1121 can be further processed (not depicted) to isolate and/or purify the ethylene for recycle to the trimerization reactor. In some embodiments, fractionation column 1120b can be operated as having a side stream withdraw (not shown) which can be utilized in a manner where stream 1121 comprises ethylene and the side stream comprises light trimerization co-products. In yet other embodiments, separation system 1200 can further employ a flash drum 940 as depicted in FIG. 9 (not shown) to separate a catalyst system deactivated and quenched reaction system effluent or a deactivated catalyst system reaction system effluent into a vapor stream 941 (not shown) and a liquid stream 942 (not shown). The vapor stream 941 (not shown) and the liquid stream 942 (not shown) from the flash drum 940 can be introduced into the fractionation column 720b at the appropriate locations. Employment of a flash drum 940 (not shown) can improve the efficiency of column 720b.

Fractionation columns 721b, 1120b, 1140b, and 1220 can be continuous distillation columns with separation stages comprised of trays, packing material, or combinations thereof. Fractionation column 721b can be operated by recycling a portion of bottoms stream 923b back to the fractionation column 720b through a reboiler (not shown). A portion of the overhead stream 721a can be condensed and returned to the fractionation column 720a as reflux (not shown). Fractionation column 1120b can be operated by recycling a portion of bottoms stream 1123b back to the fractionation column 1120b through a reboiler (not shown). A portion of the overhead stream 1121a can be condensed and returned to the fractionation column 1120b as reflux (not shown). In an embodiment, overhead stream 1121 can be further processed (not depicted) to isolate and/or purify the ethylene for recycle to the trimerization reactor. Fractionation column 1140b can be operated by recycling a portion of bottoms stream 1143b back to the fractionation column 1140b through a reboiler (not shown). A portion of the overhead stream 1141 can be condensed and returned to the fractionation column 1140b as reflux (not shown). Fractionation column 1220 can be operated by recycling a portion of bottoms stream 1223 back to the fractionation column 1220 through a reboiler (not shown). A portion of the overhead stream 1221 can be condensed and returned to the fractionation column 1220 as reflux (not shown). The reboilers (i.e., heat exchangers) which can be utilized in the recycling of a portion of 923b, 1123b, 1143b, and/or 1223 to their respective fractionation column can be externally heated with heat transfer fluid. In an embodiment, an accumulator vessel, reflux drum, and/or reflux pump, can facilitate introduction of the portion of overhead stream 721b, 1121, 1141, and/or 1221 utilized as reflux to their respective fractionation column.

In separation system 1200, the beta-diketone can be contacted with the transition metal containing compound (or alternatively, chromium containing compound) in any one or more streams within separation system including i) the reaction system effluent 730 prior to contact with the catalyst system deactivation and quench agent or catalyst system deactivation agent 914, ii) the reaction system effluent 730 simultaneous with the contact of the catalyst system deactivation and quench agent or catalyst system deactivation agent 914, iii) the catalyst system deactivated and quenched reaction system effluent or catalyst system deactivated reaction system effluent 931 prior to entering fractionation column 720b or optional flash drum 940 (not shown), iv) optional flash drum liquid stream 942 (not shown) prior to entering fractionation column 720b, v) bottoms stream 923b prior to contacting the bottoms stream 923b with the optional catalyst system quench agent 914a (e.g., when the reaction system effluent 730 is only contacted with the catalyst system deactivation agent 914), vi) bottoms stream 923b simultaneous with the contact of the bottoms stream 923 with the optional catalyst system quench agent 914a (e.g., when the reaction system effluent 730 is only contacted with the catalyst system deactivation agent 914), and vii) catalyst system quenched bottoms stream 924b (e.g., when the reaction system effluent 730 is only contacted with the catalyst system deactivation agent 914). Alternatively, or additionally, the beta-diketone can be contacted with the transition metal containing compound (or alternatively, chromium containing compound) present in other process streams within the separation system (e.g., a downstream heavies storage tank, among others).

Figure 13:
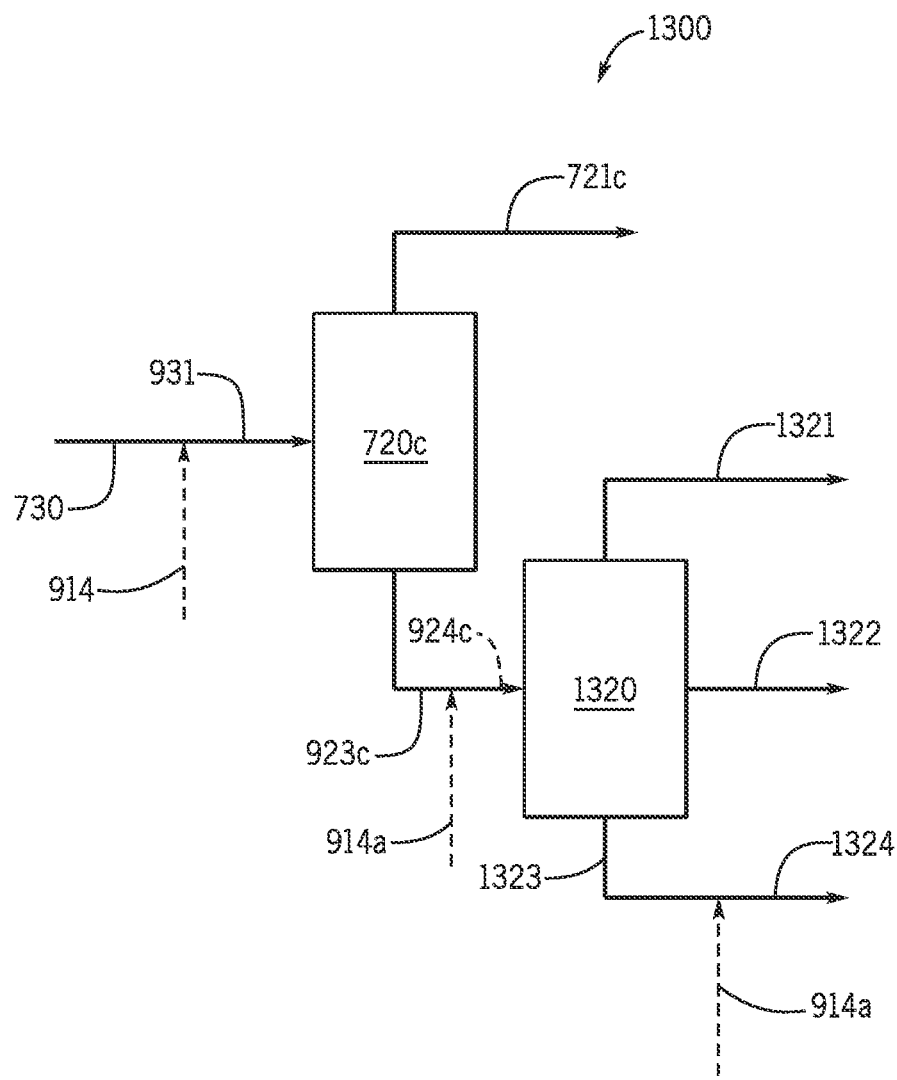

FIG. 13 depicts separation system 1300 used to separate components in a reaction system effluent 730 from a reaction system (not shown). Separation system 1300 has the option of i) contacting the reaction system effluent with a catalyst system deactivating and quench agent 914 to form a catalyst system deactivated and quenched reaction system effluent 931 (having the composition of a deactivated and quenched reaction system effluent stream 731) or ii) contacting the reaction system effluent 730 with a catalyst system deactivation agent 914 to form a catalyst system deactivated reaction system effluent 931 (having the composition of deactivated reaction system effluent stream 831). Catalyst system deactivated and quenched reaction system effluent or catalyst system deactivated reaction system effluent 931 can then be separated by fractionation column 720c into overhead stream 721c comprising ethylene and light trimerization co-products (trimerization product components having a boiling point less than the trimer) and bottoms stream 923c comprising), timer, reaction solvent, heavy trimerization co-products and deactivated and quenched or quenched catalyst system and/or catalyst system components. Fractionation column bottoms stream 923c may be or may not be contacted with catalyst system quench agent 914a (shown as an optional addition); e.g., fractionation column bottoms stream 923c can be optionally contacted with catalyst system quench agent 914a when reaction system effluent stream 730 is contacted with a catalyst system deactivation agent 914 to form catalyst system deactivated reactor effluent stream 931. Fractionation column 720c bottoms stream 923c (when not contacted with optional catalyst system quench agent 914a) or 924c (when contacted with optional catalyst system catalyst system quench agent 914a can then be separated by fractionation column 1320. In one embodiment, fractionation column 1320 can separate stream 923c or 924c into a) an overhead stream 1321 comprising trimer, b) side stream 1322 comprising reaction solvent (which may or may not be recycled back to the reaction system with or without additional processing), and b) bottoms stream 1323 comprising heavy trimerization co-products and deactivated and quenched or quenched catalyst system and/or catalyst system components. In another embodiment, fractionation column 1320 can separate stream 923c or 924c into a) an overhead stream 1321 comprising reaction solvent (which may or may not be recycled back to the reaction system with or without additional processing), b) side stream 1322 comprising timer, and b) bottoms stream 1323 comprising heavy trimerization co-products and deactivated and quenched or quenched catalyst system and/or catalyst system components. Fractionation column 1320 bottoms stream 1323 can be contacted with catalyst system quench agent 914a (shown as an optional addition), e.g., when reaction system effluent stream 730 is contacted with a catalyst system deactivation agent and fractionation column 720c bottoms stream is not contacted with optional quench agent 914a, to form quenched stream 1324 (comprising heavy trimerization co-products and deactivated and quenched catalyst system and/or catalyst system components). In some embodiments, overhead stream 721 can be further processed (not depicted) to isolate and/or purify the ethylene for recycle to the trimerization reactor. In some embodiments, fractionation column 720c can be operated as having a side stream withdraw (not shown) which can be utilized in a manner where stream 721 comprises ethylene and the side stream comprises light trimerization co-products. In further embodiments, bottoms stream 1323 or 1324 can be further processed (not depicted) to separate one or more heavy trimerization co-product streams from the catalyst system and/or catalyst system components. In yet other embodiments, separation system 1300 can further employ a flash drum 940 as depicted in FIG. 9 (not shown) to separate a catalyst system deactivated and quenched reaction system effluent or a deactivated catalyst system reaction system effluent into a vapor stream 941 (not shown) and a liquid stream 942 (not shown). The vapor stream 941 (not shown) and the liquid stream 942 (not shown) from the flash drum can be introduced into the fractionation column 720c at the appropriate locations. Employment of a flash drum 940 (not shown) can improve the efficiency of column 720c.

Fractionation columns 720c and 1320 can be continuous distillation columns with separation stages comprised of trays, packing material, or combinations thereof. Fractionation column 720c can be operated by recycling a portion of bottoms stream 923c back to the fractionation column 720c through a reboiler (not shown). A portion of the overhead stream 721 can be condensed and returned to the fractionation column 720c as reflux (not shown). Fractionation column 1320 can be operated by recycling a portion of bottoms stream 1323 back to the fractionation column 1320 through a reboiler (not shown). A portion of the overhead stream 1321 can be condensed and returned to the fractionation column 1320 as reflux (not shown). The reboilers (i.e., heat exchangers) which can be utilized in the recycling of a portion of 923c and/or 1323 to their respective fractionation column can be externally heated with heat transfer fluid. In an embodiment, accumulator vessels, reflux drums, and/or reflux pumps can facilitate introduction of the portion of the overhead stream 721 and/or 1321 utilized as reflux to their respective fractionation column.

In separation system 1300, the beta-diketone can be contacted with the transition metal containing compound (or alternatively, chromium containing compound) in any one or more streams within the separation system including i) the reaction system effluent 730 prior to contact with the catalyst system deactivation and quench agent or catalyst system deactivation agent 914, ii) the reaction system effluent 730 simultaneous with the contact of the catalyst system deactivation and quench agent or catalyst system deactivation agent 914, iii) the catalyst system deactivated and quenched reaction system effluent or catalyst system deactivated reaction system effluent 931 prior to entering fractionation column 720 or optional flash drum 940 (not shown), iv) optional flash drum liquid stream 942 (not shown) prior to entering fractionation column 720, v) bottoms stream 923c prior to contacting the bottoms stream 923c with the optional catalyst system quench agent 914a (e.g., when the reaction system effluent 730 is only contacted with the catalyst system deactivation agent 914), vi) bottoms stream 923b simultaneous with the contact of the bottoms stream 923 with the optional catalyst system quench agent 914a (e.g., when the reaction system effluent 730 is only contacted with the catalyst system deactivation agent 914 and bottoms stream 923c is contacted with quench agent 914a), vii) catalyst system quenched bottoms stream 924c (e.g., when the reaction system effluent 730 is only contacted with the catalyst system deactivation agent 914 and bottoms stream 923c is contacted with quench agent 914a), viii) bottoms stream 1323 prior to contacting the bottoms stream 1323 with the optional catalyst system quench agent 914a (e.g., when the reaction system effluent 730 is only contacted with the catalyst system deactivation agent 914 and bottoms stream 923c is not contacted with the optional quench agent 914a), ix) bottoms stream 1323 simultaneous with the contact of the bottoms stream 1323 with the optional catalyst system quench agent 914a (e.g., when the reaction system effluent 730 is only contacted with the catalyst system deactivation agent 914 and bottoms stream 1323 is contacted with quench agent 914a), and x) catalyst system quenched bottoms stream 1324 (e.g., when the reaction system effluent 730 is only contacted with the catalyst system deactivation agent 914 and bottoms stream 1323 is contacted with quench agent 914a). Alternatively, or additionally, the beta-diketone can be contacted with the transition metal containing compound (or alternatively, chromium containing compound) present in other process streams within the separation system (e.g., a downstream heavies storage tank, among others).

Figure 14:
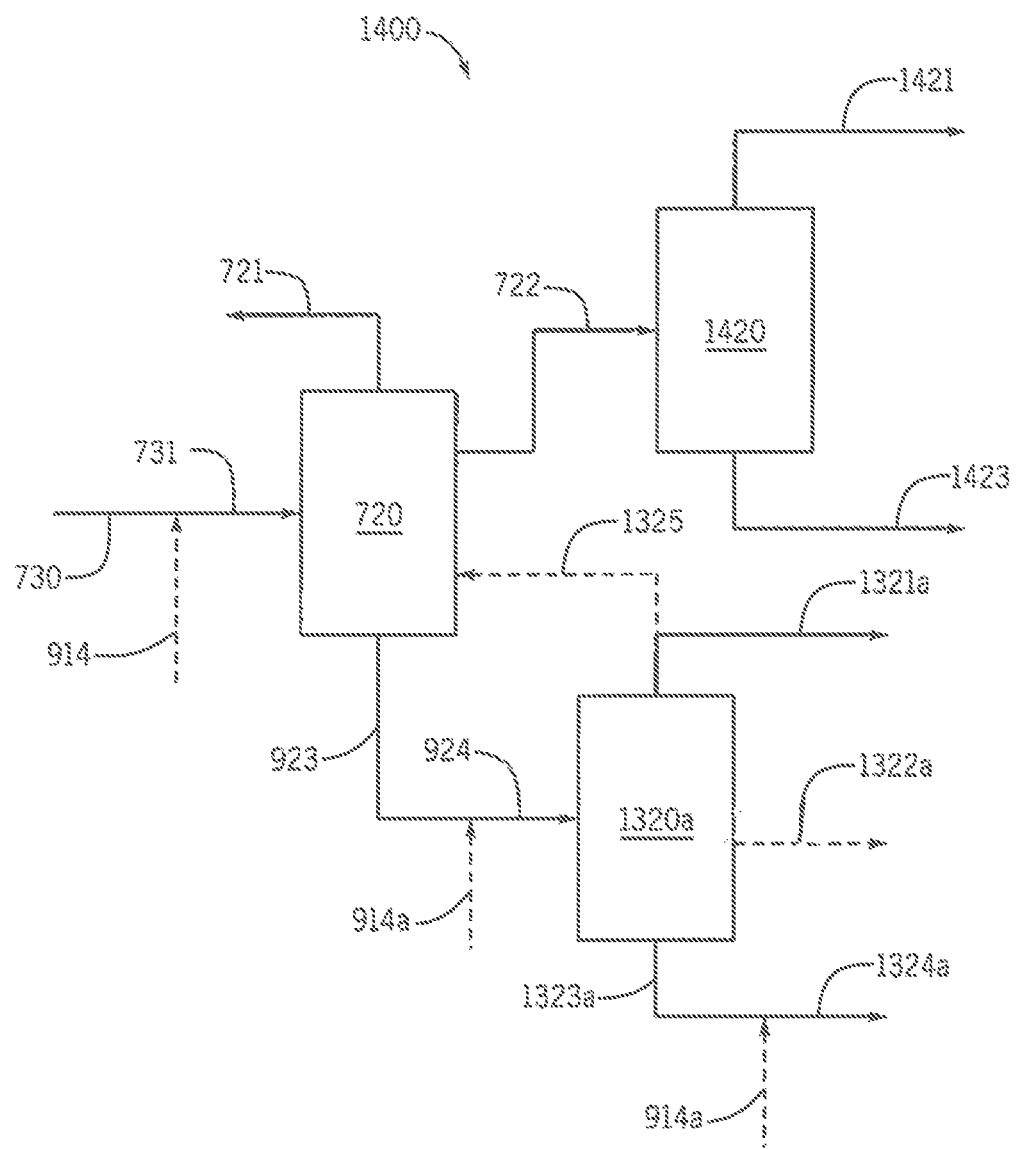

FIG. 14 depicts separation system 1400 used to separate components in a reaction system effluent 730 from a reaction system (not shown). Separation system 1400 represents a separation system combining elements of separation systems 700, 800, and 900 with the addition of a fractionation column 1420 for separating the components fractionation column side stream 722 and a fractionation column 1320a for separating the components in fractionation column 720 bottoms stream 923 or quench bottoms stream 924 (having any of the compositions described for streams 923 and/or 924 described for separation system 900). It should be noted that separation system 1400 can employ a flash drum 940 as depicted in FIG. 9 (not shown) to separate a catalyst system deactivated and quenched reaction system effluent or a deactivated catalyst system reaction system effluent into a vapor stream 941 (not shown) and a liquid stream 942 (not shown). The vapor stream 941 (not shown) and the liquid stream 942 (not shown) from the flash drum 940 can be introduced into the fractionation column 720 at the appropriate locations. Employment of a flash drum 940 (not shown) can improve the efficiency of column 720. Within separation system 1400, equipment and streams having the same number designation as those in separation systems 700, 800, and/or 900 can operate, can be processed, can have the same compositions, and/or have the same options described for processing streams as described for the separation system 700, 800, and/or 900 equipment and streams. In some embodiments, fractionation column 1120 can be operated as having a side stream withdraw (not shown) which can be utilized in a manner where stream 1121 comprises ethylene and the side stream comprises light trimerization co-products as described for the separation system 700, 800, and/or 900 equipment and stream.

Separation system 1400 differs from separation systems 700, 800, and/or 900 in that 1) fractionation column 720 side stream 722 can be fed to fractionation 1420 for the separation of components therein and 2) fractionation column 720 bottoms steam 923, or fractionation column 720 quenched bottoms steam 924 (having any of the compositions described for streams 923 and/or 924 described for separation system 900) can be fed to fractionation column 1320a for the separation of the components therein. Fractionation column 1420 can separate fractionation column 720 side stream 722 into i) an overhead stream 1421 comprising trimer and a bottoms stream 1423 comprising reaction solvent (which may or may not be recycled back to the reaction system with or without additional processing), or ii) an overhead stream 1421 comprising reaction solvent (which may or may not be recycled back to the reaction system with or without additional processing) and a bottoms stream 1423 comprising trimer. In an embodiment, fractionation column 1320a can separate stream 923 or 924 (comprising heavy trimerization co-products and the catalyst system deactivated and quenched or catalyst system quenched catalyst system and/or catalyst system components) into an overhead stream 1321a (comprising at least a portion of the liquid heavy trimerization co-products) and a bottoms stream 1324a (comprising at least a portion of the solid heavy trimerization co-products). In another embodiment, fractionation column 1320a can separate stream 923 or 924 (comprising heavy trimerization co-products and the catalyst system deactivated and quenched or catalyst system quenched catalyst system and/or catalyst system components) into an overhead stream 1321a (comprising a first fraction comprising at least a portion of the liquid heavy trimerization co-products), side stream 1322a (comprising a second fraction comprising at least a portion of the liquid heavy trimerization co-products), and a bottoms stream 1323a (comprising at least a portion of the solid heavy trimerization co-products). Fractionation column 1320a bottoms stream 1323a can then be contacted with catalyst system quench agent 914a (shown as an optional addition), e.g., when reaction system effluent stream 730 is contacted with a catalyst system deactivation agent and fractionation column 720 bottoms stream is not contacted with optional quench agent 914a, to form quenched stream 1324a (comprising at least a portion of the solid heavy trimerization co-products and deactivated and quenched catalyst system and/or catalyst system components). In some embodiments, overhead stream 721 can be further processed (not depicted) to isolate and/or purify the ethylene for recycle to the trimerization reactor. In yet other embodiments, separation system 1400 can further employ a flash drum 940 as depicted in FIG. 9 (not shown) to separate a catalyst system deactivated and quenched reaction system effluent or a deactivated catalyst system reaction system effluent into a vapor stream 941 (not shown) and a liquid stream 942 (not shown). The vapor stream 941 (not shown) and the liquid stream 942 (not shown) from the flash drum can be introduced into the fractionation column 720 at the appropriate locations. Employment of a flash drum 940 (not shown) can improve the efficiency of column 720.

The fractionation columns 1420 and 1320a can be continuous distillation columns with separation stages comprised of trays, packing material, or combinations thereof. Fractionation column 1420 can be operated by recycling a portion of bottoms stream 1423 back to the fractionation column 720 through a reboiler (not shown). A portion of the overhead stream 1421 can be condensed and returned to the fractionation column 1420 as reflux (not shown). Fractionation column 1320a can be operated by recycling a portion of bottoms stream 1323a back to the fractionation column 1320a through a reboiler (not shown). A portion of the overhead stream 1321a can be condensed and returned to the fractionation column 1320a as reflux (not shown). A portion of the overhead stream 1321a can be condensed and returned to the fractionation column 1320a as reflux and/or recycled back to fractionation column 720 (shown as optional stream 1325) through a reboiler. The reboilers (i.e., heat exchangers) which can be utilized in the recycling of a portion of 1423, 1323a, and/or optional 1325 to their respective fractionation column can be externally heated with heat transfer fluid. In an embodiment, accumulator vessels, reflux drums, and/or reflux pumps can facilitate introduction of the portion of the overhead stream 1421 and/or 1321 utilized as reflux to their respective fractionation column.

In separation system 1400, the beta-diketone can be contacted with the transition metal containing compound (or alternatively, chromium containing compound) in any one or more streams within the separation system including i) the reaction system effluent 730 prior to contact with the catalyst system deactivation and quench agent or catalyst system deactivation agent 914, ii) the reaction system effluent 730 simultaneous with the contact of the catalyst system deactivation and quench agent or catalyst system deactivation agent 914, iii) the catalyst system deactivated and quenched reaction system effluent or catalyst system deactivated reaction system effluent 931 prior to entering fractionation column 720 or optional flash drum 940 (not shown), iv) optional flash drum liquid stream 942 (not shown) prior to entering fractionation column 720, v) bottoms stream 923 prior to contacting the bottoms stream 923 with the optional catalyst system quench agent 914a (e.g., when the reaction system effluent 730 is only contacted with the catalyst system deactivation agent 914), vi) bottoms stream 923 simultaneous with the contact of the bottoms stream 923 with the optional catalyst system quench agent 914a (e.g., when the reaction system effluent 730 is only contacted with the catalyst system deactivation agent 914 and bottoms stream 923 is contacted with quench agent 914a), vii) catalyst system quenched bottoms stream 924 (e.g., when the reaction system effluent 730 is only contacted with the catalyst system deactivation agent 914 and bottoms stream 923 is contacted with quench agent 914a), viii) bottoms stream 1323a prior to contacting the bottoms stream 1323a with the optional catalyst system quench agent 914a (e.g., when the reaction system effluent 730 is only contacted with the catalyst system deactivation agent 914 and bottoms stream 923 is not contacted with the optional quench agent 914a), ix) bottoms stream 1323a simultaneous with the contact of the bottoms stream 1323a with the optional catalyst system quench agent 914a (e.g., when the reaction system effluent 730 is only contacted with the catalyst system deactivation agent 914 and bottoms stream 1323a is contacted with quench agent 914a), and x) catalyst system quenched bottoms stream 1324a (e.g., when the reaction system effluent 730 is only contacted with the catalyst system deactivation agent 914 and bottoms stream 1323a is contacted with quench agent 914a). Alternatively, or additionally, the beta-diketone can be contacted with the transition metal containing compound (or alternatively, chromium containing compound) present in other process streams within the separation system (e.g., a downstream heavies storage tank, among others).

Figure 15:
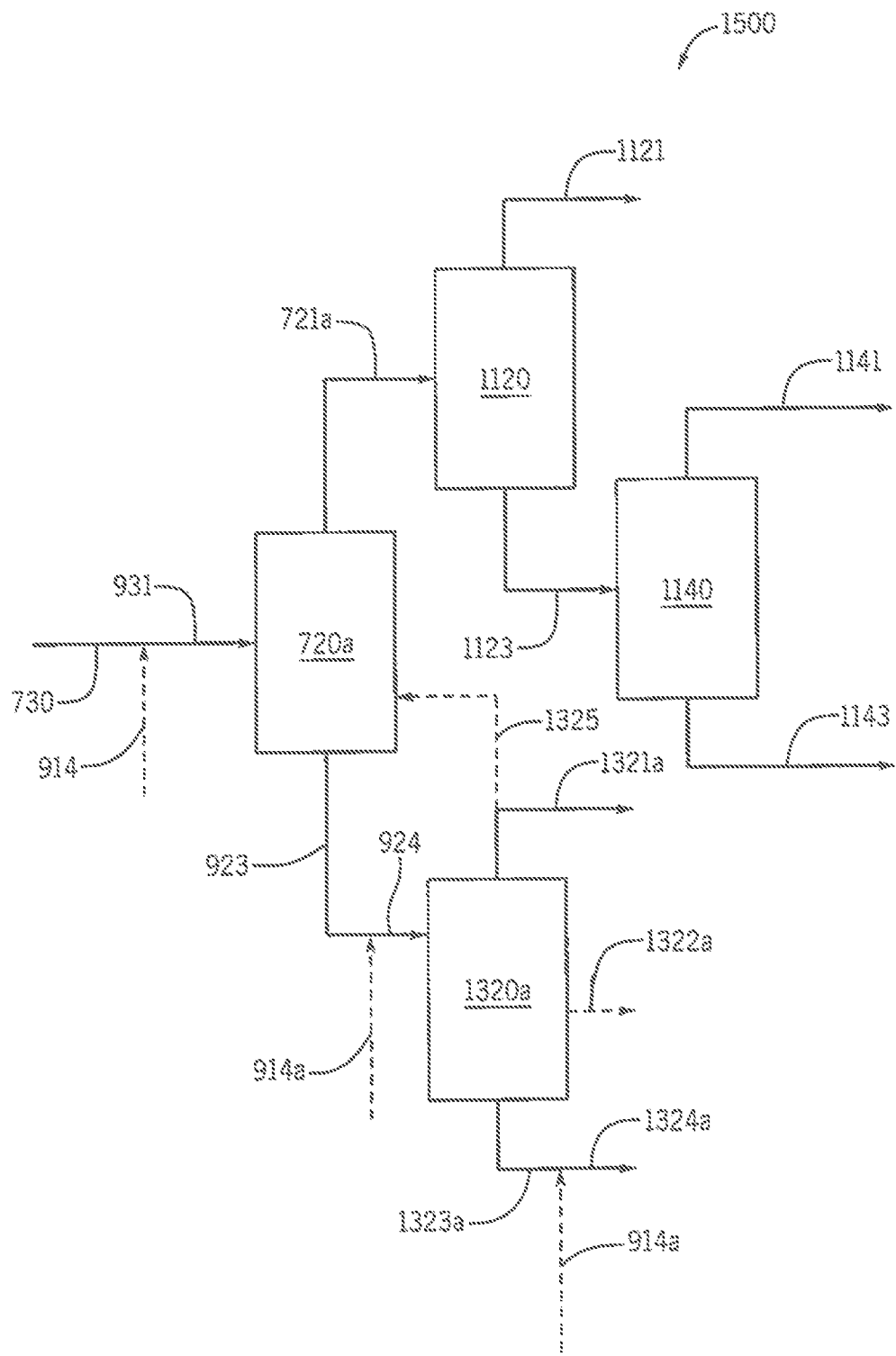

FIG. 15 depicts separation system 1500 used to separate components in a reaction system effluent 730 from a reaction system (not shown). Separation system 1500 represents an adaptation of separation system 1100 that includes fractionation column 1320a for separating the components fractionation column 720a bottoms stream 923 or quench bottoms stream 924 (having any of the compositions described for streams 923 and/or 924 described for separation system 900). It should be noted that separation system 1500 can employ a flash drum 940 as depicted in FIG. 9 (not shown) to separate a catalyst system deactivated and quenched reaction system effluent or a deactivated catalyst system reaction system effluent into a vapor stream 941 (not shown) and a liquid stream 942 (not shown). The vapor stream 941 (not shown) and the liquid stream 942 (not shown) from the flash drum 940 can be introduced into the fractionation column 720 at the appropriate locations. Employment of a flash drum 940 (not shown) can improve the efficiency of column 720. Within separation system 1500, equipment and streams having the same number designation as those in separation system 1100 can operate, can be processed, can have the same compositions, and/or have the same options described for processing streams as described for the separation system 1100 equipment and streams.

Separation system 1500 differs from separation system 1100 in that fractionation column 720a bottoms stream 923 or fractionation column 720a quenched bottoms steam 924 (having any of the compositions described for streams 923 and/or 924 described for separation system 900) can be fed to fractionation column 1320a for the separation of the components therein. In an embodiment, fractionation column 1320a can separate stream 923 or 924 (comprising heavy trimerization co-products and the catalyst system deactivated and quenched or catalyst system quenched catalyst system and/or catalyst system components) into an overhead stream 1321a (comprising at least a portion of the liquid heavy trimerization co-products) and a bottoms stream 1323a (comprising at least a portion of the solid heavy trimerization co-products and the catalyst system deactivated and quenched or catalyst system quenched catalyst system and/or catalyst system components). In another, embodiment, fractionation column 1320a can separate stream 923 or 924 (comprising heavy trimerization co-products and the catalyst system deactivated and quenched or catalyst system quenched catalyst system and/or catalyst system components) into an overhead stream 1321*a* (comprising a first fraction comprising at least a portion of the liquid heavy trimerization co-products), side stream 1322*a* (comprising a second fraction comprising at least a portion of the liquid heavy trimerization co-products), and a bottoms stream 1323*a* (comprising at least a portion of the solid heavy trimerization co-products the catalyst system deactivated and quenched or catalyst system quenched catalyst system and/or catalyst system components). Fractionation column 1320*a* bottoms stream 1323*a* can then be contacted with catalyst system quench agent 914*a* (shown as an optional addition), e.g., when reaction system effluent stream 730 is contacted with a catalyst system deactivation agent and fractionation column 720 bottoms stream is not contacted with optional quench agent 914*a*, to form quenched stream 1324*a* (comprising at least a portion of the solid heavy trimerization co-products and deactivated and quenched catalyst system and/or catalyst system components).

Fractionation column 1320*a* can be continuous distillation columns with separation stages comprised of trays, packing material, or combinations thereof. Fractionation column 1320*a* can be operated by recycling a portion of bottoms stream 1323*a* back to the fractionation column 1320*a* through a reboiler (not shown). A portion of the overhead stream 1321*a* can be condensed and returned to the fractionation column 1320*a* as reflux and/or recycled back to fractionation column 720 (shown as optional stream 1325) through a reboiler. The reboilers (i.e., heat exchangers) which can be utilized in the recycling of a portion of 1323*a* and/or optional 1325 to their respective fractionation column can be externally heated with heat transfer fluid. In an embodiment, accumulator vessels, reflux drums, and/or reflux pumps can facilitate introduction of the portion of overhead stream 1321*a* utilized as reflux to the fractionation column 1320*a*.

In separation system 1500, the beta-diketone can be contacted with the transition metal containing compound (or alternatively, chromium containing compound) in any one or more streams within separation system including i) the reaction system effluent 730 prior to contact with the catalyst system deactivation and quench agent or catalyst system deactivation agent 914, ii) the reaction system effluent 730 simultaneous with the contact of the catalyst system deactivation and quench agent or catalyst system deactivation agent 914, iii) the catalyst system deactivated and quenched reaction system effluent or catalyst system deactivated reaction system effluent 931 prior to entering fractionation column 720*a* or optional flash drum 940 (not shown), iv) optional flash drum liquid stream 942 (not shown) prior to entering fractionation column 720*a*, v) bottoms stream 923 prior to contacting the bottoms stream 923 with the optional catalyst system quench agent 914*a* (e.g., when the reaction system effluent 730 is only contacted with the catalyst system deactivation agent 914), vi) bottoms stream 923 simultaneous with the contact of the bottoms stream 923 with the optional catalyst system quench agent 914*a* (e.g., when the reaction system effluent 730 is only contacted with the catalyst system deactivation agent 914 and bottoms stream 923 is contacted with quench agent 914*a*), vii) catalyst system quenched bottoms stream 924 (e.g., when the reaction system effluent 730 is only contacted with the catalyst system deactivation agent 914 and bottoms stream 923 is contacted with quench agent 914*a*), viii) bottoms stream 1323*a* prior to contacting the bottoms stream 1323*a* with the optional catalyst system quench agent 914*a* (e.g., when the reaction system effluent 730 is only contacted with the catalyst system deactivation agent 914 and bottoms stream 923 is not contacted with the optional quench agent 914*a*), ix) bottoms stream 1323*a* simultaneous with the contact of the bottoms stream 1323*a* with the optional catalyst system quench agent 914*a* (e.g., when the reaction system effluent 730 is only contacted with the catalyst system deactivation agent 914 and bottoms stream 1323*a* is contacted with quench agent 914*a*), and x) catalyst system quenched bottoms stream 1324*a* (e.g., when the reaction system effluent 730 is only contacted with the catalyst system deactivation agent 914 and bottoms stream 1323*a* is contacted with quench agent 914*a*). Alternatively, or additionally, the beta-diketone can be contacted with the transition metal containing compound (or alternatively, chromium containing compound) present in other process streams within the separation system (e.g., a downstream heavies storage tank, among others).

Figure 16:
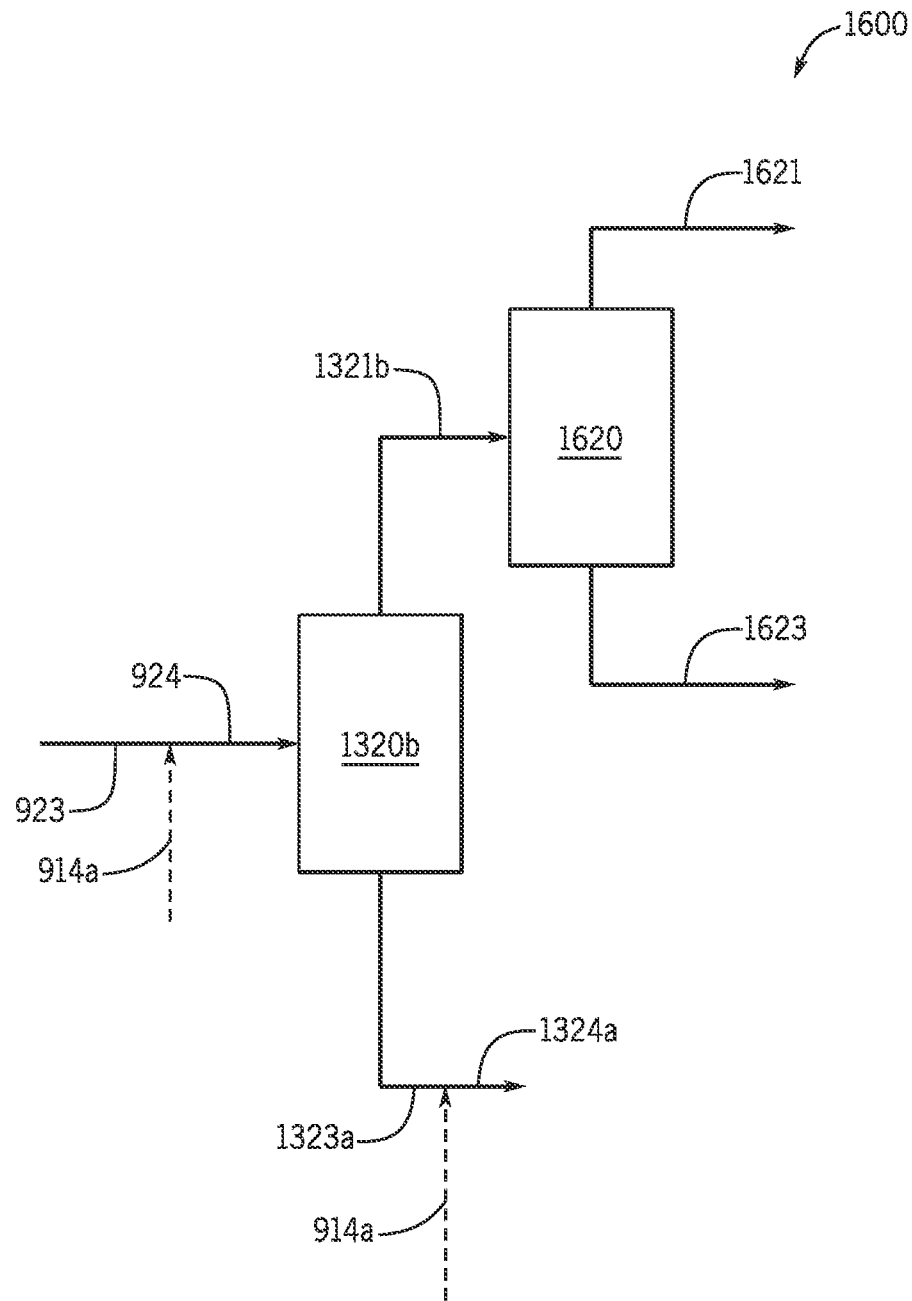

FIG. 16 depicts separation system 1600 which represents an adaptation for processing bottoms stream 923 or quenched bottoms stream 924 (via addition of the optional quench agent 914*a*) that can be added to separation systems 900, 1000, and/or 1100 or substituted for fractionation column 1320*a* and its streams in separation systems 1400 and/or 1500. Within separation system 1600, equipment and streams having the same number designation as those in separation system 900, 1000, 1100, 1400, and/or 1500 can operate, can be processed, can have the same compositions, and/or can have the same options described for processing streams as described for the separation system 900, 1000, 1100, 1400, and/or 1500 equipment and streams.

In separation system 1600 bottoms stream 923 or quenched bottoms stream 924 can be fed to fractionation column 1320*b* for the separation of the components therein. In an embodiment, fractionation column 1320*b* can separate stream 923 or 924 (comprising heavy trimerization co-products and the catalyst system deactivated and quenched or catalyst system quenched catalyst system and/or catalyst system components) into an overhead stream 1321*b* (comprising at least a portion of the liquid heavy trimerization co-products) and a bottoms stream 1323*a* (comprising at least a portion of the solid heavy trimerization co-products and the catalyst system deactivated and quenched or catalyst system quenched catalyst system and/or catalyst system components). Overhead stream 1321*b* can then be feed to fractionation column 1620 to provide an overhead stream 1621 (comprising a first fraction comprising at least a portion of the liquid heavy trimerization co-products) and bottoms stream 1623 (comprising a second fraction comprising at least a portion of the liquid heavy trimerization co-products). Fractionation column 1320*b* bottoms stream 1323*a* can be contacted with catalyst system quench agent 914*a* (shown as an optional addition), e.g., when reaction system effluent stream 730 is contacted with a catalyst system deactivation agent and fractionation column 720 or 720*a* bottoms stream is not contacted with optional quench agent 914*a*, to form quenched stream 1324*a* (comprising at least a portion of the solid heavy trimerization co-products and deactivated and quenched catalyst system and/or catalyst system components).

Fractionation columns 1320*b* and/or 1620 can be continuous distillation columns with separation stages comprised of trays, packing material, or combinations thereof. Fractionation column 1320*b* can be operated by recycling a portion of bottoms stream 1323*a* back to the fractionation column 720 or 720*a* through a reboiler (not shown). A portion of the overhead stream 1321*b* can be condensed and returned to the fractionation column 1320b as reflux and/or recycled back to fractionation column 720 or 720a through a reboiler. Fractionation column 1620 can be operated by recycling a portion of bottoms stream 1623 back to the fractionation column 1620 through a reboiler (not shown). A portion of the overhead stream 1621 can be condensed and returned to the fractionation column 1620 as reflux. The reboilers (i.e., heat exchangers) which can be utilized to recycle of a portion of 1323a and/or 1623 to their respective fractionation column can be externally heated with heat transfer fluid. An accumulator vessel, reflux drum, and/or reflux pump, can facilitate introduction of the portion of overhead stream 1321b and/or 1621 utilized as reflux to their respective fractional columns.

When using separation system 1600 as an addition to separation systems 900, 1000, and/or 1100 or as a substitution of fractionation column 1320a in separation systems 1400 and/or 1500, the beta-diketone can be contacted with the transition metal containing compound (or alternatively, chromium containing compound) in any one or more streams within the separation system 900, 1000, 1100, 1400, and/or 1500 to which it can added or replaced. Additionally, within separation system 1600, the beta-diketone can be contacted with the transition metal containing compound (or alternatively, chromium containing compound) in any one or more streams within the separation system including i) bottoms stream 1323a prior to contacting the bottoms stream 1323a with the optional catalyst system quench agent 914a (e.g., when the reaction system effluent 730 is only contacted with the catalyst system deactivation agent 914 and bottoms stream 923 is not contacted with the optional quench agent 914a), ii) bottoms stream 1323a simultaneous with the contact of the bottoms stream 1323a with the optional catalyst system quench agent 914a (e.g., when the reaction system effluent 730 is only contacted with the catalyst system deactivation agent 914 and bottoms stream 1323a is contacted with quench agent 914a), and iii) catalyst system quenched bottoms stream 1324a (e.g., when the reaction system effluent 730 is only contacted with the catalyst system deactivation agent 914 and bottoms stream 1323a is contacted with quench agent 914a). Alternatively, or additionally, the beta-diketone can be contacted with the transition metal containing compound (or alternatively, chromium containing compound) present in other process streams within the separation system utilizing separation system 1600 (e.g., a downstream heavies storage tank, among others).

Figure 17:
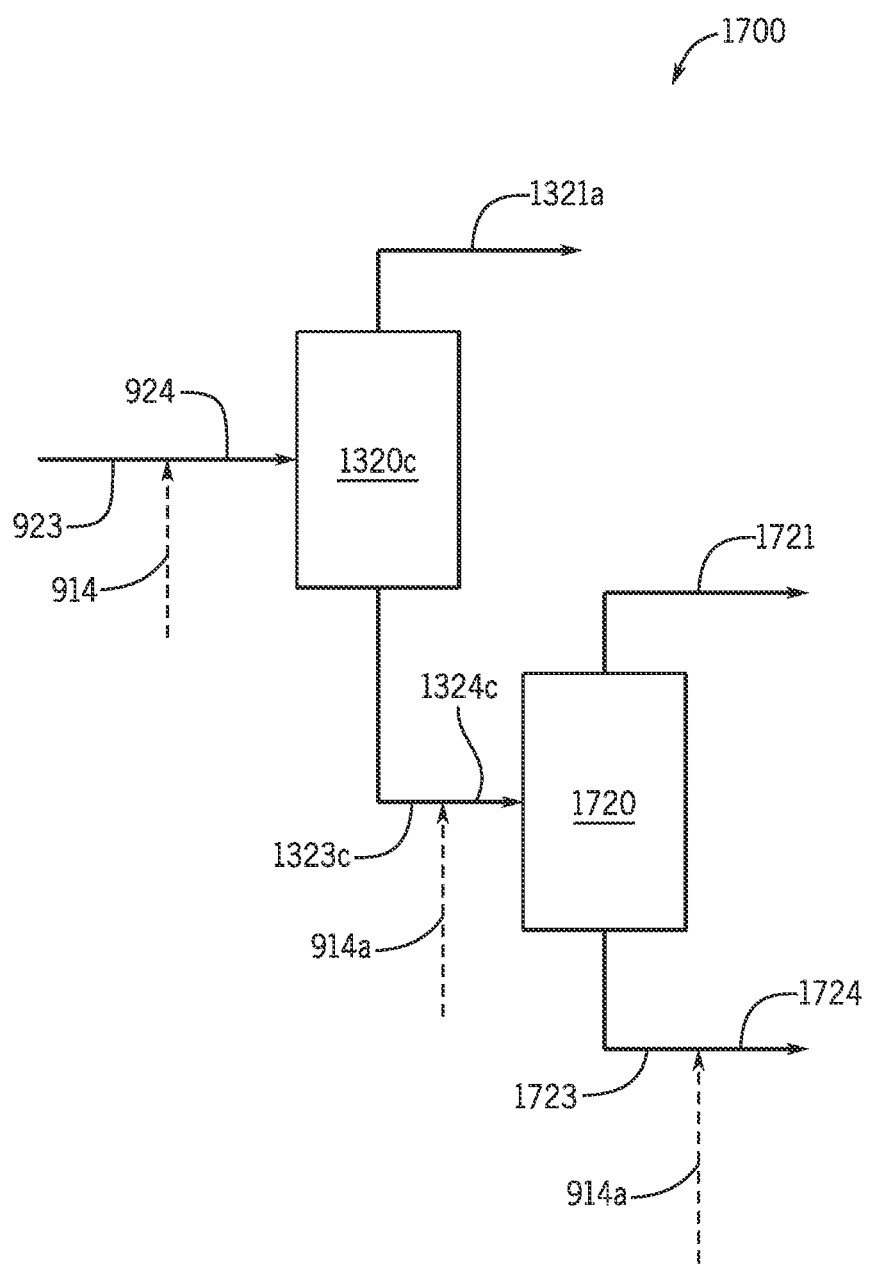

FIG. 17 depicts separation system 1700 which represents an adaptation for processing bottoms stream 923 or quenched bottoms stream 924 (via addition of the optional quench agent 914a) that can be applied to separation systems 900, 1000, and/or 1100 or as a substitution for fractionation column 1320a and its streams in separation systems 1400 and/or 1500. Within separation system 1700, equipment and streams having the same number designation as those in separation systems 900, 1000, 1100, 1400, and/or 1500 can operate, can be processed, can have the same compositions, and/or can have the same options described for processing streams as described for the separation system 900, 1000, 1100, 1400, and/or 1500 equipment and streams.

In separation system 1700 bottoms stream 923 or quenched bottoms stream 924 can be fed to fractionation column 1320c for the separation of the components therein. In an embodiment, fractionation column 1320c can separate stream 923 or 924 (comprising heavy trimerization co-products and the catalyst system deactivated and quenched or catalyst system quenched catalyst system and/or catalyst system components) into an overhead stream 1321a (a first fraction comprising at least a portion of the liquid heavy trimerization co-products) and a bottoms stream 1323c (comprising at least a portion of the liquid heavy trimerization co-products, the solid heavy trimerization co-products, and the catalyst system deactivated and quenched or catalyst system quenched catalyst system and/or catalyst system components). Bottoms stream 1323c can then be feed to fractionation column 1720 to provide an overhead stream 1721 (a second fraction comprising at least a portion of the liquid heavy trimerization co-products) and bottoms stream 1723 (comprising the solid heavy trimerization co-products, and the catalyst system deactivated and quenched or catalyst system quenched catalyst system and/or catalyst system components). Fractionation column 1320c bottoms stream 1323c can be contacted with catalyst system quench agent 914a (shown as an optional addition), e.g., when reaction system effluent stream 730 is contacted with a catalyst system deactivation agent and fractionation column 720 or 720a bottoms stream is not contacted with optional quench agent 914a, to form quenched stream 1324c (comprising at least a portion of the liquid heavy trimerization co-products, the solid heavy trimerization co-products and deactivated and quenched catalyst system and/or catalyst system components). Fractionation column 1720 bottoms stream 1723 can be contacted with catalyst system quench agent 914a (shown as an optional addition), e.g., when reaction system effluent stream 730 is contacted with a catalyst system deactivation agent, fractionation column 720 or 720a bottoms stream 923 is not contacted with optional quench agent 914a, and fractionation column 1320c bottoms stream 1323c is not contacted with optional quench agent 914a, to form quenched stream 1724 (comprising at least a portion of the solid heavy trimerization co-products and deactivated and quenched catalyst system and/or catalyst system components).

Fractionation columns 1320c and/or 1720 can be continuous distillation columns with separation stages comprised of trays, packing material, or combinations thereof. Fractionation column 1320c can be operated by recycling a portion of bottoms stream 1323c back to the fractionation column 720a through a reboiler (not shown). Portions of the overhead stream 1321a can be condensed and returned to the fractionation column 1320c as reflux and/or recycled back to fractionation column 720 or 720a through a reboiler. Fractionation column 1720 can be operated by recycling a portion of bottoms stream 1723 back to the fractionation column 1620 through an optional reboiler (not shown). Portions of the overhead stream 1721 can be condensed and returned to the fractionation column 1720 as reflux and/or recycled back to fractionation column 1320c through an optional reboiler. The reboilers (i.e., heat exchangers) which can be utilized in the recycling of a portion of 1321a, 1323c, 1721, and/or 1723 to their respective fractionation column can be externally heated with heat transfer fluid. An accumulator vessel, reflux drum, and/or reflux pump, can facilitate introduction of the portion of overhead stream 1321a and/or 1721 utilized as reflux to their respective fractional columns.

When using separation system 1700 as an addition to separation systems 900, 1000, and/or 1100 or as a substitution of fractionation column 1320a in separation systems 1400 and/or 1500, the beta-diketone can be contacted with the transition metal containing compound (or alternatively, chromium containing compound) in any one or more streams within the separation system 900, 1000, 1100, 1400, and/or 1500 to which it added or replaced. Additionally, within separation system 1700, the beta-diketone can be contacted with the transition metal containing compound (or alternatively, chromium containing compound) in any one or more streams within the separation system including i) bottoms stream 1323c prior to contacting the bottoms stream 1323c with the optional catalyst system quench agent 914a (e.g., when the reaction system effluent 730 is only contacted with the catalyst system deactivation agent 914 and bottoms stream 923 is not contacted with the optional quench agent 914a), ii) bottoms stream 1323c simultaneous with the contact of the bottoms stream 1323c with the optional catalyst system quench agent 914a (e.g., when the reaction system effluent 730 is only contacted with the catalyst system deactivation agent 914 and bottoms stream 1323c is contacted with quench agent 914a), iii) catalyst system quenched bottoms stream 1324c (e.g., when the reaction system effluent 730 is only contacted with the catalyst system deactivation agent 914 and bottoms stream 1323a is contacted with quench agent 914a), iv) bottoms stream 1723 prior to contacting the bottoms stream 1723 with the optional catalyst system quench agent 914a (e.g., when the reaction system effluent 730 is only contacted with the catalyst system deactivation agent 914 and bottoms stream 923 and 1323c is not contacted with the optional quench agent 914a), ii) bottoms stream 1723 simultaneous with the contact of the bottoms stream 1723 with the optional catalyst system quench agent 914a (e.g., when the reaction system effluent 730 is only contacted with the catalyst system deactivation agent 914 and bottoms stream 1723 is contacted with quench agent 914a), iii) catalyst system quenched bottoms stream 1724 (e.g., when the reaction system effluent 730 is only contacted with the catalyst system deactivation agent 914 and bottoms stream 1723 is contacted with quench agent 914a). Alternatively, or additionally, the beta-diketone can be contacted with the transition metal containing compound (or alternatively, chromium containing compound) present in other process streams within the separation system utilizing separation system 1700 (e.g., a downstream heavies storage tank, among others).

It is further contemplated that features of one or more of the embodiments described herein can be combined within other embodiments. For example, a flash drum, such as flash drum 940 in FIG. 9, can be utilized in one or more embodiments, such as those illustrated in FIGS. 14-17. Additionally, while not explicitly discussed or shown, fractionation towers 720b, 720c, 1120, 1120b, 1140, 1140b, 1220, 1320b, 1320c, 1420, 1620, and 1729 can have optional side streams having the appropriate compositions to provide the desired overhead, side, and bottoms streams for the desired separation and/or specific purpose and configuration of the separation system.

EXAMPLES

The invention having been generally described, the following examples are given as particular embodiments of the invention and to demonstrate the practice and advantages thereof. It is understood that the examples are given by way of illustration and are not intended to limit the specification of the claims in any manner. (e.g., a downstream heavies storage tank, among others) illustrated in separation system 1700.

A number of experiments were undertaken to frame the potential reaction conditions necessary to deactivate black solids. Unless specified otherwise, all reactions were performed under an inert nitrogen atmosphere in an at least substantially dry atmosphere glovebox (drybox). Reactions were conducted in a 20 mL glass vial stirred with a Teflon® stir bar and heated, if necessary, using a brass heating block.

Black solids were obtained as a by-product of a 1-hexene production process, as described in the Specification herein and characterized with the following results: (1) amorphous; (2) surface area of 121 $M^2/g$; (3) chromium content of 57 wt. %; and (4) bulk density of 0.857 g/mL.

Example 1

Control

Experiment 1 included stirring 0.50 g of black solids and 5 g of ethylbenzene at 120° C. for 2 hours. The resultant mixture was filtered yielding black solids and a yellow solution. The black solids were rinsed with cyclohexane (10 mL) and dried under vacuum. The black solids reacted rapidly with air producing white smoke and glowing red.

Example 2

Acetylacetone

Experiment 2 included stirring 0.50 g of black solids and 1.73 g of acetylacetone and 5 g of ethylbenzene at room temperature for 2 hours. The resultant mixture was filtered, yielding black solids and a yellow solution. The black solids were rinsed with cyclohexane (10 mL) and dried under vacuum. The black solids reacted rapidly with air producing white smoke and glowing red.

Example 3

Acetylacetone and Heating

Experiment 3 included stirring 0.50 g of black solids and 1.73 g of acetylacetone and 5 g of ethylbenzene at 120° C. for 2 hours. The resultant mixture was filtered, yielding black solids and a dark reddish-brown solution. The black solids were rinsed with cyclohexane (10 mL) and dried under vacuum. The black solids did not visibly react in the presence of air.

Example 4

Stoichiometric Excess

Experiment 4 included stirring 0.20 g of black solids and 2.70 g of acetylacetone at 120° C. for 2 days. The resultant mixture was extracted with 5 mL of hot ethylbenzene and filtered, yielding black solids and a purple solution. Removal of the solvent from the filtrate yielded purple crystals chromium(III) acetylacetonate (0.192 g).

Example 5

1-Decene, Short Time

Experiment 5 included stirring 0.50 g of black solids and 1.73 g of acetylacetone and 5 g of 1-decene at 120° C. for 15 minutes. The resultant mixture was filtered, yielding black solids and an orange-red solution. The black solids were rinsed with cyclohexane (10 mL) and dried under vacuum. The black solids reacted rapidly with air, producing white smoke and glowing red.

Example 6

1-Decene, Longer Time

Experiment 6 included stirring 0.50 g of black solids and 1.73 g of acetylacetone and 5 g of 1-decene at 120° C. for 18 hours. The resultant mixture was filtered, yielding purple and black solids and a brown solution. The solids were rinsed with cyclohexane (10 mL) and dried under vacuum. The solids did not visibly react in the presence of air.

CLOSING OF THE DETAILED DESCRIPTION

The invention illustratively disclosed herein suitably can be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above can vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values.

Herein certain terms have been defined for use herein. Unless otherwise indicated, the definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition can be applied. To the extent that any definition or usage provided by any document incorporated herein by reference conflicts with the definition or usage provided herein, the definition or usage provided herein controls.

All publications and patents mentioned herein are incorporated herein by reference. The publications and patents mentioned herein can be utilized for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

Therefore, the present invention is well adapted to attain the ends and advantages mentioned as well as those that are inherent therein. This concludes the detailed description. The particular embodiments disclosed above are illustrative only, as the invention can be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above can be altered or modified and all such variations are considered within the scope and spirit of the invention. Accordingly, the protection sought herein is as set forth in the claims below.

What is claimed is:

1. A process of forming an oligomerization product comprising:
    contacting an olefin and a catalyst system to form an oligomerization product at oligomerization conditions, wherein a reaction system effluent comprises components selected from the oligomerization product, a chromium containing compound, pr combinations thereof; and
    adding a beta-diketone to the chromium containing compound in i) the reaction system effluent, ii) a deactivated reaction system effluent stream, iii) a deactivated and quenched reaction system effluent, or iv) a reaction system effluent stream, a deactivated reaction system effluent stream, or a deactivated and quenched reaction system effluent stream which has been processed to remove one or more materials comprising all or a portion of ethylene, the oligomerization product, and/or reaction solvent, at conditions capable of changing an oxidation state of chromium.

2. The process of claim 1, wherein the beta-diketone is added to the chromium containing compound in the presence of the oligomerization product.

3. The process of claim 1, further comprising separating at least a portion of the components within the reaction system effluent.

4. The process of claim 3, wherein the separation comprises at least one separation vessel selected from columns, tanks, flash vessels, distillation columns, or combinations thereof, and wherein the beta-diketone is added to the chromium containing compound at one or more locations within the separation.

5. The process of claim 3, wherein the beta-diketone is added to the chromium containing compound prior to separation of the components.

6. The process of claim 1, further comprising:
    separating light boiling components from heavier boiling components present in the reaction system effluent within a first vessel to form a first vessel overhead stream and a first vessel bottoms stream, wherein the first vessel bottoms stream comprises at least a portion of the chromium containing compound; and
    adding the beta-diketone to the first vessel bottoms stream.

7. The process of claim 6, wherein the first vessel comprises a flash vessel.

8. The process of claim 1, further comprising:
    separating light boiling components from heavier boiling components present in the reaction system effluent within a first vessel to form a first vessel overhead stream and a first vessel bottoms stream, wherein the first vessel bottoms stream comprises the chromium containing compound;
    passing the first vessel bottoms stream to a second vessel adapted to separate the components therein and form a second vessel overhead stream and a second vessel bottoms stream, wherein the second vessel bottoms stream comprises at least a portion of the chromium containing compound; and
    adding the beta-diketone to the second vessel bottoms stream.

9. The process of claim 1, further comprising:
    separating light boiling components from heavier boiling components present in the reaction system effluent within a first vessel to form a first vessel overhead stream and a first vessel bottoms stream, wherein the first vessel bottoms stream comprises at least a portion of the chromium containing compound;

passing the first vessel bottoms stream to a second vessel adapted to separate the components therein and form a second vessel overhead stream and a second vessel bottoms stream, wherein the second vessel bottoms stream comprises at least a portion of the chromium containing compound;

passing the second vessel bottoms stream to a third vessel adapted to separate the components therein and form a third vessel overhead stream and a third vessel bottoms stream, wherein the third vessel bottoms stream comprises at least a portion of the chromium containing compound; and adding the beta-diketone to the third vessel bottoms stream.

10. The process of claim 1, further comprising:

storing at least a portion of the reaction system effluent within a storage vessel; and wherein the at least a portion of the reaction system effluent comprises at least a portion of the chromium containing compound; and adding the beta-diketone to the reaction system effluent within the storage vessel.

11. The process of claim 1, further comprising:

separating light boiling components from heavier boiling components present in the reaction system effluent within a first vessel to form a first vessel overhead stream and a first vessel bottoms stream, wherein the first vessel bottoms stream comprises the chromium containing compound;

passing the first vessel bottoms stream to a second vessel adapted to separate the components therein and form a second vessel overhead stream and a second vessel bottoms stream, wherein the second vessel bottoms stream comprises at least a portion of the chromium containing compound;

passing the second vessel bottoms stream to a third vessel adapted to separate the components therein and form a third vessel overhead stream and a third vessel bottoms stream, wherein the third vessel bottoms stream comprises at least a portion of the chromium containing compound;

storing at least a portion of the third vessel bottoms stream within a storage vessel; and adding the beta-diketone to the third vessel bottoms stream within the storage vessel.

12. The process of claim 1, further comprising:

separating light boiling components from heavier boiling components present in the reaction system effluent within a first vessel to form a first vessel overhead stream and a first vessel bottoms stream, wherein the first vessel bottoms stream comprises at least a portion of the chromium containing compound;

passing the first vessel bottoms stream to a second vessel adapted to separate the components therein and form a second vessel overhead stream and a second vessel bottoms stream, wherein the second vessel bottoms stream comprises at least a portion of the chromium containing compound;

passing the second vessel bottoms stream to a third vessel adapted to separate the components therein and form a third vessel overhead stream and a third vessel bottoms stream, wherein the third vessel bottoms stream comprises at least a portion of the chromium containing compound;

storing at least a portion of the third vessel bottoms stream within a storage vessel; and adding the beta-diketone to a) the reaction system effluent, b) the first vessel bottoms stream, c) the second vessel bottoms stream, d) the third vessel bottoms stream, e) the reaction system effluent, the first vessel bottoms stream, the second vessel bottoms stream, or the third vessel bottoms stream within the storage vessel, or f) combinations thereof.

13. The process of claim 1, wherein the beta-diketone is selected from $C_5$ to $C_{30}$ beta-diketones.

14. The process of claim 1, wherein the beta-diketone is selected from $C_5$ to $C_{20}$ beta-diketones.

15. The process of claim 1, wherein the beta-diketone is selected from $C_5$ to $C_{10}$ beta-diketones.

16. The process of claim 1, wherein the beta-diketone is selected from acetylacetone, dibenzoylmethane, dipivaloylmethane, hexafluoroacetylacetone, or combinations thereof.

17. The process of claim 1, wherein the beta-diketone has a water content of less than 200 ppm by weight.

18. The process of claim 1, wherein the catalyst system comprises chromium, a heteroatomic ligand, and a metal alkyl compound.

19. The process of claim 17, wherein the heteroatomic ligand is selected from pyrrole compounds, diphosphinoaminyl compounds, $N^2$-phosphinylamidine compounds, $N^2$-phosphinylformamidine compounds, phosphinyl guanidine compounds, or combinations thereof.

20. The process of claim 1, wherein the catalyst system comprises:

a) a chromium compound, a pyrrole compound, a metal alkyl compound, and optionally, a halide containing compound;

b) a chromium compound, a diphosphinoaminyl compound, and a metal alkyl compound;

c) a chromium compound complexed to a diphosphinoaminyl compound, and a metal alkyl compound;

d) a chromium compound, an $N^2$-phosphinylamidine compound, and a metal alkyl compound;

e) a chromium compound complexed to an $N^2$-phosphinylamidine compound, and a metal alkyl compound;

f) a chromium compound, an $N^2$-phosphinylformamidine compound, and a metal alkyl compound;

g) a chromium compound complexed to an $N^2$-phosphinylformamidine compound, and a metal alkyl compound;

h) a chromium compound, an $N^2$-phosphinyl guanidine compound, and a metal alkyl compound;

i) a chromium compound complexed to an $N^2$-phosphinyl guanidine compound, and a metal alkyl compound; or j) combinations thereof.

21. The process of claim 18, wherein the metal alkyl compound is selected from alkylaluminum compounds, aluminoxanes, or combinations thereof.

22. The process of claim 1, further comprising contacting the catalyst system in the reaction system effluent with i) a catalyst system deactivating and quench agent or ii) a catalyst system deactivating agent.

23. The process of claim 22, wherein the catalyst system deactivating and quench agent or catalyst system deactivating agent is selected from the group consisting of monoalcohols, diols, polyols, and mixtures thereof.

24. The process of claim 22, wherein the beta-diketone is added to the chromium containing compound in the presence of the catalyst system deactivating and quench agent or catalyst system deactivating agent.

25. The process of claim 22, wherein the catalyst system deactivating and quench agent or catalyst system deactivating agent is selected from a $C_4$ to $C_{12}$ mono-alcohol.

26. The process of claim 22, wherein the catalyst system deactivating and quench agent or catalyst system deactivating agent comprises 2-ethyl-1-hexanol.

27. The process of claim 1, wherein the olefin comprises ethylene.

28. The process of claim 1, wherein the oligomerization product comprises 1-hexene, 1-octene, or combinations thereof.

29. The process of claim 1, wherein the beta-diketone is added to the chromium containing compound in an amount sufficient to render the chromium containing compound non-pyrophoric.

* * * * *